US006765006B2

(12) United States Patent
Upasani et al.

(10) Patent No.: US 6,765,006 B2
(45) Date of Patent: Jul. 20, 2004

(54) SUBSTITUTED QUINAZOLINES AND ANALOGS AND THE USE THEREOF

(75) Inventors: Ravi Upasani, Sunnyvale, CA (US); Sui X. Cai, San Diego, CA (US)

(73) Assignee: Euro-Celtique S.A. (LU)

( * ) Notice: Subject to any disclaimer, the term of this patent is extended or adjusted under 35 U.S.C. 154(b) by 0 days.

(21) Appl. No.: 10/219,755

(22) Filed: Aug. 16, 2002

(65) Prior Publication Data

US 2003/0033089 A1 Feb. 13, 2003

Related U.S. Application Data

(62) Division of application No. 09/654,839, filed on Sep. 1, 2001, now Pat. No. 6,465,472, which is a continuation of application No. PCT/US99/04609, filed on Mar. 2, 1999.
(60) Provisional application No. 60/076,451, filed on Mar. 2, 1998.

(51) Int. Cl.$^7$ .................... C07D 237/26; C07D 239/70; C07D 49/04; C07D 49/056; A61K 31/50

(52) U.S. Cl. .................... 514/232.8; 544/250; 544/115; 514/267

(58) Field of Search .............................. 544/250, 115; 514/267, 232.8

(56) References Cited

U.S. PATENT DOCUMENTS

| 3,748,331 A | 7/1973 | Cooke et al. ......... 260/251 QB |
| 3,759,920 A | 9/1973 | Linder et al. .............. 424/251 |
| 3,856,960 A | 12/1974 | Cooke et al. ......... 260/251 QB |
| 3,963,717 A | 6/1976 | Cooke et al. ......... 260/251 QB |
| 5,284,957 A | 2/1994 | Huff ........................... 548/112 |
| 5,514,680 A | 5/1996 | Weber et al. ............... 514/249 |
| 5,650,410 A | 7/1997 | Sohda et al. ............. 514/233.8 |

FOREIGN PATENT DOCUMENTS

| DE | 2 058 722 | 6/1971 |
| DE | 2 307 808 | 8/1973 |
| EP | 0 567 107 A1 | 10/1993 |
| EP | 0 634 169 A1 | 1/1995 |
| GB | 1341401 | 12/1973 |
| JP | S51-8287 | 1/1976 |
| WO | WO 94/13275 | 6/1993 |

OTHER PUBLICATIONS

English language translation of Japanese Unexamined Patent Application No. JP S51-8287 published Jan. 23, 1976, 7 pages. (Document AM2).
Yamamoto, M., et al., "Quinazolin-2-ones from 3,4-dihydroquinazolin-2-ones," *Chem. Abstr.* 84:586, Abstract No. 180277m, American Chemical Society (1976).
Supplementary Partial European Search Report for European Application No. EP 99 911063 filed on Mar. 2, 1999.

Woodward, R.M. et al., "In Vitro Pharmacology of ACEA–1021 and ACEA–1031: Systemically Active Quinoxalinediones with High Affinity and Selectivity for N–Methyl–D–aspartate Receptor Glycine Sites," *Mol. Pharmacol.* 47:568–581, American Society for Pharmacology and Experimental Therapeutics (1995).
Wrathall, J.R. et al., "Amelioration of Functional Deficits from Spinal Cord Trauma with Systemically Administered NBQX, an Antagonist of Non–N–Methyl–D–Aspartate receptors," *Exp. Neurology* 137:119–126, Academic Press (1996).
Sheardown, M.J. et al., "AMPA, but not NMDA, receptor antagonism is neuroprotective in gerbil global ischaemia, even when delayed 24 h," *Eur. J. Pharmacol.* 236:347–353, Elsevier Science (1993).
Staubli, U. et al., "Facilitation of glutamate receptors enhances memory," *Proc. Natl. Acad. Sci. USA* 91:777–781, National Academy of Sciences (1994).
Thomas, R.J., "Excitatory Amino Acids in Health and Disease," *J. Am. Geriatr. Soc.* 43:1279–1289, Blackwell Science (1995).
Sang, C.N. et al., "Analgesic Effects of AMPA/Kainate Antagonist LY293558 in Human: Reduction of Capsaicin–Evoked Allodynia and Hyperalgesia But Not Pain Sensations In Normal Skin," *Soc. Neuroci* 23:1015, Abstract No. 401.14, Society of Neuroscience (Oct. 1997).
Schoepp, D. et al., "Pharmacological and functional characteristics of metabotropic excitatory amino acid receptors," *Trends Pharm Sci* 11:508–515, Elsevier in Association with the International Union of Pharmacology (1990).
Sheardown, M.J. et al., "2,3–Dihydroxy–6–nitro–7–sulfamoyl–benzo (F) quinoxalin: A Neuroprotectant for Cerebral Ischemia," *Science* 247:571–574, American Association for the Advancement of Science (1990).

(List continued on next page.)

*Primary Examiner*—John M. Ford
*Assistant Examiner*—Hong Liu
(74) *Attorney, Agent, or Firm*—Sterne, Kessler, Goldstein & Fox, P.L.L.C.

(57) ABSTRACT

The invention relates to novel quinazolines and heterocycles which are antagonists or positive modulators of AMPA receptors, and the use thereof for treating, preventing or ameliorating neuronal loss associated with stroke, global and focal ischemia, CNS trauma, hypoglycemia and surgery, as well as treating or ameliorating neurodegenerative diseases including Alzheimer's disease, amyotrophic lateral sclerosis, Huntington's disease, Parkinson's disease and Down's syndrome, treating, preventing or ameliorating the adverse consequences of the overstimulation of the excitatory amino acids, treating, preventing or ameliorating anxiety, psychosis, convulsions, chronic pain, glaucoma, retinitis, urinary incontinence, muscular spasm and inducing anesthesia, as well as for treating or ameliorating the adverse consequences of excitatory amino acid deficiency such as schizophrenia, myoclonus, Alzheimer's disease and malnutrition and neural maldevelopment, and as cognition and learning enhancers.

11 Claims, No Drawings

OTHER PUBLICATIONS

Lipton, S. and P.A. Rosenberg, "Excitatory Amino Acids as a Final Common Pathway for Neurologic Disorders," *N. Engl. J. Med.* 330:613–622, Massachusetts Medical Society (1994).

McDonald,, J.W. et al., "Physiological and pathophysiological roles of excitatory amino acids during central nervous system development," *Brain Res. Rev.* 15:41–70, Elsevier Science (1990).

Pelletier, J.C. et al., "Substituted 1,2–Dihydrophthalazines: Potent, Selective, and Noncompetitive Inhibitors of the AMPA Receptor," *J. Med. Chem.* 39:343–346, American Chemical Society (1996).

Keana, J.F.W. et al., "Synthesis and Structure–Activity Relationships of Substituted 1,4–Dihydroquinoxaline–2,3–diones: Antagonists of N–Methyl–D–aspartate (NMDA) Receptor Glycine Sites and Non–NMDA Gluatamate Receptors," *J. Med. Chem.* 38:4367–4379, American Chemical Society (1995).

Larson, J. et al., "Effects of an AMPA receptor modulator on methamphetamine–induced hyperactivity in rats," *Brain Res.* 738:353–356, Elsevier/North–Holland Biomedical Press (1996).

Le Peillet, E. et al., "The non–NMDA antagonists, NBQX and GYKI 52466, protect against cortical and striatal cell loss following transient global ischaemia in the rat," *Brain Res.* 571:115–120, Elsevier/North–Holland Biomedical Press (1992).

Ikeda, A. et al., "Clinical Trial of Piracetam in Patients with Myoclonus: Nationwide Multiinstitution Study in Japan," *Movement Disorders* 11:691–700, Raven Press (1996).

Iwasaki, Y. et al., "CNQX prevents spinal motor neuron death following sciatic nerve transection in newborn rats," *J. Neurosci.* 134:21–25, Society for Neuroscience (1995).

Jones, B.J. et al., "The potential anxiolytic activity of GR38032F, a 5–HT$_3$–receptor antagonist," *Br. J. Pharmacol.* 93:985–993, Macmillan Journals Ltd. (1988).

Haider, N., "Convenient Synthesis of Cycloalkene–Fused Phthalazinones," *Heterocycles* 41:2519–2525, Sendai Institute of Heterocyclic Chemistry (1995).

Houlihan, W.J. et al., "Antiinflammatory Properties of 8–Aryl–5–isopropyl–2H–1,3–dioxolo[4,5–g]quinazolin–6(5H)–ones and –thiones," *J. Med. Chem.* 25:1110–1113, American Chemical Society (1982).

Hunter, J.C. and L. Singh, "Role of excitatory amino acid receptors in the mediation of the nociceptive response to formalin in the rat," *Neurosci Lett.* 174:217–221, Elsevier Scientific Publishers (1994).

De Sarro, G. et al., "GYKI 52466 and related 2,3–benzodiazepines as anticonvulsant agents in DBA/2 mice," *Eur. J. Pharmacol.* 294:411–422, Elsevier Science (1995).

Fetter, J. et al., "Electron Deficient Heteroaromatic Ammonioamidates–XVI," *Tetrahedron* 34:2557–2563, Pergammon Press (1978).

Graham, S.H. et al., "A Dose–Response Study of Neuroprotection Using the AMPA Antagonist NBQX in Rat Focal Cerebral Ischemia," *J. Pharm. Exp. Ther.* 276:1–4, American Society for Pharmacology and Experimental Therapeutics (1996).

Choi, D.W. et al., "Glutamate Neurotoxicity in Cortical Cell Culture," *J. Neurosci* 7:357–368, Society for Neuroscience (1987).

Coombs, R.V. et al., "Synthesis and Antiinflammatory Activity of 1–Alkyl–4–aryl–2(1H)–quinazolinones and Quinazolinethiones," *J. Med. Chem.* 16:1237–1245, American Chemical Society (1973).

Copani, A. et al., "Nootropic Drugs Positively Modulate α–Amino–3–Hydroxy–5–Methyl–4–Isoxazolepropionic Acid–Sensitive Glutamate Receptors in Neuronal Cultures," *J. Neurochem.* 58:1199–1204, The International Society for Neurochemistry (1992).

Anderson, B.A. et al., "Application of a Practical Biocatalytic Reduction to an Enantioselective Synthesis of the 5H–2,3–Benzodiazepine LY300164," *J. Am. Chem. Soc.* 117:12358–12359, American Chemical Society (1995).

Buchan, A.M. et al., "Delayed AMPA receptor blockade reduces cerebral infarction induced by focal ischemia," *Neuroreport* 2:473–476, Lippincott, Williams & Wilkins (1991).

Buchan, A.M. et al., "AMPA Antagonists: Do They Hold More Promise for Clinical Stroke Trials Than NMDA Antagonists?" *Stroke Suppl. I* 24:I–148–I–154, Lippincott, Williams & Wilkins (1993).

Dialog File 351, Accession No. 1973–41080U/197329, Derwent WPI English language abstract for DE 2307808.

SUBSTITUTED QUINAZOLINES AND ANALOGS AND THE USE THEREOF

This application is a divisional application of U.S. application Ser. No. 09/654,839, filed on Sep. 1, 2001, now U.S. Pat. No. 6,465,472, which is a continuation of International Application PCT/US99/04609 published under PCT Article 21(2) in English, with an International Filing Date of Mar. 2, 1999, which claims priority from U.S. Provisional Application No. 60/076,451, filed Mar. 2, 1998, now abandoned, the entirety of all being fully incorporated by reference herein.

FIELD OF THE INVENTION

This invention is in the field of medicinal chemistry. In particular, the invention is related to novel substituted quinazolines and analogs thereof. These compounds are antagonists of x-amino-3-hydroxy-5-methylisoxazole-4-propionic acid (AMPA) ionotropic receptors. Certain of these compounds are positive modulators of AMPA receptors. The invention also is directed to the use of novel substituted quinazolines and analogs thereof for the treatment of neuronal damage following global and focal ischemia, and for the treatment or prevention of neurodegenerative conditions, as anticonvulsants, as cognitive enhancers, and for the treatment of schizophrenia, Parkinson's disease and myoclonus. The compounds of the invention are also useful for treatment or prevention of pain, including acute and chronic pain. The invention also is directed to a process for the preparation of the substituted quinazolines and analogs thereof.

RELATED ART

Excitatory amino acid receptors are classified into two general types. Receptors that are directly coupled to the opening of cation channels in the cell membrane of the neurons are termed "ionotropic." This type of receptor has been subdivided into at least three subtypes, which are defined by the depolarizing actions of the selective agonist N-methyl-D-aspartate (NMDA), α-amino-3-hydroxy-5-methylisoxazole-4-propionic acid (AMPA), and kainic acid (KA). The second general type is the G-protein or second messenger-linked "metabotropic" excitatory amino acid receptor. This second type, when activated by the agonists quisqualate, ibotenate, or trans-1-aminocyclopentane-1,3-dicarboxylic acid, leads to enhanced phosphoinositide hydrolysis in the postsynaptic cell. Both types of receptors appear not only to mediate normal synaptic connections during development, but also change in the efficiency of synaptic transmission throughout life. (Schoepp, Bockaert, and Sladeczek, *Trends Pharm. Sci.* 11:508 (1990); McDonald and Johnson, *Brain Res. Rev.* 15:41 (1990)). The excessive or inappropriate stimulation of excitatory amino acid receptors leads to neuronal cell damage or loss by a mechanism known as excitotoxicity. The medical consequences of such neuronal degeneration makes the abatement of these degenerative neurological processes an important therapeutic goal. (See U.S. Pat. No. 5,284,957).

Antagonists of the AMPA receptor are considered useful in treating, preventing and ameliorating a number of neurologic disorders which are due to overstimulation by the excitatory amino acids. These include acute neurologic disorders such as domoic acid poisoning; cerebral ischemia, global ischemia associated with cardiac arrest; stroke; spinal cord trauma; hypoxia; anoxia; poisoning by carbon monoxide, manganese or cyanide; hypoglycemia; mechanical trauma to the nervous system; epileptic seizures; and chronic neurologic disorders such as Huntington's disease, neuronal injury associated with HIV and AIDS, AIDS dementia, neuropathic pain syndrome, olivopontocerebral atrophy, Parkinson's disease, amyotrophic lateral sclerosis, mitochondrial abnormalities, Alzheimer's disease, hepatic encephalopathy, Tourette's syndrome, drug addiction and urinary incontinence (see Lipton and Rosenberg, *N. Engl. J. Med.* 330: 613–622 (1994)) and treatment or amelioration of a number of chronic neurologic disorders such as schizophrenia. AMPA receptor antagonists are also useful in treating, preventing and ameliorating acute and chronic pain, pain associated with post-therapeutic neurolgia, interstitial cystitis, osteoarthritis, spinal cord injury, cancer and diabetic neuropathy.

There is much evidence suggesting that the interaction of glutamate with membrane receptors plays a key role on many critical neurological functions such as cognition, learning and memory. Cognitive deficits likely arising from hypoactivity of glutamate receptors are known to be associated with neurodegenerative disorders such as Alzheimer's disease. Hypoactivity of glutamate receptors also might be associated with schizophrenia. One therapeutic approach is the direct stimulation of glutamate receptors with agonists. However, this approach increases the risk of excitotoxicity and may lead to further neurodegeneration. Selective positive modulation of certain glutamate receptor subtypes would be a better approach. Therefore positive modulators of AMPA receptors are expected to be useful for the treatment or amelioration of a number of chronic neurologic disorders such as schizophrenia, Alzheimer's disease and malnutrition and neural maldevelopment (Thomas, R. J., *J. Am. Geriatr. Soc.* 43. 1279–1289 (1995)). It has been shown that the AMPA receptor positive modulator BDP 1-(1,3-benzodioxol-5-ylcarbonyl)piperidine and its derivatives enhance memory in rat (Staubli et al., *Proc. Natl. Acad. Sci.* 91: 777–778 (1994)). The AMPA positive modulator BDP-29 also has been shown to attenuate the amount of stereotypic rearings seen in rats after methamphetamine injection, suggesting that AMPA receptor modulators might be useful for the treatment of schizophrenia (Larson et al. *Brain Res.* 738, 353–356 (1996)). Furthermore, piracetam, a well known nootropic agent which is used to treat cognitive impairment in the elderly, was found to be a positive modulator of AMPA receptors (Copani et al. *J. Neurochem.* 58: 1199–1204 (1992)). A recent clinical study showed that piracetam was effective in treating patients with myoclonus, especially that of cortical origin (Ikeda et al. *Movement Disorders* 11: 691–700 (1996)). Thus, AMPA receptor positive modulators are useful in treating myoclonus.

Recent studies have shown that AMPA receptor antagonists are neuroprotective in focal and global ischemia models. The competitive AMPA receptor antagonist NBQX (2,3-dihydroxy-6-nitro-7-sulfamoylbenzo[f]quinoxaline) has been reported to be effective in preventing global and focal ischemic damage. (Sheardown et al., *Science* 247:571 (1990); Buchan et al., *Neuroreport.* 2:473 (1991); Lepeillet et al., *Brain Res.* 571:115 (1992)). The noncompetitive AMPA receptor antagonist GKYI 52466 (1-(4-aminophenyl)-4-methyl-7,8-methylenedioxy-5H-2,3-benzodiazepine-hydrochloride) has been shown to be an effective neuroprotective agent in rat global ischemia models. (Lapeillet et al., *Brain Res.* 571:115 (1992)). GYKI 52466 has also been shown to be an effective anticonvulsant (DeSarro et al., *Eur. J. Pharmacol.* 294:411 (1995)).

These studies strongly suggest that the delayed neuronal degeneration in brain ischemia involves glutamate excitotoxicity mediated at least in part by AMPA receptor activation. Thus, AMPA receptor antagonists are useful as neuroprotective agents and improve the neurological outcome of cerebral ischemia in animals. (See U.S. Pat. No. 5,284,957).

Hunter and Singh reported that 2,3-dihydroxy-6-nitro-7-sulfamoylbenzo[f]quinoxaline (NBQX), a prototypical AMPA receptor antagonist, is active in blocking animal model of acute pain (*Neurosci. Lett.* 174(2): 217–221 (1994)).

Sang et al., reported recently that (3S,4aR,6R,8aR)-6-[2-(1(2)H-tetrazole-5-yl)ethyl]decahydroisoquinoline-3-carboxylic acid (LY2935586) was effective in blocking the sensitization in the spinal neuron that mediates capsaicin-evoked allodymia and hyperalgesia in human, (*Soc. Neurosci.* Abstract #401.14, 1997) a human model of chronic pain.

Anderson et. al., (*J. Am. Chem. Soc.* 117.12358–12359 (1995)) reported the synthesis of 5-H-2,3-benzodiazepine (LY3300164) shown below. The compound is said to be a noncompetitive antagonist of AMPA receptors with anticonvulsant activity.

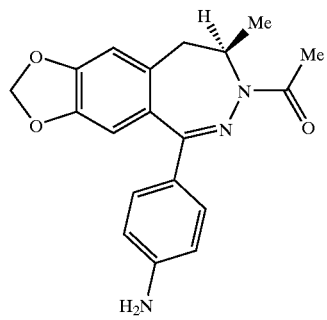

Pelletier el. al. (*J. Med. Chem.* 39: 343–346 (1996)) reported recently substituted 1,2-dihydrophthalazines as noncompetitive inhibitors of the AMPA receptor. For example, the compound shown below is said to be active as an anticonvulsant in the maximal electroshock model.

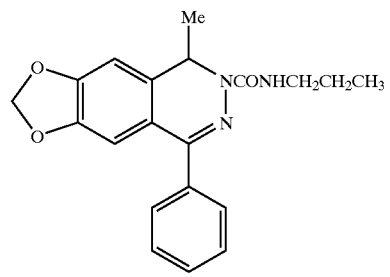

A group of 1-alkyl-4-aryl-2(1H)-quinazolinones and quinazolinethiones were reported to have antiinflammatory activity (*J. Med. Chem.* 16: 1237–1245 (1973)).

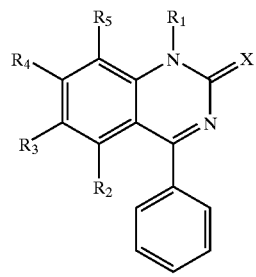

Where $R_1$ is H and alkyls such as Me, Et, i-Pr; $R_2$–$R_5$ are independently H, Me or OMe, and X is O or S.

A group of 4-aryl-1-isopropyl-1,3-dioxolo[4,5-g]quinazolin-2(1H)-ones and thiones as shown below were reported to have antiinflammatory activity (*J. Med. Chem.* 25: 1110–1113 (1982)).

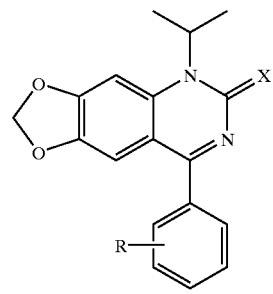

where X=O or S, R=3-F, 4-Me, 3-OMe, 2-$NO_2$ and other substitutents

SUMMARY OF THE INVENTION

This invention is related to novel AMPA antagonists represented by Formulae I–III.

Formula I

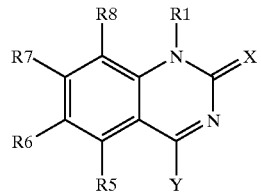

Formula II

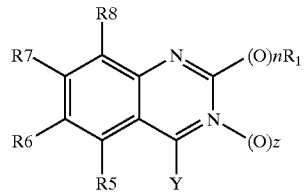

Formula III

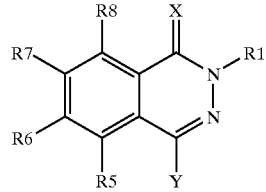

or a pharmaceutically acceptable salt or prodrug thereof, wherein:

R₁ is alkyl, haloalkyl, aminoalkyl, alkenyl, alkynyl, aralkyl, aralkenyl, aralkynyl, heteroaralkyl, carbocycloalkyl, heterocycloalkyl, hydroxyalkyl, cyanoalkyl, alkanoylamidoalkyl, alkanoyloxyalkyl, azidoalkyl, alkenyloxyalkyl, or alkoxyalkyl;

R₆ and R₇ taken together to form a five or six membered carbocyclic or heterocyclic ring including —OCH₂O—, —OCH₂CH₂O—, —O—CF₂—O—, —CH₂CH₂CH₂—, —CH₂CH₂CH₂CH₂—, —OCH₂CH₂— or —N(R,)—CO—O—; R₉ is optionally substituted lower alkyl;

R₅ and R₈ are independently selected from the group consisting of hydrogen, halogen, haloalkyl, aryl, heterocyclic, heteroaryl, alkyl, alkenyl, alkynyl, aralkyl, aralkenyl, aralkynyl, hydroxyalkyl, nitro, amino, cyano, alkanoylamido, hydroxy, thiol, alkanoyloxy, alkoxy, carboxy, carbonylamido or thioalkoxy;

X=O or S;

Y is aryl or heteroaryl, including for example

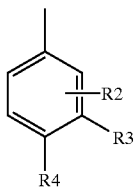

wherein R₂ is H, alkyl, halo, amino, alkoxy, or nitro;

R₃ and R₄ taken together to form a five or six membered carbocyclic or heterocyclic ring including —OCH₂O—, —OCH₂CH₂O—, —O—CF₂—O—, —CH₂CH₂CH₂—, —CH₂CH₂CH₂CH₂—, O—CH₂CH₂—, —N=CH—O—. —NH—CO—O—, CH=CH—CH=CH—, or O—CH=CH—;

n is 0 or 1; and z is 0 or 1.

Certain of the compounds of the present invention may exist as optical isomers, and the invention includes both the racemic mixtures of such optical isomers as well as the individual enantiomers.

Examples of pharmaceutically acceptable addition salts include inorganic and organic acid addition salts such as hydrochloride, hydrobromide, phosphate, sulphate, citrate, lactate, tartrate, maleate, fumarate, mandelate and oxalate.

The invention relates to the discovery that certain of the novel compounds represented by formula I are antagonists of AMPA receptors. Therefore the invention is related to a method of treating, preventing or ameliorating neuronal loss associated with stroke, global and focal ischemia, CNS trauma, hypoglycemia and surgery, spinal cord trauma, neuronal damage associated with cardiac arrest; as well as treating or ameliorating neurodegenerative diseases including Alzheimer's disease, amyotrophic lateral sclerosis, Huntington's disease, Parkinson's disease and Down's syndrome; treating, preventing or ameliorating the adverse consequences of the overstimulation of the excitatory amino acids; treating, preventing or ameliorating anxiety, convulsions, acute and chronic pain, migraine headache, muscle spasm and inducing anesthesia; as well as treating or ameliorating glaucoma and retinitis and preventing opiate tolerance, comprising administering to an animal in need of such treatment an effective amount of the AMPA receptor antagonists of the present invention, or a pharmaceutically acceptable salt or prodrug thereof.

Thus the invention is directed to the novel AMPA receptor modulators as defined in Formulae I–III.

The invention is also directed to methods employing the novel AMPA receptor modulators of Formulae I–III as antagonists of AMPA receptors.

The invention is also directed to a pharmaceutical composition comprising an effective amount of the AMPA receptor antagonists for the treatment of neurodegenerative conditions, acute and chronic pain and as anticonvulsants.

The invention is also directed to method for treating, preventing or ameliorating neuronal damage following global and focal ischemia; and treating, preventing or ameliorating neurodegenerative conditions and convulsions. The invention is also directed to the treatment, prevention or amelioration of acute and chronic pain. In addition, the invention is directed to a method for cognition enhancement and the treatment, prevention or amelioration of schizophrenia.

The invention is also directed to novel methods for the preparation of the novel AMPA receptor modulators as defined in Formulae I–III.

DETAILED DESCRIPTION OF THE INVENTION

The novel AMPA antagonists modulators are represented by previously defined Formulae (I–III). Preferred structures of the novel compounds are represented by Formulae IV–VIII. In particular, a preferred embodiment is represented by Formulae IV:

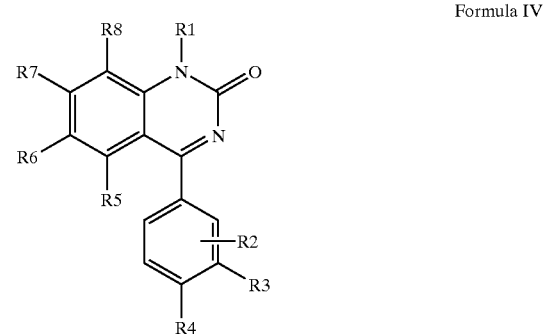

Formula IV or a pharmaceutically acceptable salt or prodrug thereof wherein R₁–R₈ are as defined previously with respect to Formula I.

Another preferred embodiment is represented by Formula V:

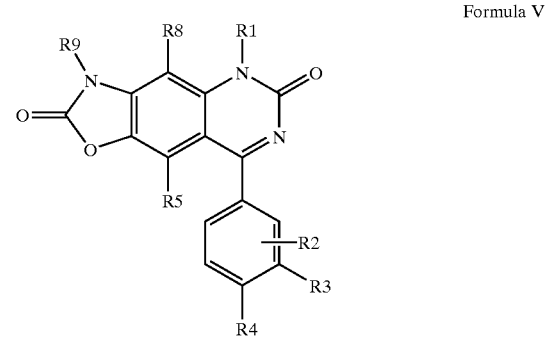

Formula V or a pharmaceutically acceptable salt or prodrug thereof wherein R₁–R₅ and R₈–R₉ are as defined previously with respect to Formula I;

Yet another preferred embodiment is represented by Formulae VI:

Formula VI or a pharmaceutically acceptable salt or prodrug thereof wherein R$_1$–R$_8$ and z are as defined previously with respect to Formula II.

Yet another preferred embodiment is represented by Formula VII:

Formula VII or a pharmaceutically acceptable salt or prodrug thereof wherein R$_1$–R$_8$ and z are as defined previously with respect to Formula II.

Yet another preferred embodiment is represented by Formula VIII:

Formula VIII or a pharmaceutically acceptable salt or prodrug thereof wherein R$_1$–R$_8$ are as defined previously with respect to Formula III.

Preferred Y groups are carbocyclic, heterocyclic, aryl, heteroaryl groups, and bicyclic fused heterocyclic, aryl or heteroaryl groups, each of which may be independently substituted by hydrogen, halo, haloalkyl, aryl, a fused carbocyclic group, a fused heterocyclic group, a carbocyclic group, a heterocyclic group, a heteroaryl group, C$_{1-10}$ alkyl, alkenyl, alkynyl, aralkyl, aralkenyl, aralkynyl, heteroaralkyl, heteroaralkenyl, heteroaralkynyl, carbocycloalkyl, heterocycloalkyl, hydroxyalkyl, nitro, amino, cyano, acylamido, hydroxy, thiol, alkanoyloxy, azido, alkoxy, carboxy, or alkylthio groups.

With respect to the formulae above:

Typical C$_{6-14}$ aryl groups include phenyl, naphthyl, phenanthryl, anthracyl, indenyl, azulenyl, biphenyl, biphenylenyl and fluorenyl groups.

Typical carbocyclic groups include cyclopropyl, cyclobutyl, cyclopentyl, cyclohexyl and cycloheptyl.

Typical halo groups include fluorine, chlorine, bromine and iodine.

Typical C$_{1-10}$ alkyl groups include methyl, ethyl, propyl, isopropyl, butyl, sec-butyl, tert-butyl, 3-pentyl, hexyl and octyl groups. Also contemplated is a trimethylene group substituted on two adjoining positions on the benzene ring of the compounds of the invention.

Typical C$_{2-4}$ alkenyl groups include ethenyl, propenyl, isopropenyl, butenyl, and sec-butenyl.

Typical C$_{2-4}$ alkynyl groups include ethynyl, propynyl, butynyl, and 2-butynyl groups.

Typical aralkyl groups include any of the above-mentioned C$_{1-10}$ alkyl groups substituted by any of the above-mentioned C$_{6-14}$ aryl groups.

Typical aralkenyl groups include any of the above-mentioned C alkenyl groups substituted by any of the above-mentioned C$_{6-14}$ aryl groups.

Typical aralkynyl groups include any of the above-mentioned C$_{2-4}$ alkynyl groups substituted by any of the above-mentioned C$_{6-14}$ aryl groups.

Typical carbocycloalkyl groups include any of the above-mentioned C$_{1-10}$ alkyl groups substituted by any of the above-mentioned carbocyclic groups.

Typical haloalkyl groups include C$_{1-10}$ alkyl groups substituted by one or more fluorine, chlorine, bromine or iodine atoms, e.g. fluoromethyl, difluoromethyl, trifluoromethyl, pentafluoroethyl, 1,1-difluoroethyl and trichloromethyl groups.

Typical hydroxyalkyl groups include C$_{1-10}$ alkyl groups substituted by hydroxy, e.g. hydroxymethyl, hydroxyethyl, hydroxypropyl and hydroxybutyl groups.

Typical alkoxy groups include oxygen substituted by one of the C$_{1-10}$ alkyl groups mentioned above.

Typical alkylthio groups include sulphur substituted by one of the C$_{1-10}$ alkyl groups mentioned above.

Typical alkanoylamino groups include any C$_{1-6}$alkanoyl substituted on nitrogen, e.g. acetamido, propionamido, butanoylamido, pentanoylamido, hexanoylamido as well as aryl-substituted C$_{2-6}$ substituted acyl groups.

Typical alkanoyloxy groups include any C$_{1-6}$ acyloxy groups, e.g. acetoxy, propionoyloxy, butanoyloxy, pentanoyloxy, hexanoyloxy and the like.

Typical heterocyclic groups include tetrahydrofuranyl, pyranyl, A piperidinyl, piperazinyl, pyrrolidinyl, imidazolindinyl, imidazolinyl, indolinyl, isoindolinyl, quinuclidinyl, morpholinyl, isochromanyl, chromanyl, pyrazolidinyl, 1,3-benzodioxolyl, 1,4-benzodioxanyl and pyrazolinyl groups.

Typical heterocycloalkyl groups include any of the above-mentioned C$_{1-10}$ alkyl groups substituted by any of the above-mentioned heterocyclic groups.

Typical heteroaryl groups include any one of the following which may be optionally substituted with one or more C$_{1-10}$ alkyl, halo, or hydroxy groups: thienyl, benzo[b]thienyl, naphtho[2,3-b]thienyl, thianthrenyl, furyl, pyranyl, isobenzofuranyl, chromenyl, xanthenyl, phenoxanthiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinozalinyl, cinnolinyl, pteridinyl, 5aH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl phenoxazinyl groups, 1,4-dihydroquinoxaline-2,3-dione, 7-aminoisocoumarin, pyrido [1,2-a]pyrimidin-4-one, 1,2-benzoisoxazol-3-yl, 4-nitrobenzofurazan, benzimidazolyl, 2-oxindolyl and 2-oxobenzimidazolyl. Where the heteroaryl group contains a nitrogen atom in a ring, such nitrogen atom may be in the form of an N-oxide, e.g. a pyridyl N-oxide, pyrazinyl N-oxide, pyrimidinyl N-oxide and the like.

Typical heteroaralkyl groups include any of the above-mentioned $C_{1-10}$ alkyl groups substituted by any of the above-mentioned heteroaryl groups.

Typical heteroaralkenyl groups include any of the above-mentioned $C_{2-4}$ alkenyl groups substituted by any of the above-mentioned heteroaryl groups.

Typical heteroaralkynyl groups include any of the above-mentioned $C_{2-4}$ alkynyl groups substituted by any of the above-mentioned heteroaryl groups.

Typical amino groups include —$NH_2$, —$NHR_{20}$ and —$NR_2OR_{21}$ wherein $R_{20}$ and $R_{21}$ are independently $C_{1-10}$ alkyl groups as defined above.

Typical carbonylamido groups are carbonyl groups substituted by $NH_2$, —$NHR_{20}$, and —$NR_2OR_{21}$ groups as defined above.

When the group is an amidino or guinidino group, any one of the nitrogen atoms may be substituted independently by hydrogen, $C_{1-10}$ alkyl or aryl groups.

Optional substituents on the aryl, aralkyl, aryloxy, arylthioxy, aroyl, heterocyclic, heterocycloxy, heteroaryl, heteroaryloxy, cycloalkyl, and cycloalkoxy groups listed above include any one of the typical halo, haloalkyl, aryl, fused heterocyclic, fused carbocyclic, heterocyclic, heteroaryl, $C_{1-10}$ alkyl, alkenyl, alkynyl, aralkyl, aralkenyl, aralkynyl, heteroaralkyl, heteroaralkenyl, heteroaralkynyl, carbocycloalkyl, heterocycloalkyl, hydroxyalkyl, nitro, amino, cyano, alkanoylamido, hydroxy, thiol, acyloxy, azido, alkoxy, carboxy, carbonylamido, and alkylthiol groups mentioned above.

Preferred groups for $R_1$ are $C_{1-10}$ alkyl, haloalkyl, a carbocyclic group, a heterocyclic group, alkenyl, alkynyl, carbocycloalkyl, heterocycloalkyl, hydroxyalkyl and aminoalkyl. Preferred groups for Y are substituted and unsubstituted heterocyclic, carbocyclic, heteroaryl and aryl. Most preferred groups for $R_2$ are substituted and unsubstituted fused bicyclic heterocyclic, carbocyclic, heteroaryl and aryl.

Exemplary preferred compounds of Formulae I–III include, without limitation:

4-phenyl-cyclopento[g]quinazolin-2(1H)-one,
1-ethyl-4-phenyl-cyclopento[g]quinazolin-2(1H)-one,
6,7-ethylenedioxy-4-phenylquinazolin-2(1H)-one,
6,7-ethylenedioxy-1-isopropyl-4-phenylquinazolin-2(1H)-one,
6,7-ethylenedioxy-1-ethyl-4-phenylquinazolin-2(1H)-one,
1-methyl-6,7-methylenedioxy-4-phenylquinazolin-2(1H)-one,
1-ethyl-6,7-methylenedioxy-4-phenylquinazolin-2(1H)-one,
1-isopropyl-6,7-methylenedioxy-4-phenylquinazolin-2(1H)-one,
1-benzyl-6,7-methylenedioxy-4-phenylquinazolin-2(1H)-one,
1-ethyl-6,7-methylenedioxy-4-(4-methoxyphenyl)quinazolin-2(1H)-one,
1-ethyl-6,7-methylenedioxy-4-(4-methylphenyl)quinazolin-2(1H)-one,
1-ethyl-4-(4-fluorophenyl)-6,7-methylenedioxyquinazolin-2(1H)-one,
4-(3-aminophenyl)-1-ethyl-6,7-methylenedioxyquinazolin-2(1H)-one,
4-(4-aminophenyl)-1-isopropyl-6,7-methylenedioxyquinazolin-2(1H)-one,
1-ethyl-4-(4-hydroxyphenyl)-6,7-methylenedioxyquinazolin-2(1H)-one,
1-ethyl-6,7-methylenedioxy-4-(3,4-methylenedioxyphenyl)quinazolin-2(1H)-one,
1-ethyl-4-(3,4-ethylenedioxyphenyl)-6,7-methylenedioxyquinazolin-2(1H)-one,
1-ethyl-6,7-methylenedioxy-4-(4,5-methylenedioxy-2-nitrophenyl)quinazolin-2(1H)-one,
4-(2-amino-4,5-methylenedioxyphenyl)-1-ethyl-6,7-methylenedioxyquinazolin-2(1H)-one,
1-ethyl-6,7-methylenedioxy-4-(3,4-dimethoxyphenyl)quinazolin-2(1H)-one,
1-isopropyl-6,7-methylenedioxy-4-(3,4-methylenedioxyphenyl)quinazolin-2(1H)-one,
4-(3,4-ethylenedioxyphenyl)-1-isopropyl-6,7-methylenedioxyquinazolin-2(1H)-one,
1-ethyl-6,7-methylenedioxy-4-(2-naphthyl)quinazolin-2(1H)-one,
1-(3-pentyl)-6,7-methylenedioxy-4-(3,4-methylenedioxyphenyl)quinazolin-2(1H)-one,
1-isopropyl-6,7-methylenedioxy-4-(2-naphthyl)quinazolin-2(1H)-one,
1-cyclopropylmethyl-6,7-methylenedioxy-4-(3,4-methylenedioxyphenyl)quinazolin-2(1H)-one,
1-(2-diethylaminoethyl)-6,7-methylenedioxy-4-(3,4-methylenedioxyphenyl)quinazolin-2(1H)-one,
1-(2-propynyl)-6,7-methylenedioxy-4-(3,4-methylenedioxyphenyl)quinazolin-2(1H)-one,
1-isopropyl-6,7-methylenedioxy-4-(4-dimethylaminophenyl)quinazolin-2(1H)-one,
1-isopropyl-6,7-(difluoromethylenedioxy)-4-(3,4-methylenedioxyphenyl)quinazolin-2(1H)-one,
1-isopropyl-6,7-ethylenedioxy-4-(3,4-methylenedioxyphenyl)quinazolin-2(1H)-one,
1-(2-dimethylaminoethyl)-6,7-methylenedioxy-4-(3,4-methylenedioxyphenyl)quinazolin-2(1H)-one,
1-isopropyl-6,7-methylenedioxy-4-(2,3-dihydro-5-benzopuranyl)quinazolin-2(1H)-one,
1-isopropyl-6,7-methylenedioxy-4-(6-chloro-3,4-methylenedioxyphenyl)quinazolin-2(1H)-one,
1-isopropyl-6,7-methylenedioxy-4-(5-indanyl)quinazolin-2(1H)-one,
1-(2-morpholinoethyl)-6,7-methylenedioxy-4-(3,4-methylenedioxyphenyl)quinazolin-2(1H)-one,
1-isopropyl-6,7-methylenedioxy-4-(3,4-difluoromethylenedioxyphenyl)quinazolin-2(1H)-one,
1-(1-methyl-2-dimethylaminoethyl)-6,7-methylenedioxy-4-(3,4-methylenedioxyphenyl)quinazolin-2(1H)-one,
1-isopropyl-6,7-methylenedioxy-4-(3-quinolinyl)quinazolin-2(1H)-one,
1-(2-aminoethyl)-6,7-methylenedioxy-4-(3,4-methylenedioxyphenyl)quinazolin-2(1H)-one,
1-isopropyl-6,7-methylenedioxy-4-(5-benzoxazolyl)quinazolin-2(1H)-one,
1-isopropyl-4-(3,4-methylenedioxyphenyl)-8-methyl-7-oxo-oxazol[5,4-g]quinazolin-2(1H)-one,
1-(2-pyrrolidinoethyl)-6,7-methylenedioxy-4-(3,4-methylenedioxyphenyl)quinazolin-2(1H)-one,
2-(2-diethylaminoethoxy)-6,7-methylenedioxy-4-(3,4-methylenedioxyphenyl)quinazoline, 2-methyl-6,7-methylenedioxy-4-(3,4-methylenedioxyphenyl)quinazoline,
2-(1-hydroxy-1-methyl)ethyl-6,7-methylenedioxy-4-(3,4-methylenedioxyphenyl)quinazoline,
6,7-methylenedioxy-4-(3,4-methylenedioxyphenyl)quinazoline,
2-ethyl-6,7-methylenedioxy-4-(3,4-methylenedioxyphenyl)quinazoline,
2-benzyl-6,7-methylenedioxy-4-(3,4-methylenedioxyphenyl)quinazoline,
2-(2-dimethylaminoethoxy)-6,7-methylenedioxy-4-(3,4-methylenedioxyphenyl)quinazoline,
2-dimethylamino-6,7-methylenedioxy-4-(3,4-methylenedioxyphenyl)quinazoline,
2-(2-diethylaminoethyl)-6,7-methylenedioxy-4-(3,4-methylenedioxyphenyl)quinazoline,
2-(2-chloroethyl)-6,7-methylenedioxy-4-(3,4-methylenedioxyphenyl)quinazoline,
2-(2-dimethylaminomethyl)-6,7-methylenedioxy-4-(3,4-methylenedioxyphenyl)quinazoline,
2-chloromethyl-6,7-methylenedioxy-4-(3,4-methylenedioxyphenyl)quinazoline,
2-(2-dimethylamino-1-methylethoxy)-6,7-methylenedioxy-4-(3,4-methylenedioxyphenyl)quinazoline,
2-(3-chloropropyl)-6,7-methylenedioxy-4-(3,4-methylenedioxyphenyl)quinazoline,
2-(2-aminoethoxy)-6,7-methylenedioxy-4-(3,4-methylenedioxyphenyl)quinazoline,
2-(3-aminopropyl)-6,7-methylenedioxy-4-(3,4-methylenedioxyphenyl)quinazoline,
2-n-pentyl-6,7-methylenedioxy-4-(3,4-methylenedioxyphenyl)quinazoline,
6,7-methylenedioxy-4-(3,4-methylenedioxyphenyl)-3-(N-oxide)-quinazoline,
2-(imidazol-1-yl)methyl-6,7-methylenedioxy-4-(3,4-methylenedioxyphenyl)quinazoline,
6,7-methylenedioxy-4-(3,4-methylenedioxyphenyl)-2-(1,2,4-triazol-1-yl)methyl-quinazoline,
2-((1-methyl-2-imidazolyl)thio)methyl-6,7-methylenedioxy-4-(3,4-methylenedioxyphenyl)quinazoline,
2-(imidazol-1-yl)ethyl-6,7-methylenedioxy-4-(3,4-methylenedioxyphenyl)quinazoline,
2-iodomethyl-6,7-methylenedioxy-4-(3,4-methylenedioxyphenyl)quinazoline,
2-acetoxymethyl-6,7-methylenedioxy-4-(3,4-methylenedioxyphenyl)quinazoline,
2-(2-morpholinoethyl)-6,7-methylenedioxy-4-(3,4-methylenedioxyphenyl)quinazoline,
2-piperazinomethyl-6,7-methylenedioxy-4-(3,4-methylenedioxyphenyl)quinazoline,
2-(2-pyrrolidinoethoxy)-6,7-methylenedioxy-4-(3,4-methylenedioxyphenyl)quinazoline,
1-(2-dimethylaminoethyl)-6,7-methylenedioxy-4-(3,4-ethylenedioxyphenyl)quinazolin-2(1H)-one,
1-Isopropyl-4-(3,4-methylenedioxyphenyl)-8-methyl-7-oxo-oxazol[5,4-g]quinazolin-2(1H)-one,
1-Isopropyl-4-(3,4-methylenedioxyphenyl)-8-benzyl-7-oxo-oxazol[5,4-g]quinazolin-2(1H)-one,
1-Isopropyl-4-(3,4-methylenedioxyphenyl)-8-ethyl-7-oxo-oxazol[5,4-g]quinazolin-2(1H)-one,
1-Isopropyl-4-(2-naphthyl)-8-ethyl-7-oxo-oxazol[5,4-g]quinazolin-2(1H)-one,
1-Isopropyl-4-(3,4-methylenedioxyphenyl)-8-propyl-7-oxo-oxazol [5,4-g]quinazolin-2(1H)-one,
1-Isopropyl-4-(3,4-methylenedioxyphenyl)-7-oxo-oxazol[5,4-g]quinazolin-2(1H)-one,
6,7-methylenedioxy-4-(3,4-methylenedioxyphenyl)quinazoline 3-oxide,
2-Chloromethyl-6,7-methylenedioxy-4-(3,4-methylenedioxyphenyl)quinazoline 3-oxide,
2-Ethyl-6,7-methylenedioxy-4-(3,4-methylenedioxyphenyl)quinazoline 3-oxide,
2-Methyl-6,7-methylenedioxy-4-(3,4-methylenedioxyphenyl)quinazoline 3-oxide,
2-(1-Imidazolyl)methyl-6,7-methylenedioxy-4-(3,4-methylenedioxyphenyl)quinazoline 3-oxide,
6,7-methylenedioxy-4-(3,4-methylenedioxyphenyl)-2-(1-pyrrolidinyl)methylquinazoline 3-oxide,
2-Dimethylaminomethyl-4-(3,4-methylenedioxyphenyl)-6,7-methylenedioxyquinazoline-3-oxide,
2-Methylaminomethyl-4-(3,4-methylenedioxyphenyl)-6,7-methylenedioxyquinazoline 3-oxide,
2-[2-(Dimethylamino)ethyl]-4-(3,4-methylenedioxyphenyl)-6.7-methylenedioxy-1(2H)-phthalazinone,
2-ethyl-4-(3,4-methylenedioxyphenyl)-6,7-methylenedioxy-1(2H)-phthalazinone,
2-[2-(1-Imidazolyl)ethyl]-4-(3,4-methylenedioxyphenyl)-6,7-methylenedioxy-1 (2H)-phthalazinone,
4-(3,4-Methylenedioxyphenyl)-6,7-methylenedioxy-1(2H)-phthalazinone,
2-[2-(1-Piperidinyl)ethyl]-4-(3,4-methylenedioxyphenyl)-6,7-methylenedioxy-1(2H)-phthalazinone,
2-[2-(1-Pyrrolidinyl)ethyl]-4-(3,4-methylenedioxyphenyl)-6,7-methylenedioxy-1 (2H)-phthalazinone, and
2-[2-(ethoxycarbonyl)ethyl]-4-(3,4-methylenedioxyphenyl)-6,7-methylenedioxy-1(2H)-phthalazinone.

The compounds of the present invention may exist as optical isomers and the invention includes both the racemic mixtures of such optical isomers as well as the individual enantiomers that may be separated according to methods that are well known to those of ordinary skill in the art.

Examples of pharmaceutically acceptable addition salts include inorganic and organic acid addition salts such as hydrochloride, hydrobromide, phosphate, sulphate, citrate, lactate, tartrate, maleate, fumarate, mandelate and oxalate.

Examples of prodrugs include esters or amides of Formulae I–III where $R_1$–$R_4$ is hydroxyalkyl or aminoalkyl, which may be obtained by reacting such compounds with an anhydride such as acetic anhydride, propionyl anhydride, succinic anhydride and the like.

The invention is also directed to a method for treating disorders responsive to the blockade of AMPA receptors in animals suffering thereof. Particular Preferred embodiments of compounds for use in method of this invention are represented by previously defined Formulae I–III. Exemplary preferred compounds that may be employed in this method of invention include, without limitation:

6,7-methylenedioxy-4-phenylquinazolin-2(1H)-one,
4-phenyl-cyclopento[g]quinazolin-2(1H)-one,
1-isopropyl-4-phenyl-cyclopento[g]quinazolin-2(1H)-one,
1-ethyl-4-phenyl-cyclopento[g]quinazolin-2(1H)-one,
6,7-ethylenedioxy-4-phenylquinazolin-2(1H)-one,
6,7-ethylenedioxy-1-isopropyl-4-phenylquinazolin-2(1H)-one,
6,7-ethylenedioxy-1-ethyl-4-phenylquinazolin-2(1H)-one,
1-methyl-6,7-methylenedioxy-4-phenylquinazolin-2(1H)-one,
1-ethyl-6,7-methylenedioxy-4-phenylquinazolin-2(1H)-one. 1-isopropyl-6,7-methylenedioxy-4-phenylquinazolin-2(1H)-one, 1-benzyl-6,7-methylenedioxy-4-phenylquinazolin-2(1H)-one,
1-ethyl-6,7-methylenedioxy-4-(4-methoxyphenyl)quinazolin-2(1H)-one,
1-ethyl-6,7-methylenedioxy-4-(4-methylphenyl)quinazolin-2(1H)-one,
1-ethyl-4-(4-fluorophenyl)-6,7-methylenedioxyquinazolin-2(1H)-one,
4-(3-aminophenyl)-1-ethyl-6,7-methylenedioxyquinazolin-2(1H)-one,
4-(4-aminophenyl)-1-isopropyl-6,7-methylenedioxyquinazolin-2(1H)-one,
1-ethyl-4-(4-hydroxyphenyl)-6,7-methylenedioxyquinazolin-2(1H)-one,
1-ethyl-6,7-methylenedioxy-4-(3,4-methylenedioxyphenyl)quinazolin-2(1H)-one,
1-ethyl-4-(3,4-ethylenedioxyphenyl)-6,7-methylenedioxyquinazolin-2(1H)-one,
1-ethyl-6,7-methylenedioxy-4-(4,5-methylenedioxy-2-nitrophenyl)quinazolin-2(1H)-one,
4-(2-amino-4,5-methylenedioxyphenyl)-1-ethyl-6,7-methylenedioxyquinazolin-2(1H)-one,
1-ethyl-6,7-methylenedioxy-4-(3,4-dimethoxyphenyl)quinazolin-2(1H)-one,
1-isopropyl-6,7-methylenedioxy-4-(3,4-methylenedioxyphenyl)quinazolin-2(1H)-one,
4-(3,4-ethylenedioxyphenyl)-1-isopropyl-6,7-methylenedioxyquinazolin-2(1H)-one,
1-ethyl-6,7-methylenedioxy-4-(2-naphthyl)quinazolin-2(1H)-one,
1-(3-pentyl)-6,7-methylenedioxy-4-(3,4-methylenedioxyphenyl)quinazolin-2(1H)-one,
1-isopropyl-6,7-methylenedioxy-4-(2-naphthyl)quinazolin-2(1H)-one,
1-cyclopropylmethyl-6,7-methylenedioxy-4-(3,4-methylenedioxyphenyl)quinazolin-2(1H)-one,
1-(2-diethylaminoethyl)-6,7-methylenedioxy-4-(3,4-methylenedioxyphenyl)quinazolin-2(1H)-one,
1-(2-propynyl)-6,7-methylenedioxy-4-(3,4-methylenedioxyphenyl)quinazolin-2(1H)-one,
1-isopropyl-6,7-methylenedioxy-4-(4-dimethylaminophenyl)quinazolin-2(1H)-one,
1-isopropyl-6,7-(difluoromethylenedioxy)-4-(3,4-methylenedioxyphenyl)quinazolin-2(1H)-one,
1-isopropyl-6,7-ethylenedioxy-4-(3,4-methylenedioxyphenyl)quinazolin-2(1H)-one,
1-(2-dimethylaminoethyl)-6,7-methylenedioxy-4-(3,4-methylenedioxyphenyl)quinazolin-2(1H)-one,
1-isopropyl-6,7-methylenedioxy-4-(2,3-dihydro-5-benzopuranyl)quinazolin-2(1H)-one,
1-isopropyl-6,7-methylenedioxy-4-(6-chloro-3,4-methylenedioxyphenyl)quinazolin-2(1H)-one,
1-isopropyl-6,7-methylenedioxy-4-(5-indanyl)quinazolin-2(1 1H)-one,
1-(2-morpholinoethyl)-6,7-methylenedioxy-4-(3,4-methylenedioxyphenyl)quinazolin-2(1H)-one,
1-isopropyl-6,7-methylenedioxy-4-(3,4-difluoromethylenedioxyphenyl)quinazolin-2(1H)-one,
1-(1-methyl-2-dimethylaminoethyl)-6,7-methylenedioxy-4-(3,4-methylenedioxyphenyl)quinazolin-2(1H)-one,
1-isopropyl-6,7-methylenedioxy-4-(3-quinolinyl)quinazolin-2(1H)-one,
(2-aminoethyl)-6,7-methylenedioxy-4-(3,4-methylenedioxyphenyl)quinazolin-2(1H)-one,
1-isopropyl-6,7-methylenedioxy-4-(5-benzoxazolyl)quinazolin-2(1H)-one,
1-isopropyl-4-(3,4-methylenedioxyphenyl)-8-methyl-7-oxo-oxazol[5,4-g]quinazolin-2(1H)-one,
1-(2-pyrrolidinoethyl)-6,7-methylenedioxy-4-(3,4-methylenedioxyphenyl)quinazolin-2(1H)-one,
2-(2-diethylaminoethoxy)-6,7-methylenedioxy-4-(3,4-methylenedioxyphenyl)quinazoline,
2-methyl-6,7-methylenedioxy-4-(3,4-methylenedioxyphenyl)quinazoline,
2-(1-hydroxy-1-methyl)ethyl-6,7-methylenedioxy-4-(3,4-methylenedioxyphenyl)quinazoline,
6,7-methylenedioxy-4-(3,4-methylenedioxyphenyl)quinazoline. 2-ethyl-6,7-methylenedioxy-4-(3,4-methylenedioxyphenyl)quinazoline,
2-benzyl-6,7-methylenedioxy-4-(3,4-methylenedioxyphenyl)quinazoline,
2-(2-dimethylaminoethoxy)-6,7-methylenedioxy-4-(3,4-methylenedioxyphenyl)quinazoline,
2-dimethylamino-6,7-methylenedioxy-4-(3,4-methylenedioxyphenyl)quinazoline,
2-(2-diethylaminoethyl)-6,7-methylenedioxy-4-(3,4-methylenedioxyphenyl)quinazoline,
2-(2-chloroethyl)-6,7-methylenedioxy-4-(3,4-methylenedioxyphenyl)quinazoline,
2-(2-dimethylaminomethyl)-6,7-methylenedioxy-4-(3,4-methylenedioxyphenyl)quinazoline,
2-chloromethyl-6,7-methylenedioxy-4-(3,4-methylenedioxyphenyl)quinazoline,
2-(2-dimethylamino-1-methylethoxy)-6,7-methylenedioxy-4-(3,4-methylenedioxyphenyl)quinazoline,
2-(3-chloropropyl)-6,7-methylenedioxy-4-(3,4-methylenedioxyphenyl)quinazoline,
2-(2-aminoethoxy)-6,7-methylenedioxy-4-(3,4-methylenedioxyphenyl)quinazoline,
2-(3-aminopropyl)-6,7-methylenedioxy-4-(3,4-methylenedioxyphenyl)quinazoline,
2-n-pentyl-6,7-methylenedioxy-4-(3,4-methylenedioxyphenyl)quinazoline,
6,7-methylenedioxy-4-(3,4-methylenedioxyphenyl)-3-(N-oxide)-quinazoline,
2-(imidazol-1-yl)methyl-6,7-methylenedioxy-4-(3,4-methylenedioxyphenyl)quinazoline,
6,7-methylenedioxy-4-(3,4-methylenedioxyphenyl)-2-(1,2,4-triazol-1-yl)methyl-quinazoline,
2-((1-methyl-2-imidazolyl)thio)methyl-6,7-methylenedioxy-4-(3,4-methylenedioxyphenyl)quinazoline,
2-(imidazol-1-yl)ethyl-6,7-methylenedioxy-4-(3,4-methylenedioxyphenyl)quinazoline,
2-iodomethyl-6,7-methylenedioxy-4-(3,4-methylenedioxyphenyl)quinazoline,
2-acetoxymethyl-6,7-methylenedioxy-4-(3,4-methylenedioxyphenyl)quinazoline,
2-(2-morpholinoethyl)-6,7-methylenedioxy-4-(3,4-methylenedioxyphenyl)quinazoline,
2-piperazinomethyl-6,7-methylenedioxy-4-(3,4-methylenedioxyphenyl)quinazoline,
2-(2-pyrrolidinoethoxy)-6,7-methylenedioxy-4-(3,4-methylenedioxyphenyl)quinazoline,
1-(2-dimethylaminoethyl)-6,7-methylenedioxy-4-(3,4-ethylenedioxyphenyl)quinazolin-2(1H)-one,
1-Isopropyl-4-(3,4-methylenedioxyphenyl)-8-methyl-7-oxo-oxazol[5,4-g quinazolin-2(1H)-one,
1-Isopropyl-4-(3,4-methylenedioxyphenyl)-8-benzyl-7-oxo-oxazol[5,4-g]quinazolin-2(1H)-one,
1-Isopropyl-4-(3,4-methylenedioxyphenyl)-8-ethyl-7-oxo-oxazol[5,4-g]quinazolin-2(1H)-one,
1-Isopropyl-4-(2-naphthyl)-8-ethyl-7-oxo-oxazol[5,4-g]quinazolin-2(1H)-one,
1-Isopropyl-4-(3,4-methylenedioxyphenyl)-8-propyl-7-oxo-oxazol[5,4-g]quinazolin-2(1H)-one, 1-Isopropyl-4-(3,4-methylenedioxyphenyl)-7-oxo-oxazol[5,4-g]quinazolin-2(1H)-one,
6,7-methylenedioxy-4-(3,4-methylenedioxyphenyl)quinazoline 3-oxide,
2-Chloromethyl-6,7-methylenedioxy-4-(3,4-methylenedioxyphenyl)quinazoline 3-oxide,
2-Ethyl-6,7-methylenedioxy-4-(3,4-methylenedioxyphenyl)quinazoline 3-oxide,
2-Methyl-6,7-methylenedioxy-4-(3,4-methylenedioxyphenyl)quinazoline 3-oxide,
2-(1-Imidazolyl)methyl-6,7-methylenedioxy-4-(3,4-methylenedioxyphenyl)quinazoline 3-oxide,
6,7-methylenedioxy-4-(3,4-methylenedioxyphenyl)-2-(1-pyrrolidinyl)methylquinazoline 3-oxide,
2-Dimethylaminomethyl-4-(3,4-methylenedioxyphenyl)-6,7-methylenedioxyquinazoline-3-oxide,
2-Methylaminomethyl-4-(3,4-methylenedioxyphenyl)-6,7-methylenedioxyquinazoline 3-oxide,
2-[2-(Dimethylamino)ethyl]-4-(3,4-methylenedioxyphenyl)-6,7-methylenedioxy-1(2H)-phthalazinone,
2-ethyl-4-(3,4-methylenedioxyphenyl)-6,7-methylenedioxy-1(2H)-phthalazinone,
2-[2-(1-Imidazolyl)ethyl]-4-(3,4-methylenedioxyphenyl)-6,7-methylenedioxy-1 (2H)-phthalazinone,
4-(3,4-Methylenedioxyphenyl)-6,7-methylenedioxy-1(2H)-phthalazinone,
2-[2-(1-Piperidinyl)ethyl]-4-(3,4-methylenedioxyphenyl)-6,7-methylenedioxy-1 (2H)-phthalazinone,
2-[2-(1-Pyrrolidinyl)ethyl]-4-(3,4-methylenedioxyphenyl)-6,7-methylenedioxy-1(2H)-phthalazinone, and
2-[2-(ethoxycarbonyl)ethyl]-4-(3,4-methylenedioxyphenyl)-6,7-methylenedioxy-1(2H)-phthalazinone.

The compounds of this invention may be prepared using methods well known to those skilled in the art, or by the novel methods of this invention. Specifically, compounds with Formula I can be prepared as illustrated by exemplary reactions in Scheme 1.

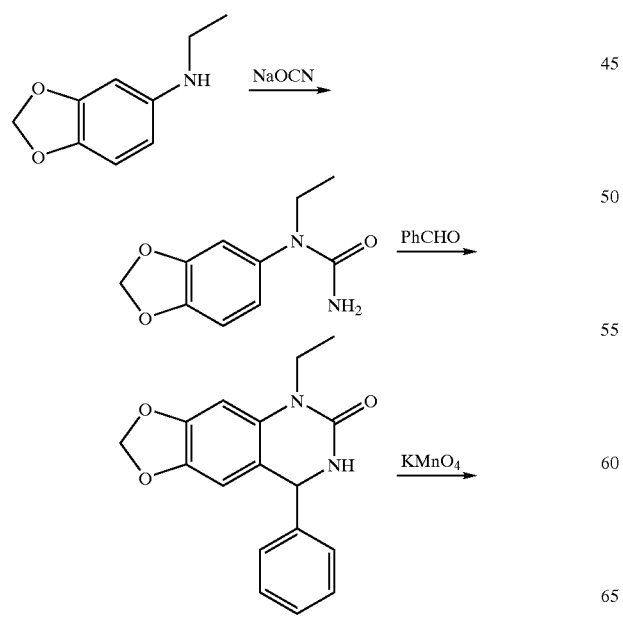

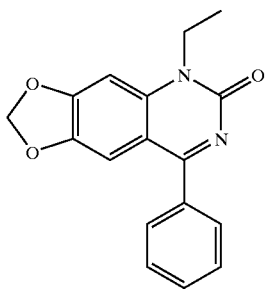

Compounds with Formula I (X=S) can be prepared as illustrated by exemplary reactions in Scheme 2.

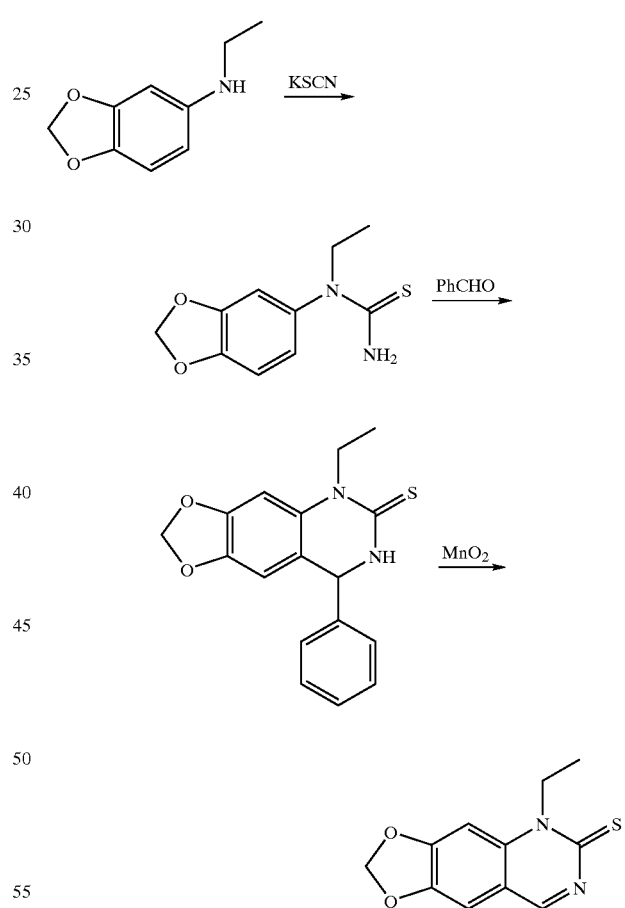

Compounds with Formula II can be prepared as illustrated by exemplary reactions in Scheme 3.

Scheme 3

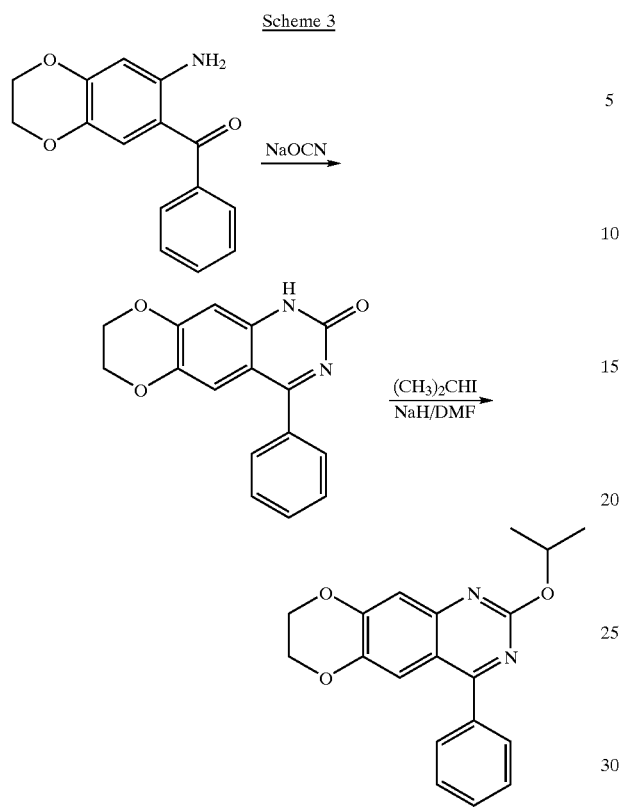

Compounds with Formula I and II (R$_1$ is dimethylaminoethyl) can be prepared as illustrated by exemplary reactions in Scheme 4.

Scheme 4

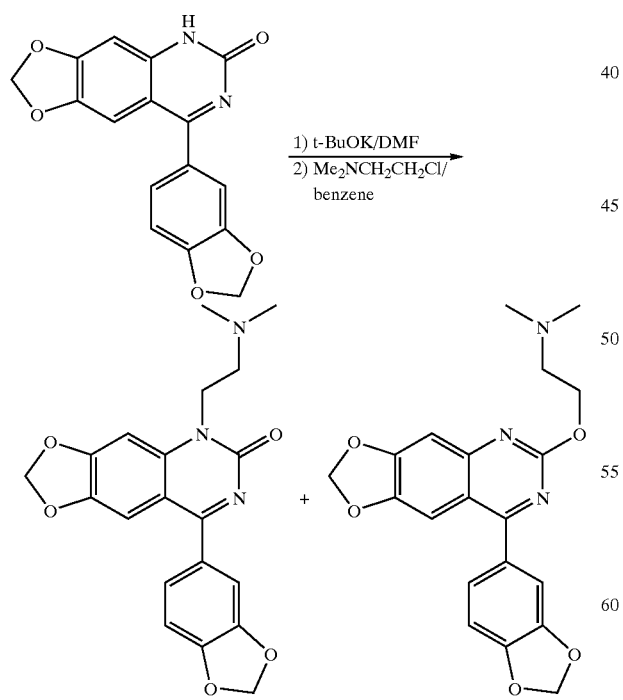

Alternatively, compounds with Formula II (R$_1$=alkyl; n=z=0) can be prepared as illustrated by exemplary reactions in Scheme 5.

Scheme 5

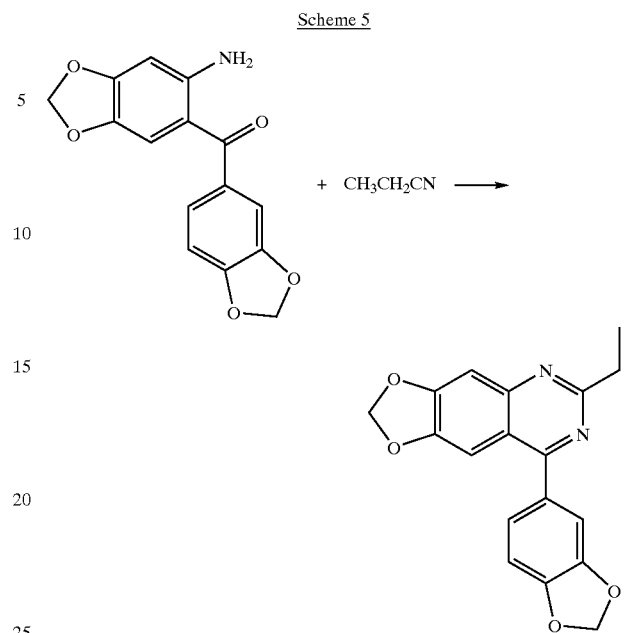

Compounds with Formula II (z=1) can be prepared as illustrated by exemplary reactions in Scheme 6.

Scheme 6

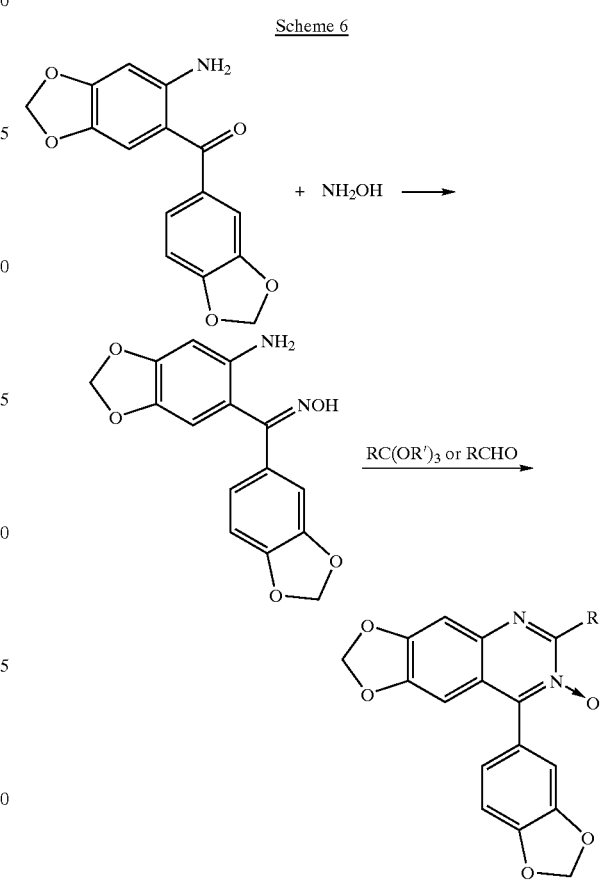

Compounds with Formula III (z=1) can be prepared as illustrated b-exemplary reactions in Scheme 7.

Scheme 7

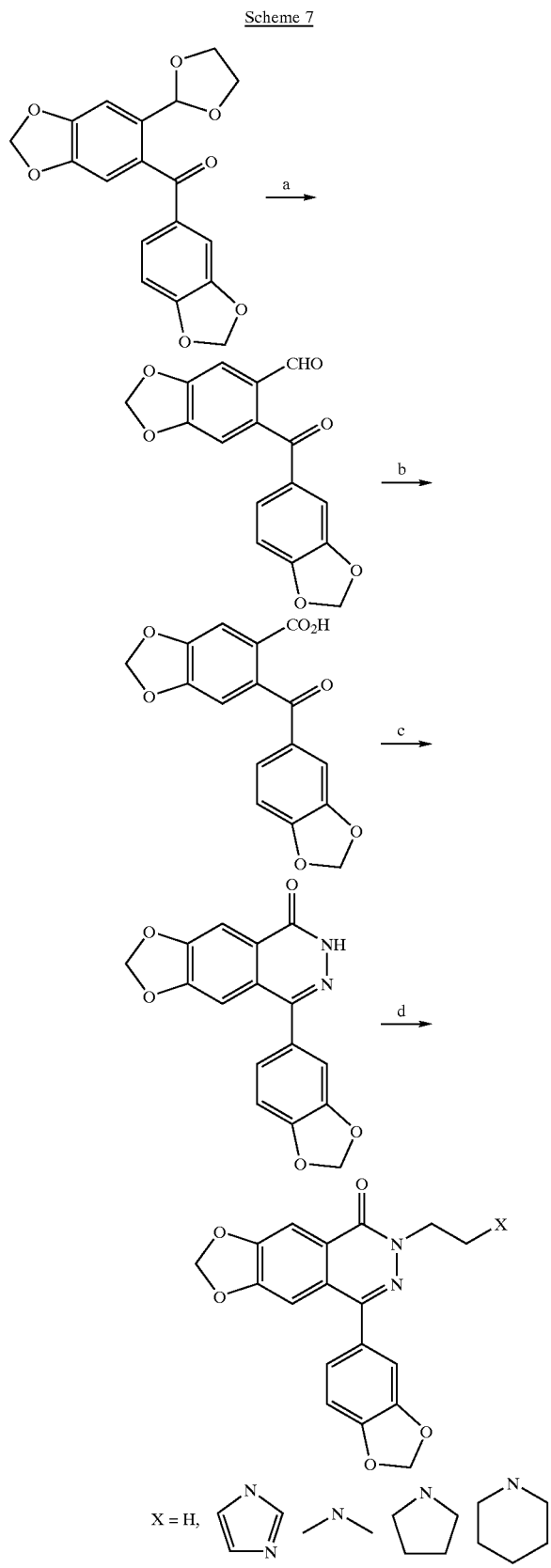

(a) PPTS, Acetone, H₂O, reflux, 77%; (b) n-Bu₄, Py, 54%;
(c) H₂NNH₂H₂O, EtOH reflux, 70%; (d)

K$_2$CO$_3$, DMF, 80° C., 91%; 16%; 81%; 91%; 55% (e) ethyl bromoacetate, K$_2$CO$_3$, DMF, 80° C., 60%

The compounds of the present invention may be assessed by electrophysiological assays in Xenopus oocytes expressing rat whole brain poly(A)$^+$ RNA (see Keana et. al. *J. Med. Chem.* 38: 4367–4379 (1995)) or in cultured rat cortical neurons (see Woodward et. al. *Mol. Pharmacol.* 47: 568–581 (1995)) for AMPA receptor activity. Compounds which are useful for treating or preventing the adverse consequences of stroke, hypoglycemia, neurodegenerative disorders, anxiety, epilepsy or psychosis, or which induce analgesia, will inhibit the currents across the membranes of the oocyte expressing AMPA receptors. However, if the compound potentiates currents across the oocyte membrane, then the compound is expected to be useful in enhancing cognition or treating schizophrenia or neurodegenerative disease such as Parkinson's Disease.

The compounds of the present invention are active in treating, preventing or ameliorating neuronal loss, neurodegenerative diseases, acute and chronic pain, are active as anticonvulsants and inducing anesthesia. They are also useful for treating or ameliorating epilepsy and psychosis.

Neurodegenerative diseases which may be treated or ameliorated with the compounds of the present invention include those selected from the group consisting of Alzheimer's disease, amyotrophic lateral sclerosis, Huntington's disease, Parkinson's disease and Down's syndrome.

The compounds of the present invention find particular utility in the treatment of global and focal ischemia or prevention of neuronal loss associated with multiple strokes which give rise to dementia. After a patient has a cardiac arrest, the compounds of the present invention may be administered to ameliorate the ischemia related neuronal damage that may occur from cardiac arrest and other causes of global ischemia.

The compounds of the invention find particular utility in treating, preventing or ameliorating the adverse neurological consequences of surgery. For example, coronary bypass surgery requires the use of heart-lung machines which tend to introduce air bubbles into the circulatory system which may lodge in the brain. The presence of such air bubbles robs neuronal tissue of oxygen, resulting in anoxia and ischemia. Pre- or post-surgical administration of the compounds of the present invention will treat or prevent the resulting ischemia. In a preferred embodiment, the compounds of the invention are administered to patients undergoing cardiopulmonary bypass surgery or carotid endarterectomy surgery.

The compounds of the present invention also find utility in treating, preventing or ameliorating acute and chronic pain. Such acute and chronic pain may be the result of surgery, trauma, headache, diabetes, arthritis, pain from terminal cancer or degenerative diseases. The compounds of the present invention also find particular utility in the treatment of phantom pain that results from amputation of an extremity. In addition to treatment of pain, the compounds of the invention are also expected to be useful in treating muscle spasm and inducing anesthesia, either general or local anesthesia, for example, during surgery.

The compounds of the present invention may be tested for in vivo anticonvulsant activity after iv or ip injection using a number of anticonvulsant tests in mice (audiogenic seizure model in DBA-2 mice, pentylenetetrazol-induced seizures in mice, maximum electroshock seizure test (MES)).

The compounds may be tested for their neuroprotective activity after focal and global ischemia produced in rats or gerbils according to the procedures described in Buchan et. al. (Stroke, Suppl. 148–152 (1993)), Sheardown et. al. (*Eur. J. Pharmacol.* 236:347–353 (1993)), and Graham et. al. (*J. Pharmacol. Exp. Therap.* 276:1–4 (1996)).

The compounds may be tested for their neuroprotective activity after traumatic spinal cord injury according to the procedures described in Wrathall et. al. (*Exp. Neurology* 137: 119–126 (1996)) and Iwasaki et. al. (*J. Neuro Sci.* 134:21–25 (1995)).

The compounds may also be tested in drug discrimination tests in rats trained to discriminate PCP from saline. It is expected that most of the compounds of the present invention will not generalize to PCP at any doses. In addition, it is also expected that none of the compounds will produce a behavioral excitation in locomotor activity tests in the mouse.

Elevated levels of glutamate have been associated with glaucoma. In addition, it has been disclosed that glaucoma management, particularly protection of retinal ganglion cells, can be achieved by administering to a patient a compound capable of reducing glutamate-induced excitotoxicity in a concentration effective to reduce the excitotoxicity. See WO94/13275. Thus, the compounds of the present invention, which are expected to cross the blood-retina barrier, are also expected to be useful in the treatment or amelioration of glaucoma. Preferably, the invention is directed to the treatment of patients which have primary open-angle glaucoma, chronic closed-angle glaucoma, pseudoexfoliation, or other types of glaucoma or ocular hypertension. Preferably, the compound is administered over an extended period (e.g. at least six months and preferably at least one year), regardless of the changes in the patient's intraocular pressure over the period of administration.

The compounds of the present invention show potent activity in vivo after intraperitoneal injection suggesting that these compounds can penetrate the blood/brain barrier and are systemically bioavailable.

Thus, the present invention is directed to substituted quinazolines and analogs having preferred binding to AMPA receptors. According to the present invention, those compounds having preferred binding to AMPA receptors exhibit an $IC_{50}$ of about 100 $\mu$M or less in the electrophysiological assay. Preferably, the compounds of the present invention exhibit an $IC_{50}$ of 10 $\mu$M or less. Most preferably, the compounds of the present invention exhibit an $IC_{50}$ of about 1.0 $\mu$M or less.

The efficacy of the AMPA antagonists to inhibit glutamate neurotoxicity in rat brain cortex neuron cell culture system may be determined according to Choi, D. W., *J. Neuroscience* 7:357 (1987).

The anticonvulsant activity of the AMPA antagonists may be evaluated in the Maximal Electroshock-induced Seizure (MES) test. Seizures are induced by application of current (50 mA, 60 pulses/sec, 0.8 sec pulse width, 1 sec duration, d.c.) through saline-coated corneal electrodes using a Ugo Basile ECT device (Model 7801). Mice are restrained by gripping the loose skin on their dorsal surface, electrodes were held lightly against the two cornea, then current was applied and mice were observed for a period of up to 30 sec for the occurrence of a tonic hindlimb extensor response. A tonic seizure is defined as a hindlimb extension in excess of 90 degrees from the plane of the body. Results are treated in a quintal manner.

The anticonvulsant efficacy of the AMPA antagonists may also be assessed in the pentylenetetrazol (PTZ)-induced seizure test according to U.S. Pat. No. 5,514,680.

It is known that AMPA receptors are critically involved in pain transmission and the development of persistent pain following nerve and tissue injury. The effects of the AMPA receptor antagonists of the present invention on pain may be evaluated according to U.S. Pat. No. 5,514,680. The compounds of the present invention are useful in treating headaches, in particular, migraine headaches.

The anxiolytic activity of any particular compound described herein may be determined by use of any of the recognized animal models for anxiety. A preferred model is described by Jones, B. J. et al., *Br. J. Pharmacol.* 93:985–993 (1988).

Compositions within the scope of this invention include all compositions wherein the compounds of the present invention are contained in an amount which is effective to achieve its intended purpose. While individual needs vary, determination of optimal ranges of effective amounts of each component is with the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for psychosis or anxiety disorders, e.g., generalized anxiety disorder, phobic disorders, obsessional compulsive disorder, panic disorder, and post traumatic stress disorders. Preferably, about 0.01 to about 10 mg/kg is orally administered to treat or prevent such disorders. For intramuscular injection, the dose is generally about one-half of the oral dose. For example, for treatment or prevention of anxiety, a suitable intramuscular dose would be about 0.0025 to about 15 mg/kg, and most preferably, from about 0.01 to about 10 mg/kg.

In the method of treatment or prevention of neuronal loss in global and focal ischemia, brain and spinal cord trauma, hypoxia, hypoglycemia, status epilepsy and surgery, the compound can be administered by intravenous injection at a dose of 0.025 to 10 mg/kg. For the treatment of AIDS associated neuronal damage, Alzheimer's disease, amyotrophic lateral sclerosis, Huntington's disease and Down's Syndrome, or in a method of treating a disease in which the pathophysiology of the disorder involves hyperactivity of the excitatory amino acids (e.g. convulsions) or AMPA receptor-ion channel related neurotoxicity, the pharmaceutical compositions of the invention may comprise the compounds of the present invention at a unit dose level of about 0.01 to about 50 mg/kg of body weight, or an equivalent amount of the pharmaceutically acceptable salt thereof, on a regimen of 1–4 times per day. When used to treat acute and chronic pain, to induce anesthesia, or to treat or prevent glaucoma, migraine headache, muscle spasm or urinary incontinence, the compounds of the invention may be administered at a unit dosage level of from about 0.01 to about 50 mg/kg of body weight, or an equivalent amount of the pharmaceutically acceptable salt thereof, on a regimen of 1–4 times per day. Of course, it is understood that the exact treatment level will depend upon the case history of the animal, e.g., human being, that is treated. The precise treatment level can be determined by one of ordinary skill in the art without undue experimentation.

The unit oral dose may comprise from about 0.01 to about 50 mg, preferably about 0.1 to about 10 mg of the compound. The unit dose may be administered one or more times daily as one or more tablets each containing from about 0.1 to about 10, conveniently about 0.25 to 50 mg of the compound or its solvates.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 0.25 to 75 percent of active compound(s), together with the excipient.

Also included within the scope of the present invention are the non-toxic pharmaceutically acceptable salts of the compounds of the present invention. Acid addition salts are formed by mixing a solution of the particular AMPA antagonist of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, and the like. Basic salts are formed by mixing a solution of the particular AMPA antagonist of the present invention with a solution of a pharmaceutically acceptable non-toxic base such as sodium hydroxide, potassium hydroxide, choline hydroxide, sodium carbonate and the like.

The pharmaceutical compositions of the invention may be administered to any animal which may experience the beneficial effects of the compounds of the invention. Foremost among such animals are mammals, e.g., humans, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol.

Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate, are used. Dye stuffs or pigments, may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions may contain substances which increase the viscosity of the suspension include, for example, sodium carboxymethyl cellulose, sorbitol, and/or dextran. Optionally, the suspension may also contain stabilizers.

The characterization of non-competitive AMPA receptors antagonists in vitro has been difficult because of the lack of selective drug ligands. Thus, the AMPA ligands of the present invention may be used to characterize the AMPA receptors and their distribution. Particularly preferred AMPA antagonists and positive modulator of the present invention which may be used for this purpose are isotopically radiolabelled derivatives. e.g. where one or more of the atoms are replaced with $^3H$, $^{11}C$, $^{14}C$, $^{15}N$, or $^{18}F$. Alternatively, a fluorescent group Y' may be employed. Examples of such groups include 4-nitrobenzofurazan.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLE 1

3,4-(Methylenedioxy)phenylurea and 3,4-(methylenedioxy)acetanilide

To a solution of 3,4-(methylenedioxy)aniline (15.2 g) in AcOH (200 mL) was added NaOCN (6.7 g) at 0° C. The cold bath was removed and the mixture was stirred at rt for 20 h. The solvent was removed in vacuo and the resulting residue was neutralized with 2 N NaOH. A broken solid precipitated out, which was collected by filtration, washed with water, dried in vacuo to yield 3,4-(methylenedioxy)phenylurea (11.4 g, 58%). The filtrate was extracted with CHCl$_3$ (3×100 mL). The combined organic phases were washed with water and dried over Na$_2$SO$_4$. The solvent was removed in vacuo to yield 3,4-(methylenedioxy)acetanilide (5.3 g, 27%). $^1$H NMR: 3.4-(methylenedioxy)phenylurea (DMSO-d$_6$), 8.48 (s, 1H), 7.17 (d, J=1.8, 1H), 6.76 (d, J=8.4, 1H), 6.67 (dd, J=1.8, 8.4, 1H), 5.93 (s, 2H), 5.78(s, 2H); 3.4-(methylenedioxy)acetanilide (CDCl$_3$), 9.83 (s, 1H), 7.29 (s, 1H), 6.94–6.81 (m, 2H), 5.96 (s, 2H), 3.34(s, 3H).

EXAMPLE 2

N-Isopropyl-3,4-(methylenedioxy)aniline

To a solution of 3,4-(methylenedioxy)aniline (9.0 g), and 9-iodopropane (5.9 mL) in methanol (100 mL) was added triethylamine (8.2 mL). The mixture was refluxed for 50 h, and then concentrated in vacuo. The residue was taken with 1:1 hexane/EtOAc (180 mL), washed with water and brine, dried over Na$_2$SO$_4$. The solvent was removed in vacuo and the residue was purified by chromatography (3:1 hexane/EtOAc) to yield the title compound as an oil (10.1 g, 85%). $^1$H NMR (CDCl$_3$): 6.64 (d, J=8.3, 1H), 6.23 (d, J=2.2, 1H), 6.03 (dd, J=2.2, 8.3, 1H), 5.85 (s, 2H), 3.51 (m, 1H), 3.19 (br s, 1H), 1.18 (d, J=6.1, 6H).

EXAMPLE 3

N-Methyl-3,4-(methylenedioxy)aniline

The title compound was prepared from 3,4-(methylenedioxy)aniline and iodomethane by the procedure described in example 2 in 18% yield. $^1$H NMR (CDCl$_3$): 6.67 (d, J=8.3, 1H), 6.25 (d, J=2.2, 1H), 6.04 (dd, J=2.2, 8.3, 1H), 5.85 (s, 2H), 3.50 (br s, 1H), 2.79 (s, 3H).

EXAMPLE 4

N-Methyl-N-[3,4-(methylenedioxy)phenyl]urea

The title compound was prepared from N-methyl-3,4-(methylenedioxy)aniline and NaOCN by the procedure described in example 1 in 56% yield. $^1$H NMR (CDCl$_3$): 6.75–6.64 (m, 3H), 6.02 (s, 2H), 4.42 (br s, 2H), 3.21(s, 3H).

EXAMPLE 5

N-Ethyl-N-[3,4-(methylenedioxy)phenyl]urea

To a solution of N-ethyl-3,4-(methylenedioxy)aniline (8.1 g) in AcOH (100 mL) was added NaOCN (3.0 g) at 10° C. The cold bath was removed and the mixture was stirred at rt for 24 h. The solvent was removed in vacuo and the resulting residue was neutralized with 2 N NaOH. The mixture was extracted with chloroform (3×50 mL). The combined organic phase was washed with water and brine, dried over Na$_2$SO$_4$. The solvent was removed in vacuo and the resulting residue was recrystallized from chloroform/hexane to yield the title compound (5.7 g, 56%). $^1$NMR (CDCl$_3$): 6.78–6.72 (m, 3H), 6.02 (s, 2H), 4.38 (br s, 2H), 3.66 (q, J=7.0, 2H), 1.11 (t, J=7.0, 3H).

EXAMPLE 6

N-Isopropyl-N-[3,4-(methylenedioxy)phenyl]urea

The title compound was prepared from N-isopropyl-3,4-(methylenedioxy)aniline and NaOCN by the procedure described in example 5 in 83% yield. $^1$H NMR (CDCl$_3$): 6.85-6.65 (m, 3H), 6.04 (s, 2H), 4.82 (m, 1H), 4.21 (br s, 2H), 1.06 (d, J=6.6, 6H).

EXAMPLE 7

2-Benzoyl-4,5-(methylenedioxy)acetanilide

To a solution of 3,4-(methylenedioxy)acetanilide (1.1 g) in CH$_2$Cl$_2$ (12 mL) was added SnCl$_4$ (1.0 M CH$_2$Cl$_2$ solution, 9.5 mL) at 0° C., followed by addition of PhCOCl (780 μL). The mixture was stirred at rt for 2 h, quenched with NaHCO$_3$, diluted with 1:1 hexane/EtOAc (80 mL), washed with water, 2 N HCl, water and brine, dried over Na$_2$SO$_4$. The solvent was removed in vacuo, and the residue was purified by chromatography (3:2 hexane/EtOAc) to yield the title compound as a yellow solid (380 mg, 22%). $^1$H NMR (CDCl$_3$): 11.45 (s, 1H), 8.30 (s, 1H), 7.65–7.46 (m, 5H), 6.88 (s, 1H), 6.98 (s, 1H), 6.03 (s, 2H), 2.23 (s, 3H).

EXAMPLE 8

2-Benzoyl-4,5-(methylenedioxy)aniline

To a solution of 2-benzoyl-4,5-(methylenedioxy)acetanilide (380 mg) in ethanol (20 mL) was added concentrated HCl (3.5 mL). The mixture was refluxed for 2 h, cooled to rt, poured onto ice, neutralized with 2 N NaOH and extracted with EtOAc (2×50 mL). The combined organic phase was dried over Na$_2$SO$_4$. The solvent was removed in vacuo to yield the title compound as a yellow solid (320 mg, 99%). $^1$H NMR (CDCl$_3$): 7.58–7.43 (m, 5H), 6.85 (s, 1H), 6.41 (br s, 2H), 6.23 (s, 1H), 5.90(s, 2H).

EXAMPLE 9

6,7-Methylenedioxy-4-phenylquinazolin-2(1H)-one

To a solution of 2-benzoyl-4,5-(methylenedioxy)aniline (200 mg) in AcOH (10 mL) was added water (1 mL) and NaOCN (64 mg) at 10° C. The mixture was stirred at 10° C. for 1 h, then at rt for 2 h. Water (70 mL) was added to the mixture. The resulting yellow solid was collected by filtration, washed with water and 3:2 hexane/EtOAc, recrystallized from DMSO/water to yield the title compound as a yellow solid (104 mg, 47%), mp: 351–354° C. $^1$H NMR (DMSO-d$_6$): 11.86 (s, 1H), 7.63–7.58 (m, 5H), 6.94 (s, 1H), 6.85 (s, 1H), 6.16 (s, 2H). Anal. calcd. for C$_{15}$H$_{10}$N$_2$O$_3$: C, 67.67; H, 3.79; N, 10.52. Found: C, 67.53; H, 3.76; N, 10.29.

EXAMPLE 10

1-Methyl-6,7-methylenedioxy-4-phenyl-3,4-dihydroquinazolin-2(1H)-one

A mixture of N-methyl-N-[3,4-(methylenedioxy)phenyl]urea (240 mg), benzaldehyde (140 μL) and methanesulfonic acid (50 μL) and toluene (60 mL) was refluxed for 2 h in a flask equipped with a Dean-Stark water separator. After cooling, the solution was washed with water thoroughly, dried over Na$_2$SO$_4$ and concentrated in vacuo. The resulting solid was recrystallized from chloroform/hexane to provided the title compound as a tan solid (70 mg, 20%), mp: 228–230° C. $^1$H NMR (CDCl$_3$): 7.37-7.30 (m, 5H), 6.53 (s, 1H), 6.28 (s, 1H), 5.91 (d, 1H, J=1.4), 5.89 (d, 1H, J=1.4), 5.46 (s, 1H), 5.11 (br s, 1H), 3.33 (s, 3H). Anal. calcd. for C$_{16}$H$_{14}$N$_2$O$_3$: C, 68.08: H, 5.00; N, 9.92. Found: C, 68.06; H, 4.91; N, 9.71.

EXAMPLE 11

1-Isopropyl-6,7-methylenedioxy-4-(3,4-methylenedioxyphenyl)-3,4-dihydroquinazolin-2(1H)-one The title compound was synthesized from N-isopropyl-N-[3.4-(methylenedioxy)phenyl]urea and piperonal by the procedure described in example 10 in 41% yield, mp: 87–89° C. $^1$H NMR (CDCl$_3$,): 6.77 (s, 3H), 6.68 (s, 1H), 6.28 (s, 1H), 5.96 (s, 2H), 5.92–5.90 (m, 2H), 5.22 (d, J=1.8, 1H), 4.98 (br s, 1H), 4.44 (m, 2H), 1.58–1.54 (m, 6H).

EXAMPLE 12

1-Methyl-6,7-methylenedioxy-4-phenylquinazolin-2 (1H)-one

To a solution of 1-methyl-6,7-methylenedioxy-4-phenyl-3,4-dihydroquinazolin-2(1H)-one (47 mg) in dioxane (3 mL) was added an aqueous solution of KMnO$_4$ (33 mg in 3 mL of water) at 10° C. After the addition, the mixture was extracted with EtOAc (3×10 mL). The organic phase was concentrated in vacuo. To the residue, water (70 mL) was added. The resulting solid was collected by filtration, washed with water, dried in vacuo to provide the title compound as a yellow solid (20 mg, 42%), mp: 253–255° C. $^1$H NMR (CDCl$_3$): 7.69-7.66 (m, 2H), 7.53–7.51 (m, 3H), 7.18 (s, 1H), 6.86 (s, 1H), 6.11 (s, 2H), 3.76 (s, 3H). Anal. calcd. for C$_{16}$H$_{12}$N$_2$O$_3$: C, 68.27; H, 4.32; N, 9.99. Found: C, 67.99; H, 4.17; N, 9.73.

EXAMPLE 13

1-Isopropyl-6,7-methylenedioxy-4-(3,4-methylenedioxyphenyl)quinazolin-2(1H)-one

The title compound was synthesized from 1-isopropyl-6,7-methylenedioxy-4-(3,4-methylenedioxyphenyl)-3,4-dihydroquinazolin-2(1H)-one by the procedure described in example 12 in 17% yield, mp: 125–127° C. $^1$H NMR (CDCl$_3$): 7.22-7.20 (m, 3H), 7.04 (s, 1H), 6.92 (d, J=8.3, 1H), 6.10 (s, 2H), 6.06 (s, 2H), 5.13 (m, 1H), 1.68 (d, J=7.1,66H).

EXAMPLE 14

5-Acetamidoindane

To a solution of 5-aminoindane (2.0 g, 15.0 mmol) in 5 mL of anhydrous pyridine at 0° C. was added acetic anhydride (2.1 mL, 22.5 mmol) and the solution was stirred at rt for 3 h. The solution was then added to 50 mL of water and the resulting solid filtered and washed with water, then dried under vacuum to yield the title compound (2.23 g, 78%). $^1$H NMR (CDCl$_3$): 7.44 (s, 1H), 7.2 (bs, 1H), 7.12 (s, 2H), 2.88 (q, 4H), 2.18 (s, 3H), 2.09 (p, 2H).

EXAMPLE 15

5-Acetamido-6-benzoylindane

To a solution of 5-acetamidoindane (1.0 g, 5.7 mmol) and benzoyl chloride (732 mL, 6.3 mmol) in 15 mL of CH$_2$Cl$_2$ at 0° C. was added AlCl$_3$ (1.52 g, 11.4 mmol) as a solid. The mixture was stirred to rt overnight. A spatula full of AlCl$_3$ was added and the mixture heated to reflux for 3 days. The solution was then poured into a mixture of concentrated HCl and ice, and stirred. The mixture was then diluted with water and extracted with 2×50 mL of CH$_2$Cl$_2$. The extract was washed with brine, then dried over MgSO$_4$ and concentrated in vacuo. The crude residue was subjected to flash column chromatography eluting with EtOAc/hexane to give the title compound (200 mg, 13%). $^1$H NMR (CDCl$_3$): 10.95 (s, 1H), 8.50 (s, 1H), 7.68 (d, 2H), 7.59 (t, 1H), 7.49 (t, 2H), 7.37 (s, 1H), 2.99 (t, 2H), 2.83 (t, 2H), 2.22 (s, 3H), 2.10 (p, 2H).

EXAMPLE 16

5-Amino-6-benzoylindane

The title compound was prepared from 5-acetamido-6-benzoylindane using the procedure described in example 8 in 99% yield. $^1$H NMR (CDCl$_3$): 7.6 (d, 2H), 7.48 (m, 3H), 7.28 (s, 1H), 6.63 (s, 1H), 6.08 (bs, 2H), 2.85 (t, 2H), 2.75 (t, 2H), 2.05 (p, 2H).

EXAMPLE 17

4-Phenylcyclopenta[g]quinazolin-2(1H)-one

To a solution of 5-amino-6-benzoylindane (160 mg, 0.68 mmol) in 6 mL of acetic acid and 0.6 mL of water was added sodium cyanate (53 mg, 0.81 mmol) and the solution was stirred at rt for 3 h. Water was then added to produce a suspension which was filtered and washed with water. The resulting solid was dried under vacuum to give the title compound (139 mg, 79%). $^1$H NMR (CDCl$_3$): 13.25 (bs, 1H), 7.80 (d, 2H), 7.70 (s,1H), 7.60 (m, 4H), 3.05 (t, 2H), 2.95 (t, 2H), 2.15 (p, 2H).

EXAMPLE 18

1-Ethyl-4-phenylcyclopenta[g]quinazolin-2(1H)-one and 2-Ethoxy-4-phenylcyclopenta[g]quinazoline To a suspension of 4-phenylcyclopenta[g]quinazolin-2 (1H)-one (120 mg, 0.46 mmol) and K$_2$CO$_3$ (76 mg, 0.55 mmol) in 4 mL of DMF was added iodoethane (44 μL, 0.55 mmol) and stirred at rt overnight. Water was then added and the resulting suspension extracted with 2×20 mL of EtOAc. The extract was washed with water twice and brine, then dried over MgSO$_4$ and concentrated in vacuo. The crude solid was then subjected to flash column chromatography eluting with acetone/hexane to give the title compound 2-ethoxy-4-phenyl-cyclopenta[g]quinazoline (25 mg, 19%) followed by the title compound 1-ethyl-4-phenylcyclopenta [g]quinazolin-2(1H)-one (66 mg, 50%). $^1$H NMR (CDCl$_3$): 7.7 (d, 2H), 7.63 (s, 1H), 7.53 (m, 3H),. 7.29 (s, 1H)., 4.38 (q, 2H), 3.09 (t, 2H), 2.93 (t, 2H), 2.16 (p, 2H), 1.45 (t, 3H).

EXAMPLE 19

1,4-Benzodioxan-6-acetamide

To a solution of 1,4-benzodioxan-6-amine (2.0 g, 13.2 mmol) in 5 mL of anhydrous pyridine at 0° C. was added acetic anhydride (1.87 mL, 19.9 mmol) and the solution was stirred at rt overnight. The solution was then added to 50 mL of water and was extracted with 2×50 mL of EtOAc. The extract was washed with 1N HCl, water and brine, then dried over MgSO$_2$ and concentrated in vacuo to yield the title compound (1.82 g, 71%). $^1$H NMR (CDCl$_3$): 7.13 (m, 2H), 6.88 (dd, 1H), 6.80 (d, 1H), 4.25 (s, 4H), 2.15 (s, 3H).

EXAMPLE 20

2-Acetamido-4,5-ethylenedioxybenzophenone

To a solution of 1,4-benzodioxan-6-acetamide (1.0 g, 5.18 mmol) and benzoyl chloride (722 μL, 6.22 mmol) in 10 mL of anhydrous CH$_2$Cl$_2$ at 0° C. was added AlCl$_3$ (1.73 g, 12.95 mmol) as a solid. The mixture was stirred to rt overnight. A spatula full of AlCl$_3$ was added and the mixture was stirred at rt for 7 h after which TLC showed almost no starting material. The solution was then poured into a mixture of concentrated HCl and ice, and stirred. The solution was then diluted with water and extracted with 2×50 mL of CH$_{12}$Cl$_2$. The extract was washed with brine, then dried over MgSO$_4$ and concentrated in vacuo. The crude residue was subjected to flash column chromatography eluting with EtOAc/hexane and resulted in the title compound (1.06 g, 69%). $^1$H NMR (CDCl$_3$): 11.07 (bs, 1H), 8.25 (s, 1H), 7.65 (d, 2H), 7.58 (m, 1H), 7.48 (t, 2H), 7.10 (s, 1H), 4.35–4.24 (m, 4H), 2.21 (s, 3H).

EXAMPLE 21

2-Amino-4,5-ethylenedioxybenzophenone

The title compound was synthesized from 2-acetamido-4,5-ethylenedioxybenzophenone using the procedure described in example 8 in 100% yield. $^1$H NMR (CDCl$_3$): 7.60 (d, 2H), 7.48 (m, 3H), 7.00 (s, 1H), 6.24 (s, 1H), 5.95 (bs, 2H), 4.34–4.18 (m, 4H).

EXAMPLE 22

6,7-Ethylenedioxy-4-phenylquinazolin-2(1H)-one

The title compound was synthesized from 2-amino-4,5-ethylenedioxybenzophenone using the procedure described in example 9 in 85% yield. 1H NMR (DMSO-d6): 11.65 (bs, 1H), 7.60 (m, 5H), 7.00 (s, 1H), 6.80 (s, 1H), 4.37 (t, 2H), 4.26 (t, 2H).

EXAMPLE 23

1-Ethyl-6,7-ethylenedioxy-4-phenylquinazolin-2(1H)-one and 2-Ethoxy-6,7-ethylenedioxy-4-phenylquinazoline These compounds were synthesized from 6,7-ethylenedioxy-4-phenylquinazolin-2(1H)-one (100 mg, 0.36 mmol) using the procedure described in example 18.2-Ethoxy-6,7-ethylenedioxy-4-phenylquinazoline (15 mg, 14%); $^1$H NMR (CDCl$_3$): 7.75 (d, 2H), 7.55 (m, 3H), 7.45 (s, 1H), 7.30 (s, 1H), 4.55 (q, 2H), 4.42–4.30 (m, 4H), 1.50(t, 3H). 1-Ethyl-6,7-ethylenedioxy-4-phenylquinazolin-2(1H)-one (31 mg, 28%). $^1$H NMR (CDCl$_3$): 7.70 (d, 2H), 7.50 (m, 3H), 7.35 (s, 1H), 6.88 (s, 1H), 4.45–4.25 (m, 6H), 1.42 (t, 3H).

EXAMPLE 24

6,7-Ethylenedioxy-1-isopropyl-4-phenylquinazolin-2(1H)-one and 6,7-Ethylenedioxy-2-isopropoxy-4-phenylquinazoline To a suspension of sodium hydride (60% dispersion, 44 mg, 1.07 mmol) in 1 mL of DMF was added a suspension of 6,7-ethylenedioxy-4-phenylquinazolin-2(1H)-one (100 mg, 0.36 mmol) in 4 mL of DMF and stirred at rt for 15 min. 2-Iodopropane (150 µL, 1.45 mmol) was then added and the mixture was heated to 60–70° C. for 1.5 h. Excess sodium hydride Was quenched with water and the solution extracted with 25 mL of 9:1 EtOAc:hexane. The extract was washed with 2×25 mL water and brine, then dried with MgSO$_4$ and concentrated in vacuo. The crude solid was subjected to flash column chromatography eluting with acetone:hexane to give the title compound 6,7-ethylenedioxy-2-isopropoxy-4-phenylquinazoline (95 mg, 83%). $^1$H NMR (CDCl$_3$): 7.75 (d, 2H), 7.52 (m, 3H), 7.44 (s, 1H), 7.29 (s, 1H), 5.49 (m, 1H), 4.43–4.30 (m, 4H), 1.46 (d, 6H), followed by the title compound 6,7-ethylenedioxy-1-isopropyl-4-phenylquinazolin-2(1H)-one (9 mg, 8%). $^1$H NMR (CDCl$_3$): 7.70 (d, 2H), 7.50 (m, 3H), 7.30 (s, 1H), 7.05 (s, 1H), 5.15 (m, 1H), 4.41–4.26 (m, 4H), 1.68 (d, 6H).

EXAMPLE 25

N-[6-(1,4-Benzodioxanyl)]-N-ethylthiourea

To a solution of 6-ethylamino-1,4-benzodioxan (400 mg, 2.23 mmol) in 5 mL of acetic acid and 0.5 mL of water was added potassium thiocyanate and the solution heated to 90–100° C. for 5 h. The solution was diluted with water and extracted with 50 mL of EtOAc. The extract was washed with saturated aqueous NaHCO$_3$ and brine, then dried with Na$_2$SO$_4$ and concentrated in vacuo. The crude residue was subjected to flash column chromatography eluting with EtOAc:hexane to give the title compound (100 mg, 19%). $^1$H NMR (CDCl$_3$): 6.92 (d, 1H), 6.72 (d, 1H), 6.69 (dd, 1H), 5.55 (bs, 2H), 4.28 (s, 4H), 4.17 (q, 2H), 1.20 (t, 3H).

EXAMPLE 26

1-Ethyl-6,7-ethylenedioxy-4-phenyl-3,4-dihydroquinazolin-2(1H)-thione

A mixture of N-[6-(1,4-benzodioxanyl)]-N-ethylthiourea (100 mg, 0.42 mmol), benzaldehyde (53 mL, 0.53 mmol) and methanesulfonic acid (10 mL) in 6 mL of benzene was heated to reflux fitted with a Dean-Stark water separator for 2.5 h. The mixture was diluted with 30 mL of EtOAc and washed with water and brine, then dried with MgSO$_4$ and concentrated in vacuo. The crude solid was then triturated with hexane and the resulting solid filtered and dried to give the title compound (83 mg, 61%). $^1$H NMR (CDCl$_3$): 7.40-7.27 (m, 5H), 6.69 (bs, 1H), 6.64 (s, 1H), 6.31 (s, 1H), 5.42 (s, 1H), 4.50 (q, 2H), 4.30–4.18 (m, 4H), 1.40 (t, 3H).

EXAMPLE 27

1-Ethyl-6,7-ethylenedioxy-4-phenylquinazolin-2(1H)-thione

A mixture of 1-ethyl-6,7-ethylenedioxy-4-phenyl-3,4-dihydroquinazolin-2(1H)-thione (77 mg, 0.24 mmol) and MnO$_2$ (180 mg, 2.07 mmol) in 5 mL of CHCl$_3$ was stirred at rt for 3 days. The solids were filtered off and the solution concentrated in vacuo. The crude residue was subjected to flash column chromatography eluting with EtOAc:hexane to give the title compound (35 mg, 46%). $^1$H NMR (CDCl$_3$): 7.72 (dd, 2H), 7.53–7.49 (m, 3H), 7.38 (s, 1H), 7.09 (3, 1H), 4.90 (m, 2H), 4.48–4.30 (m, 4H), 1.55 (t, 3H).

EXAMPLE 28

1-Isopropyl-6,7-methylenedioxy-4-(3,4-ethylenedioxyphenyl)-3,4-dihydroquinazolin-2(1H)-one This compound was synthesized from N-isopropyl-N-[3,4-(methylenedioxy)-phenyl]urea (240 mg) and 1,4-benzodioxan-6-carboxaldehyde (181 mg) by the procedure described in example 10 in 32% yield, mp: 185–187° C. $^1$H NMR (CDCl$_3$): 6.86-6.75 (m, 3H), 6.67 (s, 1H), 6.30 (s, 1H), 5.91 (s, 1H), 6.89 (s, 1H), 5.18 (s, 1H), 4.99 (br s, 1H), 4.44 (m, 2H), 4.25 (s, 4H), 1.56 (d, J=6.8, 3H), 1.55 (d, J=6.8, 3H). Anal. calcd. for $C_{20}H_{20}N_2O_5 \cdot (\frac{1}{2})H_2O$: C, 63.65; H, 5.61; N, 7.42. Found: C. 63.37; H, 5.34; N, 7.07.

EXAMPLE 29

1-Isopropyl-6,7-methylenedioxy-4-(3,4-ethylenedioxyphenyl)-quinazolin-2(1H)-one

This compound was synthesized from 1-isopropyl-3,4-dihydro-6,7-methylenedioxy-4-(3,4-ethylenedioxyphenyl)quinazolin-2(1H)-one (128 mg) by the procedure described in example 12 in 45% yield, mp: 214–217° C. $^1$H NMR (CDCl$_3$): 7.26-7.20 (m, 3H), 7.03 (s, 1H), 6.96 (d, J=8.7, 1H), 6.09 (s, 2H), 5.15 (m, 1H), 4.32 (s, 4H), 1.67 (d, J=6.9, 6H). Anal. calcd. for $C_{11}H_{18}N_2O \cdot (\frac{1}{4})H_2O$: C, 64.77; H, 5.03; N, 7.55. Found: C, 64.65; H, 4.81; N, 7.47.

EXAMPLE 30

1-Isopropyl-6,7-ethylenedioxy-4-(3,4-ethylenedioxyphenyl)-3,4-dihydroquinazolin-2(1H)-one This compound was synthesized from N-isopropyl-N-[3,4-(ethylenedioxy)-phenyl]urea (132 mg) and 1,4-benzodioxan-6-carboxaldehyde (113 mg) by the procedure described in example 10 in 14% yield, mp: 92–95° C. $^1$H NMR (CDCl$_3$): 6.85-6.76 (m, 3H), 6.62 (s, 1H), 6.32 (s, 1H), 5.20 (s, 1H), 4.99 (s, 1H), 4.46 (m, 1H), 4.24 (s, 4H), 4.23–4.17 (m, 4H), 1.56 (d, J=6.9, 3H), 1.54 (d, J=6.9, 3H).

EXAMPLE 31

1-Ethyl-6,7-methylenedioxy-4-(2-naphthyl)-3,4-dihydro-quinazolin-2(1H)-one

This compound was synthesized from N-ethyl-N-[3,4-(methylenedioxy)phenyl]urea (247 mg) and 2-naphthaldehyde (182 mg) by the procedure described in example 10 in 46% yield, mp: 193–195° C. $^1$H NMR (CDCl$_3$): 7.86-7.82 (m, 2H), 7.74 (s, 1H), 7.52–7.42 (m, 4H), 6.57 (s, 1H), 6.30 (s,1H), 5.90 (s,1H), 5.87 (s, 1H), 5.61 (s, 1H), 5.18 (s, 1H), 3.97 (q, J=6.6, 2H), 1.32 (t, J=6.6, 3H). Anal. calcd. for C$_{21}$H$_{18}$N$_2$O$_3$: C, 72.82; H, 5.24; N, 8.09. Found: C, 72.53; H, 4.95; N, 7.54.

EXAMPLE 32

1-Isopropyl-6,7-methylenedioxy-4-(2-naphthyl)-3,4-dihydro-quinazolin-2(1H)-one This compound was synthesized from N-isopropyl-N-[3,4-(methylenedioxy)-phenyl]urea (226 mg) and 2-naphthaldehyde (152 mg) by the procedure described in example 10 in 60% yield, mp: 186–178° C. $^1$H NMR (CDCl$_3$): 7.86-7.75 (m, 4H), 7.52–7.42 (m, 3H), 6.70 (s, 1H), 6.32 (s, 1H), 5.91 (d, J=1.3, 1H), 5.88 (d, J=1.3, 1H), 5.47 (s, 1H), 5.16 (br s, 1H), 4.45 (m, 1H), 1.58 (m, 6H). Anal. calcd. for C$_{22}$H$_{20}$N$_2$O$_3$: C. 73.32; H, 5.59; N, 7.77. Found: C, 73.10; H, 5.49; N, 7.62.

EXAMPLE 33

1-Isopropyl-6,7-methylenedioxy-4-(4-biphenyl)-3,4-dihydro-quinazolin-2(1H)-one This compound was synthesized from N-isopropyl-N-[3,4-(methylenedioxy)-phenyl]urea (213 mg) and 4-phenylbenzaldehyde (171 mg) by the procedure described in example 10 in 58% yield, mp: 82–84° C. $^1$H NMR (CDCl$_3$): 7.60-7.56 (m, 4H), 7.47–7.35 (m, 5H), 6.70 (s, 1H), 6.37 (s, 1H), 5.93 (d, J=1.4, 1H), 5.90 (d, J=1.4, 1H), 5.34 (s, 1H), 5.18 (s, 1H), 4.45 (m, 1H), 1.57 (d, J=6.8, 3H), 1.56 (d, J=6.8, 3H). Anal. calcd. for C$_{24}$H$_{22}$N$_2$O$_3$: C, 74.59; H, 5.74; N, 7.25. Found: C, 74.36; H, 5.71; N, 6.94.

EXAMPLE 34

1-Isopropyl-6,7-methylenedioxy-4-(5-indanyl)-3,4-dihydro-quinazolin-2(1H)-one This compound was synthesized from N-isopropyl-N-[3.4-(methylenedioxy)-phenyl]urea (291 mg) and 5-indancarboxaldehyde (190 mg) by the procedure described in example 10 in 59% yield, mp: 146–148° C. $^1$H NMR (CDCl$_3$): 7.21-7.04 (m, 3H), 6.67 (s,1H), 6.30 (s, 1H), 5.91 (d, J=1.4, 1H), 5.89 (d, J=1.4, 1H), 5.27 (s, 1H), 5.00 (s, 1H), 4.45 (m, 1H), 2.89 (m, 4H), 2.08 (m, 2H), 2.08 (m, 2H), 1.58–1.55 (m, 6H). Anal. calcd. for C$_{21}$H$_{22}$N$_2$O$_3$: C, 71.98; H[6.33; N, 7.99. Found: C, 72.25; H, 6.59; N, 7.89.

EXAMPLE 35

1-Isopropyl-6,7-methylenedioxy-4-(2-chloro-4,5-methylenedioxyphenyl)-3,4-dihydro-quinazolin-2(1H)-one This compound was synthesized from N-isopropyl-N-[3.4-(methylenedioxy)-phenyl]urea (410 mg) and 6-chloropiperonal (350 mg) by the procedure described in example 10 in 65% yield. $^1$H NMR (CDCl$_3$): 6.86 (s, 1H), 6.77 (s, 1H), 6.48 (s, 1H), 6.40 (s, 1H), 5.95 (s, 4H), 5.66 (d, J=2.5, 1H), 5.21 (s, 1H), 4.48 (m, 1H), 1.53 (d, J=6.5, 6H).

EXAMPLE 36

1-Isopropyl-6,7-methylenedioxy-4-(3-pyridyl)-3,4-dihydro-quinazolin-2(1H)-one This compound was synthesized from N-isopropyl-N-[3,4-(methylenedioxy)-phenyl]urea (238 mg) and 3-pyridinecarboxaldehyde (100 μL) by the procedure described in example 10 in 36% yield, mp: 172–174° C. $^1$H NMR (CDCl$_3$): 8.58-8.56 (m, 3H), 7.63 (m, 1H), 7.29 (m, 2H), 6.70 (s, 1H), 6.34 (s, 1H), 5.94 (d, J=1.3, 1H), 5.92 (d, J=1.3, 1H), 5.33 (s, 1H), 5.29 (s, 1H), 4.41 (m, 1H), 1.53 (d, J=6.8, 3H), 1.50 (d, J=6.8, 3H).

EXAMPLE 37

1-Isopropyl-6,7-methylenedioxy-4-(3-quinolyl)-3,4-dihydro-quinazolin-2(1H)-one This compound was synthesized from N-isopropyl-N-[3,4-(methylenedioxy)-phenyl]urea (308 mg) and 3-quinolinecarboxaldehyde (243 mg) by the procedure described in example 10 in 14% yield, mp: 202–205° C. $^1$H NMR (CDCl$_3$): 8.89 (d, J=2.0, 1H), 8.11 (d, J=7.6, 1H), 8.05 (s, 1H), 7.80 (d, J=7.6, 1H), 7.74 (t, J=7.6, 1H), 7.58 (t, J=7.6, 1H), 6.72 (s, 1H), 6.41 (s, 1H), 5.94 (s, 1H), 5.92 (s, 1H), 5.52 (d, J=1.9, 1H), 5.25 (s, 1H), 4.42 (m, 1H), 1.57 (d, J=7.0, 3H), 1.56 (d, J=7.0, 3H).

EXAMPLE 38

1-Isopropyl-6,7-methylenedioxy-4-(3,4-difluoromethylenedioxyphenyl)-3,4-dihydro-quinazolin-2(1H)-one This compound was synthesized from N-isopropyl-N-[3,4-(methylenedioxy)-phenyl]urea (288 mg) and 3,4-difluoromethylene-benzaldehyde (248 mg) by the procedure described in example 10 in 43% yield, mp: 91–93° C. $^1$H NMR (CDCl$_3$): 7.03 (s, 3H), 6.69 (s, 1H), 6.29 (s, 1H), 5.94 (d, J=1.0, 1H), 5.92 (d, J=1.0, 1H), 5.28 (d, J=1.3, 1H), 5.13 (s, 1H), 4.43 (m, 1H), 1.56 (d, J=6.9, 3H), 1.54 (d, J=6.9, 3H). Anal. calcd. for C$_{19}$H$_{16}$F$_2$N$_2$O$_5$: C, 58.46; H, 4.13; N, 7.18. Found: C, 58.36; H, 3.91; N, 7.08.

EXAMPLE 39

1-Isopropyl-6,7-methylenedioxy-4-(benzoxazol-5-yl)-3,4-dihydroquinazolin-2(1H)-one A solution of 1-isopropyl-6,7-methylenedioxy-4-(3-amino-4-hydroxyphenyl)quinazolin-2(1H)-one (93 mg) in triethyl orthoformate (3 mL) was refluxed for 1 h, cooled to rt, diluted with EtOAc (30 mL), washed with water, saturated aqueous solution of NaHCO$_3$ and brine, dried over Na$_2$SO$_4$, and concentrated in vacuo to yield the title compound as a tan solid (70 mg, 71%), mp: 84–86° C. $^1$H NMR (CDCl$_3$): 8.12 (s, 1H), 7.72 (s, 1H), 7.59 (d, J=8.3, 2H), 7.39 (d, J=8.3, 1H), 6.71 (s, 1H), 6.28 (s, 1H), 5.92 (s, 1H), 5.90 (s, 1H), 5.49 (s, 1H), 5.14 (s, 1H), 4.45 (m, 1H), 1.58 (d, J=6.6, 3H), 1.55 (d, J=6.6, 3H).

EXAMPLE 40

1-Isopropyl-6,7-methylenedioxy-4-(2-naphthyl)quinazolin-2(1H)-one

This compound was synthesized from 1-isopropyl-3,4-dihydro-6,7-methylenedioxy-4-(2-naphthyl)quinazolin-2(1H)-one (180 mg) by the procedure described in example 12 in 92% yield, mp: 213–215° C. $^1$H NMR (CDCl$_3$): 8.20 (s, 1H), 7.98–7.90 (m, 3H), 7.81–7.56 (m, 3H), 7.21 (s, 1H), 7.08 (s, 1H), 6.10 (s, 2H), 5.20 (m, 1H), 1.71 (d, J=6.9, 6H). Anal. calcd. for C$_{22}$H$_{18}$N$_2$O$_3$: C, 73.73; H, 5.06; N, 7.82. Found: C, 73.52; H, 5.05; N, 7.59.

EXAMPLE 41

1-Isopropyl-6,7-methylenedioxy-4-(5-indanyl)quinazolin-2(1H)-one

This compound was synthesized from 1-isopropyl-3,4-dihydro-6,7-methylenedioxy-4-(5-indanyl)quinazolin-2(1H)-one (210 mg) by the procedure described in example 12 in 86% yield, mp: 73–75° C. $^1$H NMR (CDCl$_3$): 7.57 (s, 1H), 7.43 (d, J=7.6, 1H), 7.32 (d, J=7.6, 1H), 7.21 (s, 1H), 7.04 (s, 1H), 6.09 (s, 2H), 5.18 (m, 1H), 2.98 (t, J=7.0, 4H), 2.13 (p, J=7.0, 2H), 1.68 (d, J=6.9, 6H). Anal. calcd. for C$_{21}$H$_{20}$N$_2$O$_3$.(½)H$_2$O: C, 70.57; H, 5.92; N, 7.84. Found: C, 70.93; H, 5.64; N, 7.68.

EXAMPLE 42

1-Isopropyl-6,7-methylenedioxy-4-(2-chloro-4,5-methlylenedioxyphenyl)quinazolin-2(1H)-one This compound was synthesized from 1-isopropyl-3,4-dihydro-6,7-methylenedioxy-4-(2-chloro-4,5-methylenedioxyphenyl)quinazolin-2(1H)-one (550 mg) by the procedure described in example 12 in 67% yield, mp: 147–150° C. $^1$H NMR (CDCl$_3$): 7.04 (s, 1H), 6.93 (s, 1H), 6.88 (s, 1H), 6.75 (s, 1H), 6.09–6.06 (m, 4H), 5.22 (m, 1H), 1.70 (d, J=6.8, 3H), 1.69 (d, J=6.8, 3H). Anal. calcd. for C$_{19}$H$_{15}$ClN$_2$O$_5$: C, 59.00; H, 3.91; N, 7.24. Found: C, 58.44; H, 3.85; N, 6.94.

EXAMPLE 43

1-Isopropyl-6,7-methylenedioxy-4-(3-pyridyl)quinazolin-2(1H)-one

This compound was synthesized from 1-isopropyl-3,4-dihydro-6,7-methylenedioxy-4-(3-pyridyl)quinazolin-2(1H)-one (100 mg) by the procedure described in example 12 in 91% yield, mp: 58–60° C. 1H NMR (CDCl$_3$): 8.90 (s, 1H), 8.77 (d, J=4.1, 1H), 8.07 (d, J=7.7, 1H), 7.47 (dd, J=4.1, 7.7, 1H), 7.08 (s, 1H), 7.06 (s, 1H), 6.12 (s, 2H), 5.17 (m, 1H), 1.70 (d, J=6.9, 6H).

EXAMPLE 44

1-Isopropyl-6,7-methylenedioxy-4-(3-quinolyl)quinazolin-2(1H)-one

This compound was synthesized from 1-isopropyl-3,4-dihydro-6,7-methylenedioxy-4-(3-quinolyl)quinazolin-2(1H)-one (60 mg) by the procedure described in example 12 in 92% yield, mp: 279–281° C. $^1$H NMR (CDCl$_3$): 9.21 (s, 1H), 8.58 (s, 1H), 8.20 (d, J=8.0, 1H), 7.94 (d, J=7.7, 1H), 7.87–7.63 (m, 2H), 7.14 (s, 1H), 7.11 (s, 1H), 6.13 (s, 2H), 5.20 (m, 1H), 1.72 (d, J=6.9, 6H). Anal. calcd. for C21H17N3O3: C, 70.18; H, 4.76; N, 11.69. Found: C, 69.78; H, 4.97; N, 11.30.

EXAMPLE 45

1-Isopropyl-6,7-methylenedioxy-4-(3,4-difluoromethylenedioxyphenyl)quinazolin-2(1H)-one This compound was synthesized from 1-isopropyl-3,4-dihydro-6,7-methylenedioxy-4-(3,4-difluoromethylenedioxyphenyl)quinazolin-2(1H)-one (200 mg) by the procedure described in example 12 in 81% yield, mp: 243–245° C. $^1$H NMR (CDCl$_3$): 7.46 (s, 1H), 7.44 (dd, J=8.0, 1.7, 1H), 7.18 (d, J=8.0, 1H), 7.09 (s, 1H), 7.06 (s, 1H), 6.11 (s, 2H), 5.14 (m, 1H), 1.69 (d, J=7.1, 6H). Anal. calcd. for C$_{19}$H$_{14}$F$_2$N$_2$O$_5$.(½)H$_2$O: C, 57.44; H, 3.81; N, 7.05. Found: C, 57.55; H, 3.66; N, 7.00.

EXAMPLE 46

1-Isopropyl-6,7-methylenedioxy-4-[6-(2-benzoxazolinone)]quinazolin-2(1H)-one

This compound was synthesized from 1-isopropyl-3,4-dihydro-6,7-methylenedioxy-4-[6-(2-benzoxazolinone)]quinazolin-2(1H)-one (90 mg) by the procedure described in example 12 in 81% yield, mp: 192–196° C. $^1$H NMR (CDCl$_3$): 7.67 (s, 1H), 7.35 (d, J=8.3, 1H), 7.22 (d, J=8.3, 1H), 7.12 (s, 1H), 7.05 (s, 1H), 6.11 (s, 2H), 5.42 (s, 1H), 5.12 (m, 1H), 1.69 (d, J=6.8, 6H). Anal. calcd. for C$_{19}$H$_{154}$N$_3$O$_5$.H$_2$O: C, 59.53; H, 4.46; N, 10.96. Found: C. 59.86; H, 4.39; N, 10.28.

EXAMPLE 47

2-Chloro-4-(3,4-methylenedioxyphenyl)-6,7-methylendioxyquinazoline 4-(3,4-Methylenedioxyphenyl)-6,7-methylenedioxyquinazolin-2(1H)-one (1 g, 3.23 mmol) was treated with DMF (one drop) and phosphorous oxychloride (7 mL, 75 mmol) and the suspension was heated to reflux for 4 h. Upon cooling to rt, the reaction mixture was poured into ice and the pH was adjusted to ~8 with 3N NaOH solution. The precipitate was vacuum filtered and dried to give the title compound as a brown granular solid (1.18 g). $^1$H NMR (DMSO-d$_6$) 6.16 (s, 2H), 6.32 (s,2H), 6.85–7.41 (m, 5H).

EXAMPLE 48

1-Isopropyl-6,7-methylenedioxy-4-(5-benzoxazole)quinazolin-2(1H)-one

This compound was synthesized from 1-isopropyl-3,4-dihydro-6,7-methylenedioxy-4-(5-benzoxazole)quinazolin-2(1H)-one (50 mg) by the procedure described in example 12 in 29% yield, mp: 241–243° C. $^1$H NMR (CDCl$_3$): 8.21 (s, 1H), 8.10 (s, 1H), 7.82 (d, J=8.4, 1H), 7.72 (d, J=8.4, 1H), 7.14 (s, 1H), 7.08 (s, 1H), 6.11 (s, 1H), 5.90 (s, 2H), 5.18 (m, 1H), 1.71 (d, J=6.9, 6H). Anal. calcd. for C$_{19}$H$_{15}$N$_3$O$_4$: C, 65.32; H, 4.33; N, 12.03. Found: C. 65.33; H, 4.58; N, 11.99.

EXAMPLE 49

6,7-Difluoromethylenedioxy-1-isopropyl-4-(3,4-methylenedioxyphenyl)-3,4-dihydroquinazolin-2(1H)-one a) 2,2-Difluoro-5-isopropylamino-1,3-benzodioxole. A mixture of 5-amino-2,2-difluoro-1,3-benzodioxole (2.00 g, 11.56 mmol) and acetone (890 mL, 12.14 mmol) in 50 mL of 1:1 THF:MeOH at 0° C. was treated with 10 mL of glacial acetic acid and stirred at 0° C. for 1 hour. Sodium cyanoborohydride (1.53 g, 24.28 mmol) was then added in one portion as a solid, and the mixture stirred with warming to RT overnight. The reaction was treated with 20 mL of 3N NaOH and partitioned between 100 mL of $CH_2Cl_2$ and 100 mL of 1N NaOH. The aqueous layer was extracted with 100 mL of $CH_2Cl_2$ and the combined $CH_2Cl_2$ layers were washed with 2×100 mL of 1N NaOH followed by 100 mL of brine. The solution was dried with $MgSO_4$ and then concentrated in vacuo to dryness, resulting in the title compound as a colorless oil (2.36 g, 95%). $^1H$ NMR ($CDCl_3$): 6.82 (d, 1H, J=8.5 Hz), 6.34 (d, 1H, J=2.1 Hz), 6.20 (dd, 1H, J=8.5 and 2.1 Hz), 3.52 (hp, 1H, J=6.1 Hz), 3.10–3.30 (bs, 1H, NH), 1.20 (d, 6H, J=6.1 Hz).

b) N-(5,5-Difluorobenzodioxole)-N-isopropylurea. The title compound was synthesized from 2,2-difluoro-5-isopropylamino-1,3-benzodioxole using the same procedure described in example 17 in 72% yield. $^1H$ NMR ($CDCl_3$): 7.12 (d, 1H), 6.94 (m, 2H), 4.84 (hp, 1H, J=6.9 Hz), 4.24 (bs, 2H, $NH_2$), 1.06 (d, 6H, J=6.9 Hz).

c) 6,7-Difluoromethylenedioxy-1-isopropyl-4-(3,4-methylenedioxyphenyl)-3,4-dihydroquinazolin-2(1H)-one. The title compound was synthesized from N-(5,5-difluorobenzodioxole)-N-isopropylurea using the same procedure described in example 26 in 40% yield, mp 147–150° C.; $^1H$ NMR ($CDCl_3$): 6.88-6.75 (m, 4H), 6.50 (s, 1H), 5.99 (s, 2H), 5.28 (s, 1H), 5.08 (bs, 1H, NH), 4.45 (hp, 1H, J=6.9 Hz), 1.58(t, 6H, J=6.9 Hz).

EXAMPLE 50

6,7-Difluoromethylenedioxy-1-isopropyl-4-(3,4-methylenedioxyphenyl)quinazolin-2(1H)-one The title compound was synthesized from 6,7-difluoromethylenedioxy-1-isopropyl-4-phenyl-3,4-dihydroquinazolin-2(1H)-one using the same procedure described in example 27 in 85% yield, mp 165–168° C.; $^1H$ NMR ($CDCl_3$): 7.53 (s, 1H), 7.30–7.19 (m, 4H), 6.94 (d, 1H), 6.08 (s, 2H), 5.09 (hp, 1H, J=7.1 Hz), 1.69 (d, 6H, J=7.1 Hz).

EXAMPLE 51

6,7-Ethylenedioxy-1-isopropyl-4-(3,4-methylenedioxyphenyl)-3,4-dihydroquinazolin-2(1H)-one The title compound was synthesized from 5-amino-1,4-benzodioxane in three steps similar to example 49, mp 197–200° C.; $^1H$ NMR ($CDCl_3$): 6.77 (m, 3H), 6.64 (s, 1H), 6.31 (s, 1H), 5.96 (s, 2H), 5.24 (s, 1H), 5.21 (bs, 1H), 4.46 (hp, 1H, J=6.3 Hz), 4.21 (m, 4H), 1.55 (t, 6H, J=6.3 Hz).

EXAMPLE 52

6,7-Ethylenedioxy-1-isopropyl-4-(3,4-methylenedioxyphenyl)quinazolin-2(1H)-one

The title compound was synthesized from 6,7-ethylenedioxy-1-isopropyl-4-(3,4-methylenedioxyphenyl)-3,4-dihydroquinazolin-2(1H)-one using the same procedure described in example 27 in 57% yield, mp 229–231° C.; $^1H$ NMR ($CDCl_3$): 7.37 (s, 1H), 7.29–7.20 (m, 2H), 7.02 (s, 1H), 6.91 (d, 1H), 6.06 (s, 2H), 5.11 (hp, 1H, J=6.9 Hz), 4.34 (m, 4H), 1.69 (d, 6H, J=6.9 Hz).

EXAMPLE 53

4-(2,3-Dihydrobenzofuran-5-yl)-1-isopropyl-6,7-methylenzedioxy-3,4-dihydroquinazolin-2(1H)-one The title compound was synthesized from N-benzodioxan-6-yl-N-isopropylurea using the same procedure described in example 26 in 61% yield, mp 183–185° C.; $^1H$ NMR ($CDCl_3$): 7.14 (s, 1H), 7.02 (d, 1H), 6.74 (d, 1H), 6.68 (s, 1H), 6.27 (s, 1H), 5.90 (d, 2H), 5.24 (s, 1H), 5.10 (bs, 1H, NH), 4.58 (t, 2H), 4.45 (hp, 1H, J=6.9 Hz), 3.18 (t, 2H), 1.56 (t, 6H, J=6.9 Hz).

EXAMPLE 54

4-(2,3-Dihydrobenzofuran-5-yl)-1-isopropyl-6,7-methylenedioxyquinazolin-12(1H)-one The title compound was synthesized from 4-(2,3-dihydrobenzofuran-5-yl)-1-isopropyl-6,7-methylenedioxy-3,4-dihydroquinazolin-2(]H)-one using the same procedure described in example 27 in 90% yield, mp 206–209° C.; $^1H$ NMR ($CDCl_3$): 7.67 (s, 1H), 7.48 (d, 1H), 7.25 (s, 1H), 7.04 (s, 1H), 6.88 (d, 1H), 6.10 (s, 214), 5.16 (hp, 1H, J=7.1 Hz), 4.67 (t, 2H), 3.29 (t, 2H), 1.68 (d, 6H, J=7.1 Hz).

EXAMPLE 55

2-(Imidazol-1-yl)ethyl-6,7-methylenedioxy-4-(3,4-methylenedioxyphenyl)quinazoline To a suspension of hexane washed NaH (60% in oil, 84 mg, 2.1 mmol) in dry DMF (5 mL) was added imidazole (142 mg, 2.1 mmol). The mixture was stirred at rt for 15 min and was treated with 2-chloroethyl-6,7-methylenedioxy-4-(3,4-methylenedioxyphenyl)quinazoline (232 mg, 0.7 mmol), and then with NaI (105 mg, 0.7 mmol). The mixture was stirred at rt for 15 h and it was poured into ice-water. The precipitated solid was collected by filtration, washed with water, and air dried. The yellow solid was then crystallized from EtOAc to give the title compound as pale yellow needles (101 mg); mp 160–163° C.; $^1H$ NMR ($CDCl_3$) 7.5 (s, 1H) 7.33 (s, 1H), 7.27 (s, 1H), 7.15–7.20 (m, 2H), 6.91–7.05 (m, 3H), 6.15 (s, 2H), 6.08 (s, 2H), 4.60 (m, 211), 3,53 (m, 2H). Anal. calcd. for $C_{21}H_{16}N_4O_4$: C, 64.94; H, 4.15; N, 14.43. Found: C, 64.52; H, 4.11; N, 14.12.

EXAMPLE 56

2-[(1-Methyl-2-imidazolyl)thio]methyl-6,7-methylenedioxy-4-(3,4-methylenedioxy-phenyl) quinazoline A suspension of 2-chloromethyl-6,7-methylenedioxy-4-(3,4-methylenedioxy-phenyl)quinazoline (193 mg, 0.61 mmol) and 2-mercapto-1-methylimidazole (80 mg, 0.7 mmol) in dry DMF (2 mL) was treated with $K_2CO_3$ (97 mg, 0.7 mmol). The mixture was stirred at rt for 2 h, and then it was poured into ice-water. The mixture were extracted with EtOAc and the extract was washed with water and brine, dried over anhydrous $MgSO_4$, and evaporated to yield the crude product, which was crystallized from EtOAc-hexane to give the title compound as colorless rods (142 mg); mp 155–160° C.; $^1H$ NMR ($CDCl_3$) 7.36 (s, 1H), 7.27 (s, 1H), 7.17 (d, J=7.7, 1H), 7.16 (s, 1H), 7.09 (s, 1H), 6.95 (d, J=7.7, 1H), 6.91 (s,13H), 6.14 (s, 2H), 6.07 (s, 2H), 4.53 (s, 2H), 3,51 (s, 3H). Anal. calcd. for $C_{21}H_{16}N_4O_4S$: C, 59.99; H 3.84; N 13.33. Found: C, 59.78; H 3.82; N 13.20.

EXAMPLE 57

2-Iodomethyl-6,7-methylenedioxy-4-(3,4-methylenedioxyphenyl)quinazoline

A suspension of 2-chloromethyl-6,7-methylenedioxy-4-(3,4-methylenedioxy-phenyl)quinazoline (159 mg, 0.5 mmol) and sodium acetate (82 mg, 1 mmol) in acetone (7 mL) was treated with NaI (90 mg, 0.6 mmol). The mixture was refluxed for 2 h, and then it was poured into ice-water. The precipitated solid was collected by filtration, washed with water, and dried. The crude product was crystallized from EtOAc-hexane to give the title compound as yellow rods (105 mg); mp 155–160° C.; $^1$H NMR (CDCl$_3$) 7.36 (s, 1H), 7.29 (s, 1H), 7.23 (s, 1H), 7.22 (d, J=6.5, 1H), 6.98 (d, J=8.3, 1H), 6.15 (s, 2H), 6.07 (s, 2H), 4.71 (s, 2H). Anal. calcd. for $C_{17}H_{11}N_2O_4 \cdot (¼)H_2O$: C, 46.50; H, 2.62; N, 6.38. Found: C, 46.43; H, 2.53; N, 6.28.

EXAMPLE 58

6,7-Methylenedioxy-2-(1,2,4-triazol-1-yl)methyl-4-(3,4-methylenedioxyphenyl)quinazoline The title compound was prepared in a manner similar to example 55 as colorless needles, mp 195–198° C.; $^1$H NMR (CDCl$_3$) 8.42 (s, 1H), 7.99 (s, 1H), 7.37 (s, 1H), 7.27 (s, 1H), 7.18 (d, J=7.8, 1H), 7.16 (s, 1H), 6.95 (d, J=7.8, 1H), 6.15 (s, 2H), 6.08 (s, 2H), 5.70 (m, 2H). Anal. calcd. for $C_{19}H_{13}N_5O_4$: C, 60.80; H, 3.49; N 18.66. Found: C, 60.76; H, 3.37; N 18.16.

EXAMPLE 59

6,7-Methylenedioxy-2-(piperazin-1-yl)methyl-4-(3,4-methylenedioxyphenyl)quinazoline A suspension of 2-chloromethyl-6,7-methylenedioxy-4-(3,4-methylenedioxy-phenyl)quinazoline (96 mg, 0.3 mmol) in EtOH (9 mL) was treated with piperazine (860 mg, 10 mmol). The mixture was stirred at rt for 15 h, then it was poured into ice cold dilute NaHCO$_3$ solution. On standing at rt for 72 h the title compound was crystallized out as colorless plates. It was collected by filtration, washed with water, and dried to give 74 mg of solid; mp 73–76° C. $^1$H NMR (CDCl$_3$) 7.37 (d, J=8.4, 1H), 7.16–7.24 (m, 3H), 6.97 (d, J=8.4, 1H), 6.14 (s, 2H), 6.07 (s, 2H), 3.95 (s, 2H), 2.97 (bs, 4H), 2.65 (bs, 4H).

EXAMPLE 60

2-(Imidazol-1-yl)methyl-6,7-methylenedioxy-4-(3,4-methylenedioxyphenyl)quinazoline The title compound was prepared in a manner similar to example 55 as pale yellow needles, mp 182–185° C.; $^1$H NMR (CDCl$_3$) 7.78 (s, 1H), 7.00–7.41 (m, 5H), 6.90 (s 1H), 6.28 (s, 2H), 6.14 (s, 2H), 5.47 (s, 2H). Anal. calcd. for $C_{20}H_{14}N_4O_4$: C, 64.17; H, 3.77; N, 14.97. Found: C, 63.86; H, 3.63; N, 14.60.

EXAMPLE 61

2-Acetoxymethyl-6,7-methylenedioxy-4-(3,4-methylenedioxyphenyl)quinazoline

A suspension of 2-chloromethyl-6,7-methylenedioxy-4-(3,4-methylenedioxy-phenyl)quinazoline (159 mg, 0.5 mmol) in DMF (2 mL) was treated with sodium acetate (104 mg, 1.2 mmol). The mixture was heated at 100° C. for 2 h, than it was poured into ice-water. The precipitated solid was collected by filtration, washed with water, and dried. The crude product was crystallized from EtOAc-hexane to give the title compound as colorless needles (95 mg); mp 144–147° C.; $^1$H NMR (CDCl$_3$) 7.37 (s 1H), 7.33 (s, 1H), 7.19–7.24 (m, 2H), 6.97 (d, J=8.5, 1H), 6.15 (s, 2H), 6.07 (s, 2H), 5.41 (s, 2H), 2.24 (s, 3H). Anal. calcd. for $C_{19}H_{14}N_2O_6$: C, 62.30; H, 3.85; N, 7.65. Found: C, 62.12; H, 3.92; N, 7.65.

EXAMPLE 62

2-(N-Phenylpiperazin-1-yl)methyl-6,7-Methylenedioxy-4-(3,4-methylenedioxyphenyl) quinazoline A suspension of 2-chloromethyl-6,7-methylenedioxy-4-(3,4-methylenedioxy-phenyl)quinazoline (159 mg, 0.5 mmol), K$_2$CO$_3$ (70 mg, 0.5 mmol), and 4-phenylpiperazine (97 mg, 0.6 mmol) in MeCN (6 mL) was treated with NaI (75 mg, 0.5 mmol). The mixture was refluxed for 0.5 h, and then it was poured into ice-water. The precipitated solid was collected, by filtration, washed with water, and dried. The crude product was crystallized from EtOAc to give the title compound as colorless needles (140 mg); mp 183–185° C., $^1$H NMR (CDCl$_3$) 7.4 (s, 1H), 7.36 (s, 1H), 7.27 (s, 1H), 7.20–7.30 (m, 4H), 6.91–7.01 (m, 3H), 6.84 (m, 1H), 6.15 (s, 2H), 6.07 (s, 2H), 4.04 (m, 2H), 3.30 (m, 2H), 2.87 (m, 2H). Anal. calcd. for $C_{27}H_{24}N_4O_4$: C, 69.22; H, 5.16; N, 11.96. Found: C, 69.00; H, 5.18; N, 11.99.

EXAMPLE 63a AND 63b 6,7-Methylenedioxy-4-(3,4-methylenedioxyphenyl)-2-(cyclopropylmethoxy)-quinazoline (a) and 1-cyclopropylmethyl-6,7-methylenedioxy-4-(3,4-methylenedioxyphenyl)quinazolin-2(1H)-one (b)

To a suspension of 6,7-methylenedioxy-4-(3,4-methylenedioxyphenyl)-quinazolin-2-one (310 mg, 1.00 mmol) in DMF (7 mL) was added NaH (97%, 32 mg, 1.33 mmol). The mixture was stirred at 25° C. for 45 min, then (bromomethyl)cyclopropane (0.2 mL, 2.0 mmol) was added. The resulting mixture was then heated at 100° C. for 6 h, cooled to rt, poured into ice-water (50 mL) and stirred for 30 min. The resulting precipitate was collected by filtration and the solid was dissolved in ethyl acetate. The solution was washed with water and brine, dried over anhydrous MgSO$_4$, and the solvent was removed in vacuo. This crude product was separated by chromatography in silica gel. Elution with hexane:acetone (65:35) gave 6,7-methylenedioxy-4-(3,4-methylenedioxyphenyl)-2-(cyclopropylmethoxy)-quinazoline as yellow solid (60 mg); mp 175–182° C.; $^1$H NMR (CDCl$_3$) 7.31 (s, 1H), 7.21–7.25 (m, 3H), 7.14 (s, 1H), 6.93–6.96 (d, J=8.4, 1H), 6.09 (s, 2H), 6.06 (s, 2H), 4.29–4.31 (t, J=7.2, 2H), 3.2 (s, 1H); 0.63 (s, 2H), 0.41 (s, 2H); $C_{20}H_{16}N_2O_5$; C, 65.93; H, 4.43; N, 7.69. Further elution with the same solvents gave 1-cyclopropylmethyl-6,7-methylenedioxy-4-(3,4-methylenedioxyphenyl) quinazolin-2(1H)-one as pale yellow solid (75 mg); mp 255–260° C.; $^1$H NMR (CDCl$_3$) 7.18–7.36 (m, 3H), 6.82–7.02 (m, 3H), 6.11 (s, 2H), 6.06 (s, 2H), 4.22 (d, J=6.8, 2H), 1.18–1.40 (m, 1H), 0.41–0.78 (m, 4H); $C_{20}H_{16}N_2O_5$; C, 65.93; H, 4.43; N, 7.69.

EXAMPLE 64

1-(2-Propynyl)-6,7-methylenedioxy-4-(3,4-methylenedioxyphenyl)quinazolin-2(1H)-one The title compound was prepared in a manner similar to example 63 as pale yellow solid, mp 235–240° C.; $^1$H NMR (DMSO-d$_6$) 7.28 (s, 1H), 7.04–7.22 (m, 4H), 6.24 (s, 2H), 6.15 (s, 2H), 5.07 (s, 2H), 2.70 (s, 1H); Anal. calcd. for $C_{19}H_{12}N_2O_5 \cdot (¼)H_2O$: C, 64.62; H, 3.64; N, 7.14. Found: C, 64.22; H, 4.04; N, 6.77.

EXAMPLE 65

1-Isopropyl-6,7-methylenedioxy-4-(4-dimethylaminophenyl)-quinazolin-2(1H)-one

The title compound was prepared in a manner similar to examples 10 and 25 in two steps from 1-methylenedioxyphenyl-1-isopropyl urea and 4-(dimethylamino)benzaldehyde, mp 240–245° C.; $^1$H NMR (CDCl$_3$) 7.6–7.8 (m, 2H), 7.33 (s, 1H), 7.02 (s, 1H), 6.68–6.84 (m, 2H), 6.08 (s, 2H), 5.0–5.28 (m, 1H), 2.9–3.2 (m, 6H), 1.4–1.8 (m, 6H). Anal. calcd. for C$_{20}$H$_{21}$N$_3$O$_3$(¼) H$_2$O; C, 67.43; H, 6.04; N, 11.80. Found: C, 68.36; H, 6.02; N, 11.96.

EXAMPLE 66

1-Ethyl-6,7-methylenedioxy-4-isopropyl-quinazolin-2(1H)-one

The title compound was prepared from 6-isobutyryl-3,4-(methylenedioxy)aniline and sodium cyanate followed by alkylation and obtained as a solid, mp 180–185° C. $^1$H NMR (DMSO-d$_6$) 7.61 (s, 1H), 7.27 (s, 1H), 6.20 (s, 2H), 4.0–4.3 (m, 2H), 3.5–3.8 (m, 1H), 1.0–1.4 (m, 9H).

EXAMPLE 67

6,7-Methylenedioxy-4-(3,4-methylenedioxyphenyl)-2-methylquinazoline

To a suspension of 3,4-(methylenedioxy)-2-amino-4,5-(methylenedioxy)benzophenone (200 mg, 0.65 mmol) in acetonitrile (15 mL) was added hydrogen chloride in 1,4-dioxane (5 mL). The resulting mixture was stirred at rt attached with a drying tube. After stirring for 48 h, the mixture was poured into ice water (50 mL). The resulting mixture was neutralized to pH=8 with 2 N NaOH and it was stirred for 30 min. The resulting precipitate was collected by filtration and the solid was dissolved in ethyl acetate. The solution was dried over anhydrous MgSO$_4$ the solvent was removed in vacuo. The crude product was purified by chromatography on silica gel. Elution with hexane:acetone (70:30) gave the title compound (95 mg); mp 207–210° C. $^1$H NMR (CDCl$_3$) 7.32 (s, 1H), 7.15–7.25 (m, 2H), 6.97 (d, J=8.28, 1H), 6.13 (s, 2H), 6.06 (s, 2H), 2.84 (s, 3H).

EXAMPLE 68a AND 68b

6,7-Methylenedioxy-4-(3,4-methylenedioxyphenyl)-2-(2-(dimethylamino)ethoxy)-quinazoline (a) and 1-(2-(dimethylamino)ethyl)-6,7-methylenedioxy-4-(3,4-methylenedioxyphenyl)-quinazolin-2(1H)-one (b)

The title compounds were prepared in a manner similar to example 63 with t-BuOK as the base instead of NaH. 6,7-Methylenedioxy-4-(3,4-methylenedioxyphenyl)-2-(2-(dimethylamino)ethoxy)quinazoline (a) was isolated as yellow solid (110 mg); mp 145–148° C.; $^1$H NMR (CDCl$_3$) 7.30 (s, 1H), 7.2–7.24 (m, 2H), 7.16 (s, 1H), 6.95 (d, J=8.52, 1H), 6.10 (s, 2H), 6.06 (s, 2H), 4.59 (m, 2H), 2.83 (m, 2H), 2.38 (s, 6H). C$_{20}$H$_{19}$N$_3$O$_5$; C, 62.99; H, 5.02; N, 11.02.1-(2-(dimethylamino)ethyl)-6,7-methylenedioxy-4-(3,4-methylenedioxyphenyl)-quinazolin-2(1H)-one was isolated as pale yellow solid (110 mg); mp 175–182° C. $^1$H NMR (CDCl$_3$) 7.31 (s, 1H), 7.2–7.25 (m, 2H), 7.16 (s, 1H), 6.95 (d, J=8.04, 1H), 6.10 (s, 2H), 6.06 (s, 2H), 4.61 (m, 2H), 2.87 (m, 2H), 2.41 (s, 6H); Anal. calcd. for C$_{20}$H$_{99}$N$_3$O$_5$: C, 62.99; H, 5.02; N, 11.02. Found: C, 62.78; H, 4.94; N, 10.73.

EXAMPLE 69

6,7-Methylenedioxy-4-(3,4-methylenedioxyphenyl)-2-phenylquinazoline

The title compound was prepared in a manner similar to example 67 as yellow solid, mp 225–230° C.; $^1$H NMR (CDCl$_3$) 8.60 (d, J=6.8, 1H), 7.49 (s, 1H), 7.42 (s, 1H), 7.35 (d, J=3.0, 1H), 7.32 (s, 1H), 7.2–7.9 (m, 5H), 7.0 (d, J=7.98, 1H), 6.16 (s, 2H), 6.09 (s, 2H); C$_{22}$H$_{14}$N$_2$O$_4$; C, 71.35; H, 3.81; N, 7.56.

EXAMPLE 70

6,7-Methylenedioxy-4-(3,4-methylenedioxyphenyl) quinazoline

To a suspension of 3,4-(methylenedioxy)-2-amino-4,5-(methylenedioxy)benzophenone (100 mg, 0.32 mmol) in formamide (1.0 mL) was added formic acid (0.5 mL). The resulting mixture was refluxed under argon for 45 min, cooled to rt, poured into ice water (10 mL), and stirred for 30 min. The resulting precipitate was collected by filtration and the solid was dissolved in ethyl acetate. The solution was washed with water and brine, dried over anhydrous MgSO$_4$ and the solvent was removed in vacuo. The crude product was purified by chromatography on silica gel. Elution with hexane:acetone (70:30) gave the title compound (52 mg); mp 180–185° C. $^1$H NMR (DMSO-d$_6$) 9.05 (s,1H), 7.40 (s, 1H), 7.33 (s,1H), 7.28 (s,1H), 7.23 (d, J=7.98, 1H), 7.10 (d, J=7.98, 1H), 6.25 (s, 2H), 6.10 (s, 2H). Anal. calcd. for C$_{16}$H$_{10}$N$_2$O$_4$: C, 65.31; H, 3.43; N, 9.52. Found: C, 65.07; H, 3.59; N, 9.30.

EXAMPLE 71

2-(Dimethylamino)-6,7-methylenedioxy-4-(3,4-methylenedioxyphenyl)quinazoline To a solid of 2-chloro-6,7-methylenedioxy-4-(3,4-methylenedioxyphenyl)quinazoline (50 mg, 0.15 mmol) was added dimethylamine in methanol (2.0 M, 3 mL). The resulting mixture was refluxed under argon for 2 h, and the precipitate in the reaction mixture was collected by filtration. The precipitate was washed with hexane and dried to give 2-(dimethylamino)-6,7-methylenedioxy-4-(3,4-methylenedioxyphenyl)-quinazoline (40 mg); mp 200–206° C. $^1$H NMR (DMSO-d$_6$) 7.23 (s, 1H), 7.18 (s, 1H), 7.13 (d, J=7.14 Hz, 1H), 7.07 (d, J=7.14, 1H), 6.95 (s, 1H), 6.13 (s, 6H), 3.18 (s, 6H).

EXAMPLE 72

2-Methoxy-6,7-methylenedioxy-4-(3,4-methylenedioxyphenyl)quinazoline

The title compound was prepared in a manner similar to example 71 as yellow solid, mp 216–223° C.; $^1$H NMR (DMSO-d$_6$) 7.23 (m, 4H), 7.10 (d, J=8.1, 1H), 6.23 (s, 2H), 6.15 (s, 2H), 3.98 (s, 3H); Anal. calcd. for C$_{11}$H$_{12}$N$_2$O$_5$(¼) H$_2$O: C, 62.04; H, 3.65; N, 8.52. Found: C, 62.15; H, 3.46; N, 8.31.

EXAMPLE 73a AND 73b

2-(1-Methyl-2-(dimethylamino)ethoxy)-6,7-methylenedioxy-4-(3,4-methylenedioxyphenyl) quinazoline (a) and J-(]-methyl-2-(dimethylamino) ethoxy)-6,7-methylenedioxy-4-(3,4-methylenedioxyphenyl)quinazoline-2(1H)-one (b)

The title compounds were prepared in a manner similar to example 68. 2-(1-Methyl-2-(dimethylamino)ethoxy)-6,7-methylenedioxy-4-(3,4-methylenedioxyphenyl)quinazoline was isolated as yellow solid, mp 172–175° C.; $^1$H NMR (DMSO-d$_6$) 7.24 (m, 4H), 7.10 (d, J=7.95, 1H), 6.23 (s, 2H), 6.15 (s, 2H), 4.45 (m, 1H), 4.25 (m, 2H), 2.28 (s, 6H), 1.05

(d, J=6.6, 3H). Anal. calcd. for $C_{21}H_{21}N_3O_5$: C, 63.79; H, 5.35; N, 10.63. Found: C, 63.55; H, 5.31; N, 10.63. 1-(1-methyl-2-(dimethylamino)ethoxy)-6,7-methylenedioxy-4-(3,4-methylenedioxyphenyl)quinazoline-2(1H)-one was isolated as a solid, mp 160–165° C.; $^1$H NMR (CDCl$_3$) 7.1–7.35 (m, 3H), 6.85–7.0 (m, 2H), 6.11 (s, 2H), 6.06 (s, 2H), 4.5–4.65 (m, 1H), 4.0–4.2 (m, 2H), 2.37 (s, 6H), 1.07 (s, 3H).

EXAMPLE 74a AND 74b 2-(2-Aminoethoxy)-6,7-methylenedioxy-4-(3,4 methylenedioxyphenyl)quinazoline (a) and 1-(2-aminoethyl)-6,7-methylenedioxy-4-(3,4-methylenedioxyphenyl)quinazoline-2(1H)-one (b)

The title compounds were prepared in a manner similar to example 68. 2-(2-Aminoethoxy)-6,7-methylenedioxy-4-(3,4-methylenedioxyphenyl) quinazoline was isolated as yellow solid, mp 162–167° C.; $^1$H NMR (CDCl$_3$) 7.14 (m, 3H), 6.96 (m, 2H), 6.06 (s, 6H), 5.58 (m, 2H), 3.88 (m, 2H), 3.67 (m, 2H); Anal. calcd. for $C_{11}H_{15}N_3O_5$: C, 61.19; H, 4.28; N, 11.89. Found: C, 61.28; H, 4.52; N, 10.98. 1-(2-Aminoethyl)-6,7-methylenedioxy-4-(3,4-methylenedioxyphenyl)quinazoline-2(1H)-one was isolated as pale yellow solid, mp 115–120° C. $^1$H NMR (CDCl$_3$) 7.25 (m, 3H), 6.93 (m, 2H), 6.11 (s, 2H), 6.07 (s, 2H), 4.34 (m, 2H), 3.14 (m, 2H), 1.53 (s, 2H).

EXAMPLE 75

6,7-Methylenedioxy-4-(3,4-methylenedioxyphenyl) quinazolin-2(1H)-one 3,4-(Methylenedioxy)-2-amino-4',5'-(methylenedioxy) benzophenone 15.0 g, 52.63 mmol) was dissolved in AcOH (250 mL) by heating, then sodium cyanate (4.1 g, 63.16 mmol) and water (25 mL) was added. The resulting mixture was stirred at rt for 18 h, then excess water (120 mL) was added. The precipitate was collected by filtration, washed with water, acetone, and dried to give 6,7-methylenedioxy-4-(3,4-methylenedioxyphenyl)-quinazolin-2(1H)-one as yellow solid (15.7 g); mp>300° C. $^1$H NMR (DMSO) 7.18 (s, 1H), 7.14 (d, J=9.12, 1H), 7.07 (d, J=7.95, 1H), 7.04 (s, 1H), 6.82 (s, 1H), 6.16 (s, 2H), 6.14 (s, 2H), 1.90 (s, 1H). Anal. calcd. for $C_{16}H_{10}N_2O_5$(¼)H$_2$O: C, 60.99; H, 3.34; N, 8.90. Found: C, 60.92; H, 3.14; N, 8.47.

EXAMPLE 76a AND 76b 1-(2-Pyrrolidinylethyl)-6,7-methylenedioxy-4(3,4-methylenedioxyphenyl)quinazolin-2(1H)-one (a) and 2-(2-pyrrolidinylethoxy)-6,7-methylenedioxy-4 (3,4-methylenedioxyphenyl)quinazoline (b)

The title compounds were prepared in a manner similar to example 68. 1-(2-pyrrolidinylethyl)-6,7-methylenedioxy-4-(3,4-methylene-dioxyphenyl)-quinazolin-2(1H)-one was isolated as yellow solid (50 mg); mp 225–230° C. $^1$H NMR (DMSO-d$_6$) 7.30 (s, 1H), 7.0–7.25 (m, 3H), 6.22 (s, 2H), 6.15 (s, 2H), 4.3–4.45 (m, 2H), 4.0–4.19 (m, 2H), 2.65–2.85 (m, 4H), 1.72 (s, 4H). $C_{22}H_{21}N_3O_5$; C, 64.86; H, 5.20; N, 10.31. 2-(2-Pyrrolidinylethoxy)-6,7-methylenedioxy-4-(3,4-methylenedioxyphenyl)quinazoline was isolated as pale yellow solid (45 mg); mp 183–190° C. $^1$H NMR (DMSO-d$_6$) 7.20–7.30 (m, 3H), 7.0–7.15 (d, J=7.9, 1H), 6.23 (s, 2H), 6.15 (s, 2H), 4.53 (m, 2H), 3.05 (m, 2H), 2.76 (s, 4H), 1.75 (s, 4H).

EXAMPLE 77a AND 77b

2-[2-(Diethylamino)ethoxy]-4-(3,4-methylenedioxyphenyl)-6,7-methylenedioxyquinazoline (a) and 1-[2-(diethylamino)ethyl]-4-(3,4-methylenedioxyphenyl)-6,7-methylenedioxyquinazolin-2(1H)-one (b)

The title compounds were prepared in a manner similar to example 68. 2-[2-(Diethylamino)ethoxy]-4-(3,4-methylenedioxyphenyl)-6,7-methylene dioxyquinazoline was isolated as a solid. $^1$H NMR (DMSO-d$_6$) 0.99–0.95 (m, 6H), 2.51–2.62 (m, 4H), 2.76–2.83 (m, 2H), 4.38–4.44 (m, 2H), 6.15 (s, 2H), 6.23 (s, 2H), 7.09–7.24 (m, 5H). $C_{22}H_{23}N_3O$: C, 64.54; H, 5.66; N, 10.26. 1-[2-(Diethylamino)ethyl]-4-(3,4-methylenedioxyphenyl)-6,7-methylenedioxyquinazolin-2(1H)-one was isolated as a yellow solid (20 mg). $^1$H NMR (DMSO-d$_6$) 0.89–0.93 (m, 6H), 2.48–2.58 (m, 4H), 2.61–2.70 (m, 2H), 4.22–4.28 (m, 2H), 6.14 (s, 2H), 6.21 (s, 2H), 7.09–7.25 (m, 5H). Anal. calcd. For $C_{22}H_{23}N_3O_5$: C, 64.54; H, 5.66; N, 10.26. Found: C, 64.36; H, 5.67; N, 10.19.

EXAMPLE 78a AND 78b 4-(3,4-Methylenedioxyphenyl)-6,7-methylenedioxy-2-(2-morpholinylethoxy)-quinazoline (a) and 4-(3,4-methylenedioxyphenyl)-6,7-methylenedioxy-1-(2-morpholinylethyl)-quinazolin-2(1H)-one (b)

The title compounds were prepared in a manner similar to example 68. 4-(3,4-Methylenedioxyphenyl)-6,7-methylenedioxy-2-(2-morpholinylethoxy)-quinazoline was isolated as a solid. $^1$H NMR (DMSO-d$_6$) 0.99–0.95 (m, 6H), 2.51–2.62 (m, 4H), 2.76–2.83 (m, 2H), 4.38–4.44 (m, 2H), 6.15 (s, 2H), 6.23 (s, 2H), 7.09–7.24 (m, 5H). $C_{22}H_{23}N_3O_5$ C, 64.54; H 5.66: N 10.26. 4-(3,4-Methylenedioxyphenyl)-6,7-methylenedioxy-1-(2-morpholinyl-ethyl)-quinazolin-2(1H)-one was isolated as a yellow solid. $^1$H NMR (DMSO-d$_6$) 0.89–0.93 (m, 6H), 2.48–2.58 (m, 4H), 2.61–2.70 (m, 2H), 4.22–4.28 (m, 2H), 6.14 (s, 2H), 6.21 (s, 2H), 7.09–7.25 (m, 5H). Anal. calcd. $C_{22}H_{23}N_3O_5$ C, 64.54; H, 5.66; N, 10.26. Found: $C_{22}H_{23}N_3O_5$.(2.25H$_2$O): C, 62.02; H, 5.17; N, 9.83.

EXAMPLE 79

2-Amino-4,5-methylenedioxy-(3',4'-methylenedioxy)benzophenone a) (3,4-Methylenedioxy)-trifluoroacetanilide. To a solution of 3,4-(methylenedioxy)aniline (15 g, 108.4 mmol) and TEA (21.3 mL) in toluene (150 mL) at 0° C. under argon was added dropwise trifluoroacetic anhydride (21 mL, 148 mmol) in toluene (23 mL). The reaction mixture was then stirred at rt for 3.75 h. The reaction mixture was diluted with ethyl acetate (50 mL), washed with water (2×10 mL), sodium bicarbonate (2×20 mL), dried over anhydrous MgSO$_4$, and concentrated to yield (28.6 g) of a crude purple solid.

b) 4,5-Methylenedioxy-2-trifluoroacetamido-(3',4'-methylenedioxy)benzophenone. A solution of piperonyloyl chloride (7.9 g, 43 mmol) in dry dichloromethane (70 mL) at 0° C. was treated with tin (IV) chloride solution (1M in CH$_2$Cl$_2$, 64.5 mL, 64.5 mmol) dropwise. Upon complete addition, the reaction mixture was allowed to warm slowly to rt. The reaction mixture was then treated with (3,4-methylenedioxy)trifluoroacetanilide and heated to reflux for 16.5 h. The reaction mixture was cooled to rt and concentrated. The resulting residue was poured into ice water (300 mL) and stirred for 1 h. The resulting solid was vacuum filtered and washed with water. The solid was dissolved in ethyl acetate and the solution was washed with saturated sodium bicarbonate solution (10 mL per washing) until gas no longer formed. The organic layer was dried over anhydrous MgSO$_4$ and concentrated to yield a crude yellow product (6.69 g).

c) 2-Amino-4,5-methylenedioxy-(3',4'-methylenedioxy) benzophenone. A solution of 4,5-methylenedioxy-2- trifluoroacetamido-(3',4'-methylenedioxy)benzophenone (5 g, 13.12 mmol) in methanol at 50° C. was treated with a solution of potassium carbonate (3.63 g, in 30 mL water) and stirred for 5 h. The reaction mixture was cooled in an ice bath for 20 min. The resulting solid was filtered and then dissolved in ethyl acetate, dried over anhydrous $MgSO_4$, and concentrated to give a crude yellow product (2.8 g).

EXAMPLE 80

2-Ethyl-4-(3,4-methylenedioxyphenyl)-6,7-methylenedioxyquinazoline

The title compound was prepared in a manner similar to example 67 as a yellow solid. $^1H$ NMR (DMSO-$d_6$) 1.31–1.36 (m, 3H), 2.92–2.99 (m, 2H), 6.14 (s, 2H), 6.25 (s, 2H), 7.08–7.32 (m, 5H).

EXAMPLE 81

2-Benzyl-4-(3,4-methylenedioxyphenyl)-6,7-methylenedioxy)quinazoline

The title compound was prepared in a manner similar to example 67 as clear crystals. $^1H$ NMR (DMSO-$d_6$) 4.27 (s, 2H), 6.14 (s, 2H), 6.26 (s, 2H), 7.08–7.37 (m, 10H). Anal. calcd. for $C_{23}H_{16}N_2O_4$: C, 71.87: H, 4.20; N, 7.29. Found: C, 71.73; H, 4.08; N, 7.25.

EXAMPLE 82

4-(3,4-Methylenedioxyphenyl)-6,7-methylenedioxy-2-pentyl-quinazoline

The title compound was prepared in a manner similar to example 67 as clear crystals. $^1H$ NMR (CDCl$_3$) 0.89–0.94 (m, 3H), 1.35–1.51 (m, 4H), 1.89–1.93 (m, 2H), 3.02–3.07 (m, 2H), 6.06 (s, 2H), 6.12 (s, 2H), 6.96–6.98 (m, 1H), 7.19–7.32 (m, 4H).

EXAMPLE 83

2-Chloromethyl-4-(3,4-methylenedioxyphenyl)-6,7-methylenedioxyquinazoline

The title compound was prepared in a manner similar to example 67 as colorless crystals. $^1H$ NMR (CDCl$_3$) 4.86 (s, 2H), 6.07 (s, 2H), 6.17 (s, 2H), 6.97–7.39 (m, 5H). Anal. calcd. $C_{17}H_{11}ClN_2O_4$, C, 59.58; H, 3.24; Cl, 10.34; N, 8.17. $C_{17}H_{11}ClN_2O_4$.(2.25$H_2O$).

EXAMPLE 84

2-(2-Chloroethyl)-6,7-methylenedioxy-4-(3,4-methylenedioxyphenyl)quinazoline The title compound was prepared in a manner similar to example 67 as a yellow solid. $^1H$ NMR (CDCl$_3$) 3.51–3.55 (m, 2H), 4.12–4.17 (m, 2H), 6.08 (s, 2H), 6.14 (s, 2H), 6.69–7.36 (m, 5H).

EXAMPLE 85

2-(3-Chloropropyl)-4-(3,4-methylenedioxyphenyl)-6,7-methylenedioxyquinazoline The title compound was prepared in a manner similar to example 67 as a yellow solid. $^1H$ NMR (CDCl$_3$) 2.39–2.44 (m, 2H), 3.19–3.24 (m, 2H), 3.68–3.72 (m, 2H), 6.07 (s, 2H), 6.13 (s, 2H), 6.95–7.33 (m, 5H).

EXAMPLE 86

2-(2-Dimethylaminoethyl)-4-(3,4-methylenedioxyphenyl)-6,7-methylenedioxyquinazoline The title compound was prepared in a manner similar to example 67 as a yellow solid. $^1H$ NMR (CDCl$_3$) 2.36 (s, 6H), 2.95–3.00 (m, 2H), 3.24–3.29 (m, 2H), 6.06 (s, 2H), 6.12 (s, 2H), 6.95–7.32 (m, 5H). Anal. calcd. $C_{20}H_{19}N_3O_4$, C, 65.74; H, 5.24; N, 11.50. Found: C, 65.24; H, 5.12; N, 11.03.

EXAMPLE 87

2-(3-Dimethylaminopropyl)-4-(3,4-methylenedioxyphenyl)-6,7-methylenedioxyquinazoline The title compound was prepared in a manner similar to example 67 as a yellow solid. $^1H$ NMR (CDCl$_3$) 2.04–2.16 (m, 2H), 2.26 (s, 6H), 2.39–2.42 (m, 2H), 3.04–3.09 (m, 2H), 6.07 (s, 2H), 6.13 (s, 2H), 6.92–7.41 (m, 5H). Anal. calcd. $C_{21}H_{21}N_3O_4$; C, 66.48; H, 5.58; N, 11.07. Found: C, 66.22; H, 5.63; N, 10.97.

EXAMPLE 88

2-(Imidazol-1-yl)methyl-6,7-methylenedioxy-4-(3,4-methylenedioxyphenyl)quinazoline The title compound was prepared in a manner similar to example 95 as a yellow solid, mp182–5° C. Anal. calcd. $C_{20}H_{14}N_4O_4$; C, 64.17; H, 3.77; N, 14.97. Found: C, 63.86; H, 3.63; N, 14.60.

EXAMPLE 89

1-Isopropyl-4-(3,4-methlylenedioxyphenyl)-8-methyl-7-ox-o-3,4-dihydro-oxazol[5,4-g]quinazolin-2(1H)-one a) 5-Amino-3-methyl-2(3H)-benzoxazolone. A mixture of 7.3 g (37.6 mmol) of 3-methyl-5-nitro-2(3H)-benzoxazolone, 0.5 g of 5% Pd/C and 200 ml of glacial acetic acid was hydrogenated on the Parr at ca. 40 psi for 1 h. The catalyst was removed by filtration of the mixture through Celite rinsing with water. The filtrate was concentrated in vacuo to leave 6.25 g (>100% of theory) of product (single spot on TLC) as a solid.

b) 5-(Isopropylamino)-3-methyl-2(3H)-benzoxazolone. A suspension of 6.24 g (37.6 mmol) of the above product in 60 ml of methanol, 60 ml of THF, 10 ml of acetic acid and 3.6 ml (ca. 50 mmol) of acetone was stirred and cooled in an ice bath. To this mixture was added 3.1 g (49 mmol) of sodium cyanoborohydride. After stirred for 45 min, a further 3.1 g of sodium cyanoborohydride was added, and the reaction mixture was allowed to stir overnight at rt. The clear tan solution resulted (TLC (EtOAc) single spot) was concentrated in vacuo. The residue was treated with 50 ml of water and 150 ml of 2N sodium hydroxide to give a strongly alkaline mixture. The precipitated solid was collected and rinsed with water to give 13.9 g of very wet tan product.

c) 5-(N-Isopropylureido)-3-methyl-2(3H)-benzoxazolone. To a stirred solution of the above crude amine in 100 ml of glacial acetic acid was added 3.3 g (40.7 mmol) of potassium cyanate, and the reaction mixture was stirred at rt for 5 days. It was concentrated in vacuo to 33 g and diluted with 100 ml of water. After standing for 1 h the solid was collected, rinsed with water, and allowed to dry overnight to give 6.14 g (65%) of product, mp 198–201°.

From the filtrate concentrated in vacuo and diluted with water was obtained a second crop of 1.26 g (13%) of crude product, mp 183–190°. Both crops were quite pure by TLC (EtOAc or 10% MeOH/methylene chloride).

d) 1-Isopropyl-4-(3,4-methylenedioxyphenyl)-8-methyl-7-oxo-3,4-dihydro-oxazol[4,5-g]quinazolin-2(1H)-one. A mixture of 2.5 g (10 mmol) of the above urea, 1.8 g (12 mmol) of piperonal, 75 ml of benzene and 5 drops of methanesulfonic acid was refluxed with a Dean-Stark water separator for 18 h. The reaction mixture has turned orange and there was white solid in the condenser. The reaction mixture was cooled. The orange solid was collected and rinsed with ether to give 2 g (50%) of crude product, mp 215–220°. TLC (EtOAc) showed one main spot with some yellow at the origin.

EXAMPLE 90

1-Isopropyl-4-(3,4-methylenedioxyphenyl)-8-methyl-7-oxo-oxazol[5,4-g]quinazolin-2(1H)-one To a stirred solution of 1.14 g (3 mmol) of 1-isopropyl-4-(3,4-methylenedioxyphenyl)-8-methyl-7-oxo-3,4-dihydro-oxazol[4,5-g]quinazolin-2(1H)-one in 30 ml of dioxane was added dropwise during 5 min a solution of 0.569 g (3.6 mmol) of potassium permanganate in 30 ml of water. The mixture was stirred for 5 min and then treated with 3 ml of formalin. The precipitated manganese dioxide was removed by filtration through Celite and washed with acetone. The combined filtrates were concentrated in vacuo to about 50 ml. A gum separated which solidified. The solid was collected and rinsed with water to give 1.16 g of product as a pale yellow solid, mp 100° with foaming.

EXAMPLE 91

6,7-Methylenedioxy-4-(3,4-methylenedioxyphenyl) quinazoline 3-oxide

A mixture of 3,4-methylenedioxy-3',4'-methylenedioxybenzophenone oxime (100 mg, 0.33 mmol) and trimethyl orthoformate (2 mL) was heated at 70° C. for 15 h. After cooling, the separated solid was collected by filtration, washed with hexane, and air dried to give the title compound as an off white solid (30 mg); mp 210–212° C. $^1$H NMR δ (CDCl$_3$) 8.99 (s 1H), 7.42 (s, 1H), 7.15 (s, 1H), 7.12 (d, 1H, J=8.4 Hz), 7.00 (d, 1H, J=8.4 Hz), 6.72 (s 1H), 6.25 (s, 2H), 6.14 (s, 2H).

EXAMPLE 92

2-Methyl-6,7-methylenedioxy-4-(3,4-methylenedioxyphenyl)quinazoline 3-oxide

A mixture of 3,4-methylenedioxy-3',4'-methylenedioxybenzophenone oxime (150 mg, 0.5 mmol) and triethyl orthoacetate (1 mL) was heated at 120° C. for 3 h. After cooling, the separated solid was collected by filtration, washed with hexane, and air dried to give the title compound as off white solid (35 mg); mp 264–272° C.

EXAMPLE 93

2-Ethyl-6,7-methylenedioxy-4-(3,4-methylenedioxyphenyl)quinazoline 3-oxide

A mixture of 3,4-methylenedioxy-3',4'-methylenedioxybenzophenone oxime (100 mg, 0.33 mmol) and triethyl orthopropionate (1 mL) was heated at 120° C. for 3 h. After cooling, the separated solid was collected by filtration, washed with hexane, and air dried to give the title compound as off white solid (37 mg); mp 254–260° C. $^1$H NMR δ (CDCl$_3$) 7.28 (s, 1H), 7.05 (s, 1H), 7.00 (d, 1H, J=7 Hz), 6.98 (d, 1H, J=7 Hz), 6.77 (s 1H), 6.12 (s, 2H), 6.07 (s, 2H), 3.25 (m, 2H), 1.45 (m, 3H).

EXAMPLE 94

2-Chloromethyl-6,7-methylenedioxy-4-(3,4-methylenedioxyphenyl)quinazoline 3-oxide A mixture of 3,4-methylenedioxy-3',4'-methylenedioxybenzophenone oxime (100 mg, 0.33 mmol) and 2-chloro-1,1,1-trimethoxyethane (1 mL) was heated at 120° C. for 3 h. After cooling, the separated solid was collected by filtration, washed with hexane, and air dried to give the title compound as off white solid (60 mg); mp 210–215° C. $^1$H NMR δ (CDCl$_3$) 7.34 (s, 1H), 7.08 (s, 1H), 7.00 (s, 2H), 6.84 (s 1H), 6.16 (s, 2H), 6.08 (s, 2H), 5.07 (s, 1H).

EXAMPLE 95

2-(Imidazol-1-yl)methyl-6,7-methylenedioxy-4-(3,4-methylenedioxyphenyl) quinazoline-3-oxide To a suspension of 2-chloromethyl-6,7-methylenedioxy-4-(3,4-methylenedioxyphenyl)quinazoline-3-oxide (192 mg, 0.53 mmol), in dry DMF (3 mL), was added imidazole (142 mg, 2.1 mmol). The mixture was stirred at 85° C. for 1.5 h and left at rt for 15 h. DMF was removed and the mixture was poured into ice-water. The precipitated solid was extracted with EtOAc. The organic layer was washed with water, brine and dried over anhydrous MgSO4. It was filtered and the solvent was removed to yield the title compound as off white solid (100 mg); mp 212–217° C. $^1$H NMR (CDCl$_3$) 7.76 (s, 1H), 7.00–7.21 (m, 5H), 6.80 (s 1H), 6.13 (s, 2H), 6.08 (s, 2H), 5.63 (s, 2H).

EXAMPLE 96

2-(Pyrrolidin-1-yl)methyl-6,7-methylenedioxy-4-(3,4-methylenedioxyphenyl)quinazoline-3-oxide To a suspension of 2-chloromethyl-6,7-methylenedioxy-4-(3,4-methylenedioxyphenyl)quinazoline-3-oxide (200 mg, 0.55 mmol), in MeOH (5 mL), was added pyrrolidine (0.4 mL). The mixture was stirred at 65° C. for 1.5 h. DMF (6 mL) was added and the heating was continued at 60° C. for 15 h. After cooling, the separated solid was collected by filtration, washed with hexane, and air dried to give the title compound as off white solid (175 mg). The crude product was purified by column chromatography on silica gel (CH$_2$Cl$_2$:MeOH 95:5); mp 194–202° C. $^1$H NMR (CDCl$_3$) 7.39 (s, 1H), 6.90–7.06 (m, 4H), 6.78 (s 1H), 6.11 (s, 2H), 6.08 (s, 2H), 4.25 (s, 2H), 2.87 (bs, 4H), 1.91 (bs, 4H).

EXAMPLE 97

2-Dimethylaminomethyl-6,7-methylenedioxy-4-(3,4-methylenedioxyphenyl) quinazoline-3-oxide To a suspension of 2-chloromethyl-6,7-methylenedioxy-4-(3,4-methylenedioxyphenyl)quinazoline-3-oxide (200 mg, 0.55 mmol), in THF (6 mL), was added dimethylamine (2M in THF, 2 mL, 4 mmol). The mixture %-as stirred at 65° C. for 2 h. After cooling, the solvent was evaporated and the residue was purified by column chromatography on silica gel (hexane:acetone 4:1); mp 205–210° C. $^1$H NMR (CDCl$_3$) 7.41 (s, 1H), 6.90–7.06 (m, 4H), 6.78 (s 1H), 6.11 (s, 2H), 6.08 (s, 2H), 4.05 (s, 2H), 2.52 (s, 6H).

EXAMPLE 98

1-Isopropyl-4-(3,4-methylenedioxyphenyl)-8-benzyl-7-oxo-oxazol[5,4-g]quinazolin-2(1H)-one a) 5-(2-Propylamino)-2(3H)-benzoxazolone. To a Parr bottle containing 5-nitro-2(3H)-benzoxazolone (8.08 g, 44.9 mmol) was added acetic acid (230 mL) and then Ar was bubbled for 10 min. Palladium on C (10%. 0.5 g) was added carefully and the hydrogenation was carried out under 45 psi of hydrogen on a Parr hydrogenator. The reaction was complete within 2 h, and mixture was filtered through a pad of Celite. The solvent was then removed in vacuo, and 5-amino-2(3H)-benzoxazolone was obtained as a pale solid. Without further purification, to this solid was added MeOH (70 mL), THF (70 mL), acetic acid (12 mL), and acetone (4.15 mL). The mixture was then cooled to 0° C., and NaCNBH$_3$ (3.6 g) was added slowly. The reaction mixture became a brown colored solution within 20 min. The reaction mixture was concentrated in vacuo, and water (60 mL) was added along with NaOH (2 N) to bring the pH to around 7. The product was then extracted with EtOAc (2×350 mL) and purified by flash chromatography (CH$_2$CH$_2$:MeOH:TEA=49:1:0.15, R$_f$=0.17) to result in the product (5.32 g, 62%). $^1$H NMR (300 MHz, CDCl$_3$) δ 6.98 (d, J=8.7 Hz, 1H), 6.34–6.27 (m, 2H), 3.55 (p, J=6.3 Hz, 1H), 3.43 (bs, 1H), 1.20 (d, J=6.3 Hz, 6H).

b) N-isopropyl-5-carbamido-2(3H)-benzoxazolone. To a solution of 5-(2-propylamino)-2(3H)-benzoxazolone (2.0 g, 10.4 mmol) in acetic acid (30 mL) was added water (1.5 mL) and KOCN (0.975 g, 12 mmol). A milky white solid started to form and the starting material disappeared within 5 h. The solvent was removed in vacuo and the residue was treated with water (50 mL). The product was obtained by filtration as a near white solid (2.4 g, 98%). $^1$H NMR (300 MHz, DMSO) δ 7.29 (d, J=8.7 Hz, 1H), 6.83 (m, 2H), 5.27 (bs, 2H) 4.59 (p, J=6.6 Hz, 1H), 0.93 (d, J-6.6 Hz, 6H).

c) N-isopropyl-3-benzyl-5-carbamido-2(3H)-benzoxazolone. To a suspension of N-isopropyl-5-carbamido-2(3H)-benzoxazolone (200 mg, 0.85 mmol) in DMF (30 mL) under Ar was added NaH (60%. 40 mg, 1.0 mmol) and a clearer mixture resulted. Benzyl bromide (0.25 mL, 2.0 mmol) was added and the mixture obtained was stirred at room temperature for 12 h. Water (30 mL) added and the product was extracted with EtOAc (3×30 mL). The combined extracts were washed with brine (2×30 mL) and dried over Na$_2$SO$_4$. The solvent was removed in vacuo and the product (175 mg, 63%) seas purified by flash chromatography (2.5% MeOH, and 0.25% TEA in CH$_2$Cl$_2$). $^1$H NMR (300 MHz, CDCl$_3$) δ 7.34 (m, 5H), 7.23 (d, J=8.7 Hz, 1H), 6.91 (dd, J=2.1, 8.7 Hz, 1H), 6.60 (d, J=2.1 Hz, 1H), 5.01 (s, 2H), 4.79 (p, J=6.6 Hz, 1H), 4.07 (s, 2H), 0.91 (d, J=6.6 Hz, 6H).

d) 1-Isopropyl-4-(3,4-methylenedioxyphenyl)-8-benzyl-7-oxo-1,2,3,4-tetrahydro-oxazol[5,4-g]quinazolin-2(1H)-one. To a suspension of N-isopropyl-3-benzyl-1-5-carbamido-2(3H)-benzoxazolone (155 mg. 0.48 mmol) in benzene (30 mL) under Ar was added piperonal (86 mg, 0.58 mmol), and MeSO$_3$H (1 drop). The mixture obtained was heated to reflux under Dean-Stark trap for 5.5 h. It was cooled to room temperature, and EtOAc (40 mL) was added. The solution was washed with NaHCO$_3$ solution (dilute, 20 mL) and brine (30 mL) and dried over Na$_2$SO$_4$. The solvent A-as then removed in vacuo and the pure product (32 mg, 15%) was obtained by chromatography (0.7%, MeOH, 0.07% TEA in CH$_2$Cl$_2$). m.p., 100–105° C. $^1$H NMR (300 MHz, CDCl$_3$) δ 7.37 (m, 5H), 6.74 (m, 2H), 6.62 (s, 1H), 6.44 (s, 1H), 5.97 (s, 2H), 5.27 (s, 1H), 5.00 (s, 1H), 4.40 (p, J=6.6 Hz, 1H), 1.41 (d, J=6.9 Hz, 3H), 1.37(d, J=6.9 Hz, 3H).

e) 1-Isopropyl-4-(3,4-methylenedioxyphenyl)-8-benzyl-7-oxo-oxazol[5,4-g]quinazolin-2(1H)-one To a solution of 1-Isopropyl-4-(3,4-methylenedioxyphenyl)-8-benzyl-7-oxo-1,2,3,4-tetrahydro-oxazol[5,4-g]quinazolin-2(1H)-one (25 mg, 0.055 mmol) in THF (5 mL) was added KMnO$_4$ aqueous (excess). The reaction was complete in 1 h. Formaldehyde (37%) solution was added (0.1 mL) and the mixture was filtered through Celite, then rinsed with acetone. The solvent was then removed and chromatographic purification resulted in the pure product (8 mg, 32%), m.p., 230–235° C. $^1$H NMR (300 MHz, CDCl$_3$) δ 7.63 (s, 1H), 7.40 (m, 5H), 7.21 (m, 2H), 6.86 (d, J=8.7 Hz, 1H), 6.07 (s, 2H), 5.11 (s, 2H), 5.10 (m, 1H), 1.47 (d, J=7.2 Hz, 6H).

EXAMPLE 99

1-Isopropyl-4-(3,4-methylenedioxyphenyl)-8-ethyl-7-oxo-oxazol[5,4-g]quinazolin-2(1H)-one a) N-isopropyl-3-ethyl-5-carbamido-2(3H)-benzoxazolone. The title compound was synthesized by a similar method as for example 98c. The purification was carried out with flash chromatography (20% acetone in CH$_2$Cl$_2$), and product was obtained as a white solid (2.6 g from 3.0 g N-isopropyl-5-carbamido-2(3H)-benzoxazolone, 77%). $^1$H NMR (300 MHz, CDCl$_3$) δ 7.25 (d, J=8.7 Hz, 1H), 6.95 (dd, J=1.8, 8.7 Hz, 1H), 6.82 (d, J=1.8 Hz, 1H), 4.87 (p, J=6.9 Hz, 1H), 4.17 (bs, 2H), 3.90 (q, J=6.9 Hz, 2H), 1.39 (t, J=6.9 Hz, 3H), 1.07 (d, J=6.9 Hz, 6H).

b) 1-Isopropyl-4-(3,4-methylenedioxyphenyl)-8-ethyl-7-oxo-1,2,3,4-tetrahydro-oxazol[5,4-g]quinazolin-2(1H)-one. The title compound was synthesized by a similar method as for example 98d. The product (1.2 g, 31%) was obtained by chromatography (1% MeOH in CH$_2$Cl$_2$), m.p., 215–219° C. $^1$H NMR (300 MHz, CDCl$_3$) δ 6.78 (m, 2H), 6.65 (d, J=6.6 Hz, 1H), 5.98 (s, 2 H), 5.32 (s, 1H), 5.04 (s, 1H), 4.48 (p, J=6.6 Hz, 1H), 3.88 (q, J=7.2 Hz, 2H), 1.61 (t, J=7.2 Hz, 6H), 1.39 (t, J=7.2 Hz, 3H).

c) 1-Isopropyl-4-(3,4-methylenedioxyphenyl)-8-ethyl-7-oxo-oxazol[5,4-g]quinazolin-2(1H)-one. To a solution of 1-Isopropyl-4-(3,4-methylenedioxyphenyl)-8-ethyl-7-oxo-1,2,3,4-tetrahydro-oxazol[5,4-g]quinazolin-2(1H)-one (1.0 g, 2.53 mmol) in dioxan (100 mL) was added KMnO$_4$ aqueous solution (excess). The reaction was complete in 1 h. Formaldehyde (37%) solution was added (5 mL) and the mixture was filtered through Celite rinsed with acetone. The solvent was then removed in vacuo, and a light yellow precipitate was formed upon treatment of the residue with water (100 mL). The product was obtained through filtration (875 mg, 88%), m.p., 215–235° C.; $^1$H NMR (300 MHz, CDCl$_3$) δ 7.64 (s, 1H), 7.24 (m, 2H), 7.01 (s, 1H), 6.95 (d, J=8.8 Hz, 1H), 6.08 (s, 2H), 5.05 (m, 1H), 4.00 (q, J=7.2 Hz, 2H), 1.72 (d, J=6.9 Hz, 6H), 1.46 (t, J=7.2, Hz, 3H).

EXAMPLE 100

1-Isopropyl-4-(3,4-ethylenedioxyphenyl)-8-ethyl-7-oxo-oxazol[5,4-g]quinazolin-2(1H)-one a) N-isopropyl-3-(4-methoxybenzyl)-5-carbamido-2 (3H)-benzoxazolone. The title compound was synthesized by a similar method as for example 98c. The product (231 mg, 65%) was obtained as a White solid, m.p., 192–196° C. $^1$H NMR (300 MHz, CDCl$_3$) δ 7.26–7.21 (m, 3H), 6.92–6.85 (m, 3H), 6.62 (d, J=2.1 Hz, 1H), 4.94 (s, 2H), 4.81 (p, J=6.7 Hz, 1H), 4.03 (s, 2H), 3.78 (s, 3H), 0.93 (d, J=6.7 Hz, 6H).

b) 1-Isopropyl-4-(3,4-ethylenedioxyphenyl)-8-(4-methoxybenzyl)-7-oxo-1,2,3,4-tetrahydro-oxazol[5,4-g] quinazolin-2(1H)-one. The title compound was synthesized by a similar method as for example 98d. The product (100 mg, 32%) was obtained as a white solid, m.p. 154–160° C. $^1$H NMR (300 MHz, CDCl$_3$) δ 7.30 (d, J=8.7 Hz, 2H), 6.90 (d, J=8.7 Hz, 2H), 6.76 (m, 3H), 6.60 (s, 1H), 6.46 (s, 1H), 5.97 (s, 2H), 4.99 (s, 1H), 4.94 (s, 2H), 4.42 (p, J=7.0 Hz, 1H), 3.79 (s, 3H), 1.44 (d, J=7.0 Hz, 3H), 1.41 (d, J=7.0 Hz, 3H).

c) 1-Isopropyl-4-(3,4-ethylenedioxyphenyl)-8-ethyl-7-oxo-1,2,3,4-tetrahydro-oxazol[5,4-g]quinazolin-2(1H)-one. The title compound was synthesized by a similar method as for 98d. The product (35 mg, 30%) was obtained as an earthy colored solid, m.p., 110–130° C. $^1$H NMR (300 MHz, CDCl$_3$) δ 6.88–6.76 (m, 3H), 6.65 (s, 2H), 5.28 (s, 1H), 5.03 (s, 1H), 4.47 (p, J=6.6 Hz, 1H), 4.26 (s, 4H), 3.88 (q, J=6.9 Hz, 2H), 1.61 (t, J=6.6 Hz, 6H), 1.38 (t, J=6.9 Hz, 3H).

d) 1-Isopropyl-4-(3,4-ethylenedioxyphenyl)-8-ethyl-7-oxo-oxazol[5,4-g]quinazolin-2(1H)-one. The title compound was synthesized by a similar method as for example 99c. The product (15 mg, 50%) was obtained as a light yellow solid, m.p., 110–130° C. $^1$H NMR (300 MHz, CDCl$_3$) δ 7.66 (s, 1H), 7.28 (m, 3H), 7.01 (m, 2H), 5.05 (m, 1H), 4.33 (m, 4H), 3.98 (q, J=7.2 Hz, 2H), 1.72 (d, J=7.2 Hz, 6H), 1.46 (t, J=7.2 Hz, 3H).

EXAMPLE 101

1-Isopropyl-4-(2-naphthyl)-8-ethyl-7-oxo-oxazol[5,4-g]quinazolin-2(1H)-one a) 1-Isopropyl-4-(2-naphthyl)-8-ethyl-7-oxo-1,2,3,4-tetrahydro-oxazol[5,4-g]quinazolin-2(1H)-one. The title compound was synthesized b a similar method as for example 98d. The product (52 mg, 38%) was obtained as a earthy yellow solid, m.p., 110–130° C. $^1$H NMR (300 MHz, CDCl$_3$) δ 7.88–7.77 (m, 4H), 7.53–7.41 (m 3H), 6.69 (d, J=4.5 Hz, 2H), 5.57 (s, 1H), 5.254 (s, 1H), 4.48 (p, J=6.9 Hz, 1H), 3.88 (q, J=6.9 Hz, 2H), 1.63 (t, J=6.9 Hz, 6H), 1.38 (t, J=6.9 Hz, 3H).

b) 1-Isopropyl-4-(2-naphthyl)-8-ethyl-7-oxo-oxazol[5,4-g]quinazolin-2(1H)-one. The title compound was synthesized by a similar method as for example 99c. The product (40 mg, 80%) was obtained as an earthy yellow solid, m.p., 256–260° C. $^1$H NMR (300 MHz, CDCl$_3$) δ 8.22 (s, 1H), 8.01–7.93 (m 3H), 7.79 (m 1H), 7.60 (m 3H), 7.06 (s, 1H), 5.09 (m 1H), 4.01 (q, J=7.2 Hz, 2H), 7.76 (d, J=6.6 Hz, 6H), 1.47 (t, J=7.2 Hz, 3H).

c) N-isopropyl-3-propyl-5-carbamido-2(3H)-benzoxazolone. The title compound (450 mg, 80%) was synthesized by a similar method as for example 98c. $^1$H NMR (300 MHz, CDCl$_3$) δ 7.24 (d, J=8.1 Hz, 1H), 6.85 (dd, J=1.6, 8.1 Hz, 1H), 6.80 (d, J=1.6 Hz, 1H), 4.87 (p, J=6.6 Hz, 1H), 4.23 (bs, 2H), 3.80 (t, J=7.0 Hz, 2H), 1.83 (hextet, J=7.0 Hz, 2H), 1.07 (d, J=6.6 Hz, 6H), 1.02 (t, J=7.0 Hz, 3H).

d) 1-Isopropyl-4-(3,4-methylenedioxyphenyl)-8-propyl-7-oxo-1,2,3,4-tetrahydro-oxazol[5,4-g]quinazolin-2(1H)-one. The title compound was synthesized by a similar method as for example 98d. The product (69 mg, 31%) was obtained as a white solid, m.p. 150–155° C. $^1$H NMR (300 MHz, CDCl$_3$) δ 6.79–6.64 (m, 5H), 5.98 (s, 2H), 5.32 (s, 1H), 5.07 (s, 1H), 4.48 (p, J=6.7 Hz, 1H), 3.79 (t, J=6.9 Hz, 2H), 1.82 (sextet, J=6.9 Hz, 2H), 1.62 (d, J=6.7 Hz, 6H), 1.02 (t, J=6.9 Hz, 3H).

e) 1-Isopropyl-4-(3,4-methylenedioxyphenyl)-8-propyl-7-oxo-oxazol[5,4-g]quinazolin-2(1H)-one. The title compound was synthesized by a similar method as for example 99c. The product (45 mg, 80%) was obtained as a light yellow solid, m.p. 110–145° C. $^1$H NMR (300 MHz, CDCl$_3$) δ 7.64 (s, 1H), 7.23–7.00 (m 4H), 6.08 (s, 2H), 5.06 (m, 1H), 3.91 (t, J=6.9 Hz, 1.89 (sextet, J=6.9 Hz, 2H), 1.72 (d, J=6.6 Hz, 6H), 1.07 (t, J=6.9 Hz, 3H).

EXAMPLE 102

4-(3,4-Methylenedioxyphenyl)-6,7-methylenedioxy-1(2D)-phthalazinone

A mixture of 1,3-benzodioxole-6-carboxyl-5-yl-1,3-benzodioxole-5-yl-methanone (522 mg, 1.66 mmol) and hydrazine hydrate (166 mg, 3.32 mmol) % %as heated to reflux in ethanol for overnight. The resulting white precipitate was collected by filtration and washed with a little bit ethanol and dried. The title phthalazinone was obtained as a white solid (282 mg, 55%), 300 MHz $^1$H-NMR (DMSO-d$_6$): δ 12.70 (br, 1H), 7.61 (s, 1H), 7.02 (s, 1H), 6.99 (m, 3H), 6.24 (s, 2H), 6.09 (s, 2H).

EXAMPLE 103

2-[2-(1-Imidazolyl)ethyl]-4-(3,4-methylenedioxyphenyl)-6,7-methylenedioxy-11(2H)-phthalazinone A mixture of 4-(3,4-methylenedioxyphenyl)-6,7-methylenedioxy-1(2H)-phthalazinone (133 mg, 0.43 mmol), 1-(2-bromoethyl)imidazole hydrogen bromide (439 mg, 1.72 mmol), and K$_2$CO$_3$ (415 mg, 3.0 mmol) in DMF (10 mL) was stirred for 5 h at 70° C. The mixture was cooled, and 2N HCl and EtOAc were added to the mixture. The acidic aqueous layer was separated, made alkaline with 5% K$_2$CO$_3$ solution, and extracted with EtOAc. The extract was washed with brine, dried and concentrated under reduced pressure. The residual solid were purified by chromatography on silica gel with CHCl$_3$-MeOH (20:1) to afford the product as a white solid (27 mg, 16%), 300 MHz $^1$H-NMR (CDCl$_3$): δ 7.78 (s, 1H), 7.37 (s, 1H), 7.04–6.86 (m, 5H), 6.13 (s, 2H), 6.03 (s, 2H), 4.58 (m, 2H), 4.45 (m, 2H).

EXAMPLE 104

2-Ethyl-4-(3,4-methylenedioxyphenyl)-6,7-methylenedioxy-1(2H)-phthalazinone

This compound was prepared following the method described in example 103. 300 MHz $^1$H-NMR (CDCl$_3$): δ 7.84 (s, 1H), 7.05–6.93 (m, 4H), 6.13 (s, 2H), 6.05 (s, 2H), 4.32 (q, 2H), 1.42 (t, 2H).

EXAMPLE 105

2-[2-(Dimethylamino)ethyl]-4-(3,4-methylenedioxyphenyl)-6,7-methylenedioxy-1(2H)-phthalazinone This compound was prepared following the method described in example 103. 300 MHz $^1$H-NMR (CDCl$_3$): δ 7.82 (s, 1H), 7.05–6.95 (m, 4H), 6.12 (s, 2H), 6.04 (s, 2H), 4.38 (t, J=7.0 Hz, 2H), 2.80 (t, J=7.0 Hz, 2H), 2.33 (s, 6H).

EXAMPLE 106

2-[2-(1-Pyrrolidinyl)ethyl]-4-(3,4-methylenedioxyphenyl)-6,7-methylenedioxy-1(2H)-phthalazinone This compound was prepared following the method described in example 103. 300 MHz $^1$H-NMR (CDCl$_3$): δ 7.79 (s, 1H), 7.02–6.92 (m, 4H), 6.10 (s, 2H), 6.02 (s, 2H), 4.39 (t, J=7.0 Hz, 2H), 2.93 (t, J=7.0 Hz, 2H), 2.60 (m, 4H), 1.75 (m, 4H).

EXAMPLE 107

2-[2-(1-Piperidinyl)ethyl]-4-(3,4-methylenedioxyphenyl)-6,7-methylenedioxy-1(2H)-phthalazinone This compound was prepared following the method described in example 103. 300 MHz $^1$H-NMR (CDCl$_3$): δ

7.81 (s, 1H), 7.04–6.91 (m, 4H), 6.12 (s, 2H), 6.04 (s, 2H), 4.39 (t, J=7.0 Hz, 2H), 2.81(t, J=7.0 Hz, 2H), 2.51 (m, 4H), 1.56 (m, 4H), 1.41 (m, 2H).

EXAMPLE 108

2-[2(ethoxycarbonyl)ethyl]-4-(3,4-methylenedioxyphenyl)-6,7-methylenedioxy-1(2H)-phthalazinone This compound was prepared following the method described in example 103. 300 MHz $^1$H-NMR (CDCl$_3$): δ 7.81 (s, 1H), 7.05–6.93 (m, 4H), 6.13 (s, 2H), 6.03 (s, 2H), 4.97 (s, 1H), 4.23 (q, J=7.0 Hz, 1H), 1.28 (t, J=7.0 Hz, 3H).

EXAMPLE 109

6,7-Methylenedioxy-4-(3,4-ethylenedioxyphenyl)quinazolin-2(1H)-one 3,4-(Ethylenedioxy)-2-amino-4,5-(methylenedioxy)benzophenone (15.0 g, 52.63 mmol) was dissolved in AcOH (250 mL) by heating. To this reaction mixture was added sodium cyanate (4.1 g, 63.16 mmol) and water (25 mL). The resulting mixture was then stirred at room temp. open to the air. After stirring for 18 h, excess water (120 mL) was added. The precipitate as collected by filtration. The precipitate was washed with water, and dried to give a 6,7-methylenedioxy-4-(3,4-ethylenedioxyphenyl)quinazolin-2(1H)-one as yellow solid (15.7 g); $C_{16}H_{10}N_2O_5$; mp>300° C. $^1$H NMR (DMSO) δ 11.80 (s, 1H), 7.11 (s, 1H), 7.08 (d, J=2.4 Hz, 1H), 6.98–7.02 (m, 2H), 6.79 (s, 11), 6.14 (s, 2H), 4.30 (s, 4H).

EXAMPLE 110a AND 110b 6,7-Methylenedioxy-4-(3,4-ethylenedioxyphenyl)-2-(2-(dimethylamino)ethoxy)-quinazoline and 1-(2-(dimethylamino)ethyl)-6,7-methylenedioxy-4-(3,4-ethylenedioxyphenyl)-quinazolin-2(1H)-one To a suspension of 6,7-methylenedioxy-4-(3,4-ethylenedioxyphenyl)-quinazolin-2-one (400 mg, 1.29 mmol) in DMF (15 mL) was added KOtBu (95%, 232 mg, 2.06 mmol) at room temp. and stirred for 45 minutes. Separately, a solution of 2-dimethylaminoethyl chloride hydrochloride (371 mg, 2.58 mmol) in benzene (12 mL) was treated with a solution of 2 N NaOH (10 mL). The benzene layer, which contained the free base, was dried over anhydrous MgSO$_4$, and added to the above reaction mixture at room temp. The resulting mixture was then heated at 110° C. under argon gas for 15 h. The reaction mixture was then poured into ice-water (50 mL). It was stirred for 30 minutes. The resulting precipitate was collected by filtration. It was dissolved in ethyl acetate. The organic layer was washed with water and brine. Bier being dried over anhydrous MgSO$_4$ the solvent was removed in vacuo. This crude product was then dissolved in a small amount of CHCl$_3$ and poured on a column of silica gel. Elution with acetone:CH$_2$Cl$_2$:MeOH (90:5:5) gave 6,7-methylenedioxy-4-(3,4-methylenedioxyphenyl)-2-(2-(dimethylamino)ethoxy)-quinazoline as a first fraction as yellow solid (110 mg); $C_{21}H_{21}N_3O_5$; mp120–123° C. $^1$H NMR (CDCl$_3$) δ 7.33 (s, 1H), 7.20–7.27 (m, 2H), 7.14 (s, 1H), 6.95 (d, J=7.80 Hz, 1H), 6.08 (s, 2H), 4.59 (m, 2H), 4.32 (s, 4H), 2.83 (m, 2H), 2.38 (s, 6H). Further elution with the same solvent mixture gave 1-(2-(dimethylamino)ethyl)-6,7-methylenedioxy-4-(3,4-ethylenedioxyphenyl)-quinazolin-2(1H)-one as pale yellow solid (90 mg); $C_{21}H_{21}N_3O_5$; mp 220–225° C. $^1$H NMR (CDCl$_3$) δ 7.24 (s, 1H), 7.23 (s, 1H), 7.16–7.19 (m, 2H), 6.95 (d, J=8.4 Hz, 1H), 6.09 (s, 2H), 4.40 (m, 2H), 4.31 (s, 4H), 2.76 (m, 2H), 2.43 (s, 6H).

The potency of antagonism or potentiation for these compounds were determined by electrophysiological assay. Potencies of selective compounds described above in inhibiting or modulating AMPA receptors expressed in oocyte and their anticonvulsant activity against maximal electroshock induced convulsion are shown in Table 1.

TABLE 1

| Compound Name | AMPA IC$_{50}$ μM | MES ED$_{50}$ mg/kg (iv) |
|---|---|---|
| 1-[2-(dimethylamino)ethyl]-4-(3,4-ethylenedioxyphenyl)-6,7-methylenedioxyquinazoline-2-one | 0.2 | 1 |
| 1-(2-(dimethylamino)ethyl)-6,7-methylenedioxy-4-(3,4-methylenedioxyphenyl)quinazolin-2(1H)-one | 1 | 1.5 |
| 1-(2-aminoethyl)-6,7-methylenedioxy-4-(3,4-methylenedioxyphenyl)quinazolin-2(1H)-one | 1 | |
| 1-Ethyl-6,7-methylenedioxy-4-(3,4-ethylenedioxyphenyl)quinazolin-2(1H)-one | 1.1 | 3 |
| 1-(2-(dimethylamino)ethyl)-6,7-methylenedioxy-4-(3,4-methylenedioxyphenyl)quinazolin-2-(1H)-one hydrochloride | 1.1 | 8.1 |
| 1-[(2-Hydroxy)ethyl]-6,7-methylenedioxy-4-(3,4-methylenedioxyphenyl)quinazoline-2-one | 1.5 | |
| 1-Ethylpyrrolidine-6,7-methylenedioxy-4-(3,4-methlenedioxyphenyl)quinazoline-2-one | 1.6 | |
| 4-(3,4-Ethylenedioxyphenyl)-1-isopropyl-6,7-methylenedioxyquinazolin-2(1H)-one | 1.8 | |
| 1-Isopropyl-6,7-methylenedioxy-4-(2-naphthyl)quinazolin-2(1H)-one | 2 | 4.5 |
| 1-(2-(diethylamino)ethyl)-6,7-methylenedioxy-4-(3,4-methylenedioxyphenyl)quinazolin-2(1H)-one | 2 | 5.2 |
| 4-(3,4-difluoromethylenedioxyphenyl)-1-isopropyl-6,7-methylenedioxyquinazolin-2(1H)-one | 2 | |
| 1-Isopropyl-4-(3,4-methylenedioxyphenyl)-8-methyl-7-oxo-oxazol[5,4-g]quinazolin-2(1H)-one | 2 | 1.5 |
| 2-[(2-(dimethylamino)ethoxy]-4-(3,4-methylenedioxyphenyl)-6,7-methylenedioxyquinazoline | 2.5 | 4 |
| 1-Isopropyl-6,7-methylenedioxy-4-(3,4-methylenedioxyphenyl)quinazolin-2(1H)-one | 2.8 | 3 |
| 2-(2-chloroethyl)-6,7-methylenedioxy-4-(3,4-methylenedioxyphenyl)quinazoline | 3 | |
| 1-(3-Dimethylaminopropyl)-6,7-methylenedioxy-4-(3,4-methylenedioxyphenyl)quinazoline-2-one | 3 | |
| 2-ethyl-4-(3,4-methylenedioxyphenyl)-6,7-methylenedioxy-1(2H)-phthalazinone | 3 | |
| 2-[2-(ethoxycarbonyl)ethyl]-4-(3,4-methylenedioxyphenyl)-6,7-methylenedioxy-1(2H)-phthalazinone | 3 | |
| 1-Isopropyl-4-(3,4-methylenedioxyphenyl)-8-benzyl-7-oxo-oxazol[5,4-g]quinazolin-2(1H)-one | 3 | |
| 1-Isopropyl-4-(3,4-ethylenedioxyphenyl)-8-methyl-7-oxo-oxazol[5,4-g]quinazolin-2(1H)-one | 3.2 | |
| 6,7-Methylenedioxy-4-(3,4-methylenedioxyphenyl)-1-(2-morpholinylethyl)quinazolin-2(1H)-one | 4 | |
| 6,7-Methylenedioxy-2-(imidazol-1-yl)ethyl-4-(3,4-methylenedioxyphenyl)quinazoline | 4 | 3.1 |
| 1-[2-(N-methylpyrrolidin-1-yl)ethyl]-6,7-methylenedioxy-4-(3,4-methylenedioxyphenyl)quinazoline-2-one | 4 | |
| 1-(Piperidin-1-yl)ethyl-6,7-methylenedioxy-4-(3,4-methylenedioxyphenyl)quinazoline-2-one | 4 | |
| 2-Methyl-5,6-methylenedioxy-4-(3,4-methylenedioxyphenyl)quinazoline 3-oxide | 4 | |
| 2-[(2-Hydroxy)ethoxy]-6,7-methylenedioxy-4-(3,4-methylenedioxyphenyl)quinazoline | 4 | |
| 6,7-methylenedioxy-4-(3,4-methylenedioxyphenyl)-2-ethylquinazoline | 4.3 | |
| 6,7-methylenedioxy-4-(3,4-methylenedioxyphenyl)-3-methylquinazoline | 4.5 | |

TABLE 1-continued

| Compound Name | AMPA IC$_{50}$ μM | MES ED$_{50}$ mg/kg (iv) |
|---|---|---|
| 1-Ethyl-6,7-methylenedioxy-4-(3,4-methylenedioxy-6-nitrophenyl)quinazolin-2(1H)-one | 4.7 | |
| 1-(Imidazol-1-yl)ethyl-6,7-methylenedioxy-4-(3,4-methylenedioxyphenyl)quinazoline-2-one | 5 | |
| 1-Ethyl-6,7-methylenedioxy-2-(3,4-methylenedioxyphenyl)quinazolin-2(1H)-one | 5 | 3.4 |
| 1-Ethyl-6,7-methylenedioxy-4-(2-naphthyl)quinazolin-2(1H)-one | 5 | |
| 1-isopropyl-6,7-methylenedioxy-4-(5-indanyl)-quinazolin-2(1H)-one | 5 | |
| 2-[2-(Dimethylamino)ethyl]-4-(3,4-methylenedioxyphenyl)-6,7-methylenedioxy-1(2H)-phthalazinone | 5 | 3.5 |
| 2-(1-Imidazolyl)methyl-5,6-methylenedioxy-4-(3,4-methylenedioxyphenyl)quinazoline 3-oxide | 5 | 5 |
| 3-Propyl-2-oxazolono[4,5-g]-4-(3,4-methylenedioxyphenyl)-1-isopropylquinazolin-2(1H)-one | 5 | |
| 1-Isopropyl-6,7-methylenedioxy-4-(6-chloro-3,4-methylenedioxyphenyl)-quinazolin-2(1H)-one | 5.5 | 6.2 |
| 2-Ethoxy-6,7-methylenedioxy-4-(3,4-methylenedioxyphenyl)-quinazoline | 6 | |
| 1-cyclopropylmethyl-6,7-methylenedioxy-4-(3,4-methylenedioxyphenyl)quinazolin-2(1H)-one | 6 | |
| 6,7-methylenedioxy-4-(3,4-methylenedioxyphenyl)-2-(1-hydroxy-1-methylethyl)quinazoline | 6 | |
| 2-Chloro-6,7-methylenedioxy-4-(3,4-methylenedioxyphenyl)quinazoline | 6 | |
| 2-Hydroxymethyl-6,7-methylenedioxy-4-(3,4-methylenedioxyphenyl)quinazoline | 6 | |
| 2-[2-(1-Imidazolyl)ethyl]-4-(3,4-methylenedioxyphenyl)-6,7-methylenedioxy-1(2H)-phthalazinone | 6 | |
| 2-(1-Imidazolyl)methyl-5,6-methylenedioxy-4-(3,4-methylenedioxyphenyl)quinazoline 3-oxide hydrochloride | 6 | |
| 1-Ethyl-6,7-methylenedioxy-4-(2-amino-4,5-methylenedioxyphenyl)quinazolin-2(1H)-one | 7 | |
| 1-(2-propynyl)-6,7-methylenedioxy-4-(3,4-methylenedioxyphenyl)quinazolin-2(1H)-one | 7 | |
| 1-isopropyl-6,7-ethylenedioxy-4-(3,4-methylenedioxyphenyl)quinazolin-2(1H)-one | 7 | |
| 5,6-methylenedioxy-4-(3,4-methylenedioxyphenyl)quinazoline 3-oxide | 7 | 2.5 |
| 2-((1-methyl-2-imidazolyl)thio)methyl-6,7-methylenedioxy-4-(3,4-methylenedioxyphenyl)quinazoline | 7 | |
| 2-Iodomethyl-6,7-methylenedioxy-4-(3,4-methylenedioxyphenyl)quinazoline | 7 | |
| 5,6-methylenedioxy-4-(3,4-methylenedioxyphenyl)-2-(1-pyrrolidinyl)methyl-quinazoline 3-oxide | 7 | |
| 2-(2-dimethylaminoethyl)-6,7-methylenedioxy-4-(3,4-methylenedioxyphenyl)quinazoline | 8 | |
| 1-isopropyl-6,7-methylenedioxy-4-(3-quinolinyl)quinazolin-2(1H)-one | 8 | |
| 2-Chloromethyl-5,6-methylenedioxy-4-(3,4-methylenedioxyphenyl)quinazoline 3-oxide | 8 | 3.1 |
| 1-[(2-Ethoxy)ethyl]-6,7-methylenedioxy-4-(3,4-methylenedioxyphenyl)quinazoline-2-one | 8 | 10 |
| 6,7-methylenedioxy-2-(1,2,4-triazol-1-yl)methyl-4-(3,4-methylenedioxyphenyl)quinazoline | 9 | |
| 2-[2-(Imidazol-1-yl)ethoxy]-6,7-methylenedioxy-4-(3,4-methylenedioxyphenyl)quinazoline | 10 | |
| 6,7-methylenedioxy-4-(3,4-methylenedioxyphenyl)-2-(2-(dimethylamino)ethoxy)quinazoline hydrochloride | 10 | 10 |
| 1-isopropyl-6,7-methylenedioxy-4-(2,3-dihydrobenzo(b)furan-5-yl)quinazolin-2-(1H)-one | 10 | 3.3 |
| 2[2-(1-Pyrrolidinyl)ethyl]-4-(3,4-methylenedioxyphenyl)-6,7-methylenedioxy-1(2H)-phthalazinone | 10 | 3.8 |
| 2-Dimethylaminomethyl-4-(3,4-methylenedioxyphenyl)-6,7-methylenedioxyquinazoline-3-oxide | 10 | |
| 6,7-methylenedioxy-4-(3,4-methylenedioxyphenyl)quinazoline | 11 | |
| 6,7-methylenedioxy-4-(3,4-methylenedioxyphenyl)-2-(3-chloropropyl)quinazoline | 11 | |
| 2-(2-aminoethoxy)-6,7-methylenedioxy-4-(3,4-methylenedioxyphenyl)quinazoline | 12 | |
| 2-(3-aminopropyl)-6,7-methylenedioxy-4-(3,4-methylenedioxyphenyl)quinazoline | 12 | |
| 6,7-Methylenedioxy-2-(piperazin-1-yl)methyl-4-(3,4-methylenedioxyphenyl)quinazoline | 12 | |
| 2-[(3-Dimethylaminopropyl)ethoxy]-6,7-methylenedioxy-4-(3,4-methylenedioxyphenyl)quinazoline | 12 | |
| 4-(5-benzoxazolyl)-1-isopropyl-6,7-methylenedioxyquinazolin-2(1H)-one | 13 | |
| 1-[(2-Methoxy)ethyl]-6,7-methylenedioxy-4-(3,4-methylenedioxyphenyl)quinazoline-2-one | 13 | |

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A compound having the Formula II:

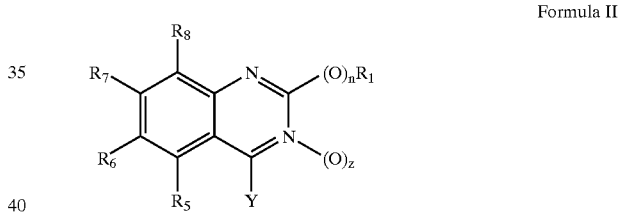

Formula II or a pharmaceutically acceptable salt, ester or amide thereof, wherein:

$R_1$ is alkyl, haloalkyl, aminoalkyl, $C_{1-10}$ alkylaminoalkyl, di($C_{1-10}$)alkylaminoalkyl, alkenyl, alkynyl, aralkyl, aralkenyl, aralkynyl, triazolylalkyl, imidazolylalkyl, carbocycloalkyl, piperidinylalkyl, piperazinylalkyl, pyrrolidinylalkyl, morpholinylalkyl, hydroxyalkyl, cyanoalkyl, alkanoylamidoalkyl, alkanoyloxyalkyl, azidoalkyl, alkenyloxyalkyl, or alkoxyalkyl;

$R_6$ and $R_7$ are taken together to form —OCH$_2$O—, —OCH$_2$CH$_2$O—, —O—CF$_2$—O—, —CD$_2$CH$_2$CH$_2$—, —CH$_2$CH$_2$CH$_2$—,—OCH$_2$CH$_2$—or —N(R$_9$)—CO—O—; and R$_9$ is optionally substituted lower alkyl;

$R_5$ is hydrogen; and $R_8$ is selected from the group consisting of;

n is 0 or 1;

Y is phenyl, biphenyl, indenyl, quinolinyl, or pyridyl optionally substituted with one or more substituents selected from the group consisting of hydrogen, halo, $C_{1-10}$ alkyl, nitro, amino, and alkoxy or

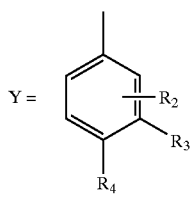

wherein $R_2$ is H, alkyl, halo, amino, alkoxy, or nitro; and $R_3$ and $R_4$ are taken together to form —OCH$_2$O—, —OCH$_2$CH$_2$O—, —O—CF$_2$—O—, —CH$_2$CH$_2$CH$_2$—, —CH$_2$CH$_2$CH$_2$CH$_2$—, —O—CH$_2$—CH$_2$—, —N=CH—O—, —NH—CO—O—, —CH=CH—CH=CH—, or —O—CH=CH—; and z is 0 or 1 with the proviso that when $R_6$ and $R_7$ are taken together as —OCH$_2$O—, $R_1$ is alkyl and z is 0, then Y is not 3-indazolyl.

2. The compound according to claim 1, wherein $R_6$ and $R_7$ taken together are —OCH$_2$O—, —OCH$_2$CH$_2$O—, —O—CF$_2$—O—, —CH$_2$CH$_2$CH$_2$—, or —CH$_2$CH$_2$CH$_2$CH$_2$——OCH$_2$CH$_2$— or —N($R_9$)—CO—O—; wherein $R_9$ is optionally substituted lower alkyl.

3. A compound according to claim 1, wherein, n is 1; z is 0 or 1;

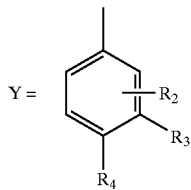

wherein $R_2$, $R_3$ and $R_4$ are as defined in claim 1.

4. The compound according to claim 3, wherein $R_3$ and $R_4$ taken together are —OCH$_2$O—, —OCH$_2$CH$_2$O—, —O—CF$_2$—O—, —CH$_2$CH$_2$CH$_2$—, —CH$_2$CH$_2$CH$_2$CH$_2$—, —O—CH$_2$—CH$_2$—, —CH=CH—CH=CH—, or —O—CH=CH—.

5. A compound according to claim 1, said compound selected from the group consisting of:

2-(2-diethylaminoethoxy)-6,7-methylenedioxy-4-(3,4-methylenedioxyphenyl)quinazoline, 2-(2-dimethylaminoethoxy)-6,7-methylenedioxy-4-(3,4-methylenedioxyphenyl)quinazoline, 2-(2-dimethylaminoethoxy)-6,7-methylenedioxy-4-(3,4-methylenedioxyphenyl)quinazoline, 2-(2-aminoethoxy)-6,7-methylenedioxy-4-(3,4-methylenedioxyphenyl)quinazoline, and 2-(2-pyrrolidinoethoxy)-6,7-methylenedioxy-4-(3,4-methylenedioxyphenyl)quinazoline.

6. A compound according to claim 1, wherein n is 0; z is 0;

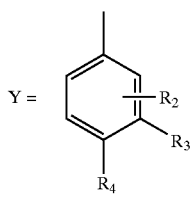

$R_2$ is H, alkyl, halo, amino, alkoxy, or nitro; and $R_3$ and $R_4$ are taken together to form —OCH$_2$O—, —OCH$_2$CH$_2$O—, —O—CF$_2$—O—, —CH$_2$CH$_2$CH$_2$—, —CH$_2$CH$_2$CH$_2$CH$_2$—, —O—CH$_2$—CH$_2$—, —N=CH—O—, —NH—CO—O—, —CH=CH—CH=CH—, or —O—CH=CH—.

7. A compound according to claim 6, said compound selected from the group consisting of:

2-methyl-6,7-methylenedioxy-4-(3,4-methylenedioxyphenyl)quinazoline, 2-(1-hydroxy-1-methyl)ethyl-6,7-methylenedioxy-4-(3,4-methylene-dioxyphenyl)quinazoline, 2-ethyl-6,7-methylenedioxy-4-(3,4-methylenedioxyphenyl)-quinazoline, 2-benzyl-6,7-methylenedioxy-4-(3,4-methylenedioxyphenyl)-quinazoline, 2-dimethylamino-6,7-methylenedioxy-4-(3,4-methylenedioxyphenyl)-quinazoline, 2-(2-diethylaminoethyl)-6,7-methylenedioxy-4-(3,4-methylene-dioxyphenyl)quinazoline, 2-(2-chloroethyl)-6,7-methylenedioxy-4-(3,4-methylene-dioxyphenyl)quinazoline, 2-(2-dimethylamino-1-methyl)-6,7-methylenedioxy-4-(3,4-methylenedioxyphenyl)quinazoline, 2-chloromethyl-6,7-methylenedioxy-4-(3,4-methylenedioxyphenyl)-quinazoline, 2-(2-dimethylamino-1-methylethoxy)-6,7-methylenedioxy-4-(3,4-methylenedioxyphenyl)quinazoline, 2-(3-chloropropyl)-6,7-methylenedioxy-4-(3,4-methylenedioxyphenyl)quinazoline, 2-(3-aminopropyl)-6,7-methylenedioxy-4-(3,4-methylenedioxyphenyl)quinazoline, 2-n-pentyl-6,7-methylenedioxy-4-(3,4-methylenedioxyphenyl)-quinazoline, 2-(imidazol-1-yl)methyl-6,7-methylenedioxy-4-(3,4-methylene-dioxyphenyl)quinazoline, 6,7-methylenedioxy-4-(3,4-methylenedioxyphenyl)-2-(1,2,4-triazol-1-yl)methyl-quinazoline, 2-(imidazol-1-yl)ethyl-6,7-methylenedioxy-4-(3,4-methylenedioxy-phenyl)quinazoline, 2-iodomethyl-6,7-methylenedioxy-4-(3,4-methylenedioxyphenyl) quinazoline, 2-acetoxymethyl-6,7-methylenedioxy-4-(3,4-methylenedioxyphenyl) quinazoline, 2-(2-morpholinoethyl)-6,7-methylenedioxy-4-(3,4-methylenedioxyphenyl)quinazoline, and 2-piperazinomethyl-6,7-methylenedioxy-4-(3,4-methylenedioxyphenyl)quinazoline.

8. A compound according to claim 1, wherein n is 0; z is 1;

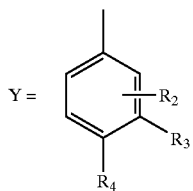

$R_2$ is H, alkyl, halo, amino, alkoxy, or nitro; and $R_3$ and $R_4$ are taken together to form —OCH$_2$O—, —OCH$_2$CH$_2$O—, —O—CF$_2$—O—, —CH$_2$CH$_2$CH$_2$—, —CH$_2$CH$_2$CH$_2$CH$_2$—, —O—CH$_2$—CH$_2$—, —N=CH—O—, —NH—CO—O—, —CH=CH—CH=CH—, or —O—CH=CH—.

9. A compound according to claim 8, said compound selected from the group consisting of:

2-Chloromethyl-6,7-methylenedioxy-4-(3,4-methylenedioxyphenyl)quinazoline 3-oxide, 2-Ethyl-6,7-methylenedioxy-4-(3,4-methylenedioxyphenyl)quinazoline 3-oxide, 2-Methyl-6,7-methylenedioxy-4-(3,4-methylenedioxyphenyl)quinazoline 3-oxide, 2-(1-Imidazolyl)methyl-6,7-methylenedioxy-4-(3,4-methylenedioxy -phenyl)quinazoline 3-oxide, 6,7-Methylenedioxy-4-(3,4-methylenedioxyphenyl)-2-(1-pyrrolidinyl)-methyl -quinazoline 3-oxides, 2-Dimethylaminomethyl-4-(3,4-methylenedioxyphenyl)-6,7-methylenedioxyquinazoline-3-oxide, and 2-Methylaminomethyl-4-(3,4-methylenedioxyphenyl)-6,7-methylenedioxyquinazoline 3-oxide.

10. A pharmaceutical composition comprising the compound of claim 1 and a pharmaceutically acceptable carrier.

11. A compound selected from the group consisting of:

6,7-methylenedioxy-4-(3,4-methylenedioxyphenyl) quinazoline, 2-((1-methyl-2-imidazolyl)thio)methyl-6,7-methylenedioxy-4-(3,4-methylenedioxyphenyl) quinazoline, and 6,7-methylenedioxy-4-(3,4-methylenedioxyphenyl) quinazoline 3-oxide.

* * * * *